(12) United States Patent
Li

(10) Patent No.: US 11,090,372 B2
(45) Date of Patent: *Aug. 17, 2021

(54) METHOD OF TREATING DIABETIC NEPHROPATHY COMPRISING ADMINISTERING PLASMINOGEN

(71) Applicant: TALENGEN INTERNATIONAL LIMITED, Hong Kong (CN)

(72) Inventor: Jinan Li, Shenzhen (CN)

(73) Assignee: TALENGEN INTERNATIONAL LIMITED, Hong Kong (CN)

( * ) Notice: Subject to any disclaimer, the term of this patent is extended or adjusted under 35 U.S.C. 154(b) by 44 days.

This patent is subject to a terminal disclaimer.

(21) Appl. No.: 16/062,049

(22) PCT Filed: Dec. 16, 2016

(86) PCT No.: PCT/CN2016/110450
§ 371 (c)(1),
(2) Date: Jun. 13, 2018

(87) PCT Pub. No.: WO2017/101868
PCT Pub. Date: Jun. 22, 2017

(65) Prior Publication Data
US 2019/0015485 A1 Jan. 17, 2019

(30) Foreign Application Priority Data

Dec. 18, 2015 (WO) ................ PCT/CN2015/097944

(51) Int. Cl.
| | | |
|---|---|---|
| A61K 38/49 | (2006.01) | |
| A61K 38/00 | (2006.01) | |
| A61P 13/12 | (2006.01) | |
| A61K 9/00 | (2006.01) | |
| A61K 45/06 | (2006.01) | |
| A61K 38/48 | (2006.01) | |
| A61P 25/02 | (2006.01) | |

(52) U.S. Cl.
CPC ............ *A61K 38/49* (2013.01); *A61K 9/0019* (2013.01); *A61K 38/00* (2013.01); *A61K 38/484* (2013.01); *A61P 13/12* (2018.01); *A61P 25/02* (2018.01); *A61K 45/06* (2013.01); *A61K 2300/00* (2013.01)

(58) Field of Classification Search
None
See application file for complete search history.

(56) References Cited

U.S. PATENT DOCUMENTS

| | | |
|---|---|---|
| 2003/0018067 A1 | 1/2003 | Elokdah |
| 2003/0113313 A1 | 6/2003 | Peyman |
| 2003/0147876 A1 | 8/2003 | Ni |
| 2003/0175263 A1 | 9/2003 | Trese |
| 2003/0180934 A1 | 9/2003 | Ni et al. |
| 2005/0250694 A1 | 11/2005 | Ma |
| 2006/0014725 A1 | 1/2006 | Mayer |
| 2006/0052348 A1 | 3/2006 | Commons |
| 2006/0052349 A1 | 3/2006 | Commons |
| 2006/0234913 A1* | 10/2006 | Arbit .................... A61P 9/00 514/1.9 |
| 2006/0257391 A1 | 11/2006 | Bartels |
| 2007/0043101 A1 | 2/2007 | Hu |
| 2007/0185017 A1* | 8/2007 | Aggarwal ............. C07K 14/47 514/1.7 |
| 2007/0196350 A1 | 8/2007 | Bartels |
| 2012/0114652 A1 | 5/2012 | Elvin |
| 2013/0266566 A1 | 10/2013 | Anderson |
| 2013/0273028 A1* | 10/2013 | Zwaal ................. C12N 9/6435 424/94.64 |
| 2018/0360930 A1 | 12/2018 | Li |
| 2018/0369345 A1 | 12/2018 | Li |

FOREIGN PATENT DOCUMENTS

| | | |
|---|---|---|
| CA | 2703494 A1 | 4/2009 |
| CA | 3002915 A1 | 5/2017 |
| CN | 1195375 A | 10/1998 |
| CN | 1451746 A | 10/2003 |
| CN | 1543456 A | 11/2004 |
| CN | 1549814 A | 11/2004 |
| CN | 1585649 A | 2/2005 |
| CN | 1643140 A | 7/2005 |
| CN | 1768138 A | 5/2006 |
| CN | 1946352 A | 4/2007 |
| CN | 1961958 A | 5/2007 |
| CN | 101263115 A | 5/2007 |
| CN | 1990871 A | 7/2007 |
| CN | 101002888 A | 7/2007 |
| CN | 101039936 A | 9/2007 |
| CN | 101044136 A | 9/2007 |
| CN | 101171030 A | 4/2008 |
| CN | 101227918 A | 7/2008 |
| CN | 101563100 A | 10/2009 |
| CN | 101573134 A | 11/2009 |
| CN | 101918548 A | 12/2010 |

(Continued)

OTHER PUBLICATIONS

Martin-Fernandez et al., Scientific Reports, 2016; 6: 39255; doi: 10.1038/srep39255; 7 pages total (Year: 2016).*
Ma et al., Blood, 2014; 124: 3155-3164 (Year: 2014).*
Bhattacharya et al., PLoS ONE 12(3): e0171355. https://doi.org/10.1371/journal.pone.0171355; 22 pages total (Year: 2017).*
Zhang et al., J Am Soc Nephrol, 2006; 17: 475-486 (Year: 2006).*
Alicic et al., Clin J Am Soc Nephrol 12: 2032-2045, 2017. doi: https://doi.org/10.2215/CJN.11491116 (Year: 2017).*
Williams, Am J Nephrol 2005;25:77-94 (Year: 2005).*

(Continued)

*Primary Examiner* — Christina M Borgeest
(74) *Attorney, Agent, or Firm* — Morrison & Foerster LLP

(57) ABSTRACT

The present invention relates to the effect of plasminogen in the prevention and/or treatment of diabetic nephropathy. Compared with other existing drugs for treating diabetic nephropathy, the plasminogen of the present invention has significant effects of improving renal microvascular injury, reducing glomerular basement membrane and glomerular mesangial thickening, and the like.

19 Claims, 10 Drawing Sheets

Specification includes a Sequence Listing.

(56) References Cited

FOREIGN PATENT DOCUMENTS

| | | |
|---|---|---|
| CN | 102121023 A | 7/2011 |
| CN | 102154253 A | 8/2011 |
| CN | 102250210 A | 11/2011 |
| CN | 102872020 A | 1/2013 |
| CN | 103384722 A | 11/2013 |
| CN | 103764163 A | 4/2014 |
| CN | 104789544 A | 7/2015 |
| CN | 105008323 A | 10/2015 |
| CN | 105705520 A | 6/2016 |
| EP | 3395359 A1 | 10/2018 |
| EP | 3395360 A1 | 10/2018 |
| JP | 2009-196927 A | 9/2009 |
| JP | 2019500422 A | 1/2019 |
| TW | 201625294 A | 7/2016 |
| TW | 201822800 A | 7/2018 |
| TW | 201822801 A | 7/2018 |
| TW | 201822802 A | 7/2018 |
| TW | 201822803 A | 7/2018 |
| TW | 201822804 A | 7/2018 |
| TW | 201822807 A | 7/2018 |
| TW | 201822808 A | 7/2018 |
| WO | WO199635774 A2 | 11/1996 |
| WO | WO199635774 A3 | 2/1997 |
| WO | WO199900420 A1 | 1/1999 |
| WO | WO200018436 A1 | 4/2000 |
| WO | WO200044391 A2 | 8/2000 |
| WO | WO200044391 A3 | 12/2000 |
| WO | WO-2003/020297 A2 | 3/2003 |
| WO | WO-2003/020297 A3 | 3/2003 |
| WO | WO2003066842 A2 | 8/2003 |
| WO | WO2003095637 A1 | 11/2003 |
| WO | WO2004039956 A2 | 5/2004 |
| WO | WO2003066842 A3 | 6/2004 |
| WO | WO2004052228 A2 | 6/2004 |
| WO | WO2004052228 A3 | 10/2004 |
| WO | WO2006118805 A2 | 11/2006 |
| WO | WO2007051314 A1 | 5/2007 |
| WO | WO2006118805 A3 | 6/2007 |
| WO | WO-2008/026999 A2 | 3/2008 |
| WO | WO-2008/026999 A3 | 3/2008 |
| WO | WO2004039956 A3 | 4/2009 |
| WO | WO2009073471 A1 | 6/2009 |
| WO | WO2012093132 A1 | 7/2012 |
| WO | WO2013024074 A1 | 2/2013 |
| WO | WO2014070983 A1 | 5/2014 |
| WO | WO2014070986 A1 | 5/2014 |
| WO | WO2015023752 A1 | 2/2015 |
| WO | WO2016095013 A1 | 6/2016 |
| WO | WO2017101866 A1 | 6/2017 |
| WO | WO2017101868 A1 | 6/2017 |

OTHER PUBLICATIONS

Jerzy Jankun, Experimental and Therapeutic Medicine 4: 661-664, 2012 (Year: 2012).*
Auwerx, J. et al. (Jan./Feb. 1988). "Tissue-Type Plasminogen Activator Antigen and Plasminogen Activator Inhibitor in Diabetes Mellitus," Arteriosclerosis 8:68-72.
Brazionis, L. et al. (2008). "Plasminogen Activator Inhibitor-1 Activity in Type 2 Diabetes a Different Relationship With Coronary Heart Disease and Diabetic Retinopathy," Arterioscler Thromb Vasc. Biol. 28:786-791.
Fisher, E.J. et al. (1997). "Displacement of Tissue Bound Plasminogen by Glucose: A Possible Mechanism in the Pathogenesis of Diabetic Nephropathy," Endocrinology and Metabolism 4:371-376.
Lugea, A. et al. (Sep. 2006). "Pancreas Recovery Following Caerulein-Induced Pancreatitis is Impaired in Plasminogen Deficient Mice," Gastroenterology 131(3):885-899.
Ma, L.-J. et al. (Feb. 2004). "Prevention of Obesity and Insulin Resistance in Mice Lacking Plasminogen Activator Inhibitor 1," Diabetes 53:336-346.
Miles, L.A. et al. (Nov. 11, 2016). "Abstract 19088 the Plasminogen Receptor, Plg-Rkt, Regulates Metabolic Homeostasis and Promotes Healthy Adipose Function," Circulation 134(Suppl 1), 2 pages.
NCBI Reference Sequence—NP_000292.1 (May 4, 2019). "Plasminogen Isoform 1 Precursor [Homo sapiens]," 4 pages.
Schott, D. et al. (Dec. 3, 1998). "Therapy With a Purified Plasminogen Concentrate in an Infant With Ligneous Conjunctivitis and Homozygous Plasminogen Deficiency," The New England Journal of Medicine 339(23):1679-1686.
Wang, Q. (Sep. 2005). "Rest and Protection of Pancreatic Islet Beta-Cell," Chinese Nursing Research 19 (9)1706-1708. English Abstract.
Zhang, S.X. et al. (Jan. 4, 2006). "Therapeutic Potential of Angiostatin in Diabetic Nephropathy," J. Am. Soc. Nephrol. 13 pages.
Zhou, H. et al. (Aug. 2011). "Treatment of 62 Cases of Type 2 Diabetes With Plasmin," 30(Suppl):35-36. English Abstract.
Ajjan, R.A. et al. (Jul. 4, 2013). "Diabetes Is Associated With Posttranslational Modifications In Plasminogen Resulting in Reduced Plasmin Generation and Enzyme-Specific Activity." Blood 122(1):134-142.
Andreasen, P.A. et al. (1997). "The Urokinase-Type Plasminogen Activator System in Cancer Metastasis: A Review," Int. J. Cancer 72:1-22.
Chen, W. (Apr. 15, 2007). "Pilot Production and Pharmacodynamics Study of Recombinant Human Microplasminogen," Doctoral Dissertation, Fudan University, 127 pages. (With English Abstract).
Collen, D et al. (Dec. 15, 1991) "Review Article: Basic and Clinical Aspects of Fibrinolysis and Thrombolysis," Blood 78(12):3114-3124.
Collen, D. (2001). "Ham-Wasserman Lecture: Role of the Plasminogen System in Fibrin-Homeostasis and Tissue Remodeling," Hematology pp. 1-9.
Davalos, D. et al. (2012, e-pub. Oct. 31, 2011). "Fibrinogen as a Key Regulator of Inflammation in Disease," Semin. Immunopathol. 34:43-62.
Du Z. et al. (Dec. 31, 1997). "Changes of Plasm tPA and PAI Activities in Patients With Diabetic Retinopathy," Eye Science 13(1):17-20.
Gao, C. et al. (Feb. 2007). "Relationship Between Type Diabetic Retinopathy and Plasma Fibrinolysis," Progress in Modern Biomedicine 7(2):257-258. (With English Abstract).
Hay, E.D. (1991). Cell Biology of Extracellular Matrix, $2^{nd}$ Ed. Springer Science+Business Media, LLC., 15 pages. Table of Contents.
He, C. et al. (Apr. 1989). "Tissue Cooperation in a Proteolytic Cascade Activating Human Interstitial Collagenase," Proc. Natl. Acad. Sci. USA 86:2632-2636.
Hunt, J.A. et al. (2008, e-pub. Aug. 14, 2008). "Simplified Recombinant Plasmin: Production and Functional Comparison of a Novel Thrombolytic Molecule With Plasma-Derived Plasmin," Thromb. Haemost. 100:413-419.
Jin, X. et al. (Aug. 2002). "Catabolic Enzymes of Extracellular Matrix and Diabetic Nephropathy," Medical Journal of the Chinese Coal Industry 5(8):825-826. With English Translation.
Knudsen, B.S. et al. (Aug. 15, 1986). "Binding of Plasminogen to Extracellular Matrix," The Journal of Biological Chemistry 261(23):10765-10771.
Lee, H.B. et al. (2005). "Plasminogen Activator Inhibitor-1 and Diabetic Nephropathy," Nephrology 10:S11-S13.
Li, J. et al. (Sep. 2008). "Catabolic Enzymes of Extracellular Matrix and Diatetic Nephropathy," Medical Recapitulate 14(17):2611-2613. English Translation Abstract Only.
Marder, V. J. et al. (2010). "Direct Fibrinolytic Agents: Biochemical Attributes, Preclinical Foundation and Clinical Potential," J. Thromb. Haemost. 8:433-444.
Mignatti, P. et al. (Jan. 1993). "Biology and Biochemistry of Proteinases in Tumor Invasion," Physiological Reviews 73(1):161-195.
Nagai, N. et al. (2002). "Recombinant Human Microplasmin: Production and Potential Therapeutic Properties," Journal of Thrombosis and Haemostasis 1:307-313.
Raum, D. et al. (May 30, 1980). "Synthesis of Human Plasminogen by the Liver," Science 208(4447):1036-1037, 4 pages.

(56) References Cited

OTHER PUBLICATIONS

Rifkin, D.B. et al. (1990). "Growth Factor Control of Extracellular Proteolysis," *Cell Differentiation and Development* 32:313-318.
Rifkin, D.B. et al. (1999). "Proteolytic Control of Growth Factor Availability," *APMIS* 107:80-85.
Ryu, J.K. et al. (Sep. 10, 2015). "Blood Coagulation Protein Fibrinogen Promotes Autoimmunity and Demyelination Via Chemokine Release and Antigen Presentation," *Nature Communication* 6:8164, 15 pages.
Saksela, O. et al. (1988). "Cell-Associated Plasminogen Activation: Regulation and Physiological Functions," *Ann. Rev. Cell Biol.* 4:93-126.
Shen, Y. et al. (Jun. 14, 2012). "Plasminogen Is a Key Proinflammatory Regulator That Accelerates the Healing of Acute and Diabetic Wounds," *Blood* 119(24):5879-5887.
Shi, L. et al. (Nov. 30, 2005). "Comparison of Curative Effects of Kallidinogenase Between Patients with Early Diabetic Nephropathy and Patients with Clinical Diabetic Nephropathy," *Journal of Jilin University (Medicine Edition)*, 31(6):934-936. With English Abstract.
Singh, R. et al. (Dec. 21, 2014). "Diabetic Peripheral Neuropathy: Current Perspective and Future Directions," *Pharmacological Research* 80:21-35.
Sottrup-Jensen, L. et al. (Jul. 1975). "Amino-acid Sequence of Activation Cleavage Site in Plasminogen: Homology With 'Pro' Part of Prothrombin," *Proc. Natl. Acad. Sci. USA* 72(7):2577-2581.
Stoppelli, M.P. et al. (Aug. 1985). "Differentiation-enhanced Binding of the Amino-Terminal Fragment of Human Urokinase Plasminogen Activator to a Specific Receptor on U937 Monocytes," *Proc. Natl. Acad. Sci. USA* 82:4939-4973.
Tyagi, S.C. (1997). "Proteinases and Myocardial Extracellular Matrix Turnover," *Molecular and Cellular Biochemistry* 168:1-12.
Valvi, D. et al. (Mar. 6, 2012). "Fibrinogen, Chronic Obstructive Pulmonary Disease (COPD) and Outcomes in Two United States Cohorts," *International Journal of COPD* 7:173-182.
Vassalli, J.-D. et al. (Jan. 1985). "A Cellular Binding Site for the $M_r$ 55,000 Form of the Human Plasminogen Activator, Urokinase," *The Journal of Cell Biology* 100:86-92.
Wang, X. (Mar. 31, 2014). "Medical Treatment of Painful Diabetic Neuropathy," *Journal of Community Medicine* 12(6):82 & 83, with English Translation Abstract.
Werb, Z. et al. (May 5, 1977). "Endogenous Activation of Latent Collagenase by Rheumatoid Synovial Cells," *The New England Journal of Medicine* 296(18):1017-1023.
Wiman, B. et al. (1975). "Structural Relationship between 'Glutamic Acid' and 'Lysine' Forms of Human Plasminogen and Their Interaction with the NH,-Terminal Activation Peptide as Studied by Affinity Chromatography," *Eur. J. Biochem* 50:489-494.
Xu, A. et al. (Feb. 28, 2014). "New Progress in the Treatment of Diabetic Neuropathic Pain," *Chinese Journal of Clinical Research* 27(2):227,228 & 230, with English Translation Abstract.
Yin, G. et al. (2005) "Cloning Construction and Purification of Recombinant Human Plasminogen Kringle 5 Gene," *Academic Journal of Shanghai Second Medical University* 25(2):151-154. (English Translation of the Abstract).
International Search Report, dated Mar. 21, 2017, for PCT Application No. PCT/CN2016/110449, filed Dec. 16, 2016, 6 pages.
International Search Report, dated Mar. 2, 2017, for PCT Application No. PCT/CN2016/110450, filed Dec. 16, 2016, 4 pages.
International Search Report, dated Feb. 24, 2017, for PCT Application No. PCT/CN2016/110452, filed Dec. 16, 2016, 4 pages.
U.S. Appl. No. 16/063,569, Li, J., filed Jun. 18, 2018.
U.S. Appl. No. 16/063,534, Li, J., filed Jun. 18, 2018.
U.S. Appl. No. 16/062,410, Li, J., filed Jun. 14, 2018.
U.S. Appl. No. 16/062,421, Li, J., filed Jun. 14, 2018.
U.S. Appl. No. 16/062,389, Li, J., filed Jun. 14, 2018.
U.S. Appl. No. 16/062,037, Li, J., filed Jun. 13, 2018.
U.S. Appl. No. 16/062,052, Li, J., filed Jun. 13, 2018.

Akassoglou, K. et al. (May 29, 2000). "Tissue Plasminogen Activator-Mediated Fibrinolysis Protects Against Axonal Degeneration and Demyelination after Sciatic Nerve Injury," *J Cell Biol.* 149(5)1157-1166.
Fowler, M.J. (2008). "Microvascular and Macrovascular Complications of Diabetes," *Clinical Diabetes* 26(2):77-82.
Gutiérrez-Fernández, A. et al. (Oct. 7, 2009). "Plasminogen Enhances Neuritogenesis on Laminin-1," *J Neurosci.* 29(40):12393-12400, 17 pages.
Hafer-Macko, C.E. et al. (Jul. 17, 2007). "Microvascular Tissue Plasminogen Activator Is Reduced in Diabetic Neuropathy," *Neurology* 69(3):268-274.
Kimiyoshi, A. et al. (2009). "Diabetes and Peripheral Neuropathy," *Forefront of Medicine and Medical Care* 98 (2):399-405. English Translation.
Mirsky, I.A. et al. (1958). "The Destruction of Glucagon, Adrenocorticotropin and Somatotropin by Human Blood Plasma," *J. Clin. Invest.* 28:14-20.
Siconolfi, L.B. et al. (Jun. 15, 2001). "Mice Lacking tPA, uPA, or Plasminogen Genes Showed Delayed Functional Recovery after Sciatic Nerve Crush," *J Neurosci.* 21(12):4348-4355.
Sima, J. et al. (Apr. 23, 2004, e-pub. Mar. 23, 2004). "The Effect of Angiostatin on Vascular Leakage and VEGF Expression in Rat Retina," *FEBS Letters* 564(1-2):19-23.
Zou, T. et al. (Jan. 2006). "Exogenous Tissue Plasminogen Activator Enhances Peripheral Nerve Regeneration and Functional Recovery After Injury in Mice," *J. Neuropathol. Exp. Neurol.* 65(1):78-86.
Aisina, R.B. et al. (2014). "Structure and Function of Plasminogen/Plasmin System," *Russian Journal of Bioorganic Chemistry* 40(6):590-604.
Gao, G. et al. (Apr. 2002). "Difference in Ischemic Regulation of Vascular Endothelial Growth Factor and Pigment Epithelium-Derived Factor in Brown Norway and Sprague Dawley Rats Contributing to Difference Susceptibilities to Retinal Neovascularization," *Diabetes* 51:1218-1225.
Hou, X. (Dec. 31, 2012). "Effect of Type 2 Diabetes Insulin Pump Therapy on Glucose and Lipid Metabolism and Plasminogen," *Journal of Heze Medical College* 24(1):21-22. English Abstract.
Kenichi, M. et al. (Aug. 31, 2004). "Renal Synthesis of Urokinase Type-Plasminogen Activator, Its Receptor, and Plasminogen Activator, Its Receptor, and Plasminogen Activator Inhibitor-1in Diabetic Nephropathy in Rats: Modulation by Angiotensin-Converting-Enzyme Inhibitor," *Journal of Laboratory and Clinical Medicine* 144(2):69-77.
Liu, C. et al. (Jul. 31, 2012). "Comparision of the Affect of Gumepiride and Metformin on Fibrinolytic Function in Patients With Newly Diagnosed Type 2 Diabetes Mellitus," *Modem Hospital* 12:8-9. English Abstract.
Nicholas, SB, et al. (Apr. 30, 2005). "Plasminogen Activator Inhibitor-1 Deficiency Retards Diabetic Nephropathy," *Kidney International* 67(4):1297-1307.
Polat, S.B. et al. (Dec. 31, 2014). "Evaluation of Serum Fibrinogen, Plasminogen, α2-Anti-Plasmin, and Plasminogen Activator Inhibitor Levels (PAI) and Their Correlation with Presence of Retinopathy in Patients with Type 1 DM," *Journal of Diabetes Research* 2014(317292):1-6.
Yan, X.-F. et al. (Nov. 30, 2013). "Beta Cell Function in Relation to Plasminogen Activator Inhibitor-1 and Tissue-Plasminogen Activator in Postmenopausal Females With Different Glucose Tolerance," *Chin J Hypertens* 21 (11):1045-1048. English Abstract.
Zhang, Y. et al. (Mar. 20, 2008). "Relationship Between Fibrinolysis Change and Insulin Resistance in Type 2 Diabetes Mellitus With Microangiopathy," *Clinical Focus*, 23(6):397-399. English Abstract.
Gattinoni, L. et a. (May 2006). "Adoptive Immunotherapy for Cancer," *The Journal of Immunology* 6(5):383-393.
Li, J. et al. (Mar. 2005). "The Plasminogen Activator/Plasmin System is Essential for Development of the Joint Inflammatory Phase of Collagen Type II-Induced Arthritis," *American Journal of Pathology* 166(3):783-792.
Shaw, M.A. et al. (Apr. 5, 2017, e-pub. Mar. 8, 2017). "Plasminogen Deficiency Delays the Onset and Protects From Demyelination and Paralysis in Autoimmune Neuroinflammatory Disease," *Journal of Neuroscience* 37 (14):3776-3788.

(56) References Cited

OTHER PUBLICATIONS

Sun, Y. et al. (2010). "Advancement on Thrombolytic Characteristic, Function and Clinical Application of Different Fibrinolytic Enzyemes," China Journal of Chinese Materia Medica 35(6):794-798. English Abstract.

* cited by examiner

SEQUENCE LISTING

```
<160> NUMBER OF SEQ ID NOS: 14

<210> SEQ ID NO 1
<211> LENGTH: 2376
<212> TYPE: DNA
<213> ORGANISM: Artificial Sequence
<220> FEATURE:
<223> OTHER INFORMATION: nucleotide sequence coding for the natural
      human plasminogen (Glu-PLG or Glu-plasminogen) without the signal
      peptide

<400> SEQUENCE: 1
gagcctctgg atgactatgt gaatacccag ggggcttcac tgttcagtgt cactaagaag      60
cagctgggag caggaagtat agaagaatgt gcagcaaaat gtgaggagga cgaagaattc     120
acctgcaggg cattccaata tcacagtaaa gagcaacaat gtgtgataat ggctgaaaac     180
aggaagtcct ccataatcat taggatgaga gatgtagttt tatttgaaaa gaaagtgtat     240
ctctcagagt gcaagactgg gaatggaaag aactacagag ggacgatgtc caaaacaaaa     300
aatggcatca cctgtcaaaa atggagttcc acttctcccc acagacctag attctcacct     360
gctacacacc cctcagaggg actggaggag aactactgca ggaatccaga caacgatccg     420
caggggccct ggtgctatac tactgatcca gaaaagagat atgactactg cgacattctt     480
gagtgtgaag aggaatgtat gcattgcagt ggagaaaact atgacggcaa aatttccaag     540
accatgtctg gactggaatg ccaggcctgg gactctcaga gcccacacgc tcatggatac     600
attccttcca aatttccaaa caagaacctg aagaagaatt actgtcgtaa ccccgatagg     660
gagctgcggc cttggtgttt caccaccgac cccaacaagc gctgggaact ttgtgacatc     720
ccccgctgca acacctcc   accatcttct ggtccacct   accagtgtct gaagggaaca     780
ggtgaaaact atcgcgggaa tgtggctgtt accgtgtccg ggcacacctg tcagcactgg     840
agtgcacaga cccctcacac acataacagg acaccagaaa acttcccctg caaaaatttg     900
gatgaaaact actgccgcaa tcctgacgga aaaagggccc catggtgcca tacaaccaac     960
agccaagtgc ggtgggagta ctgtaagata ccgtcctgtg actcctcccc agtatccacg    1020
```

```
gaacaattgg ctcccacagc accacctgag ctaaccccctg tggtccagga ctgctaccat    1080
ggtgatggac agagctaccg aggcacatcc tccaccacca ccacaggaaa gaagtgtcag    1140
tcttggtcat ctatgacacc acaccggcac agaagaccc  agaaaacta cccaaatgct    1200 ggcctgacaa tgaactactg caggaatcca gatgccgata aaggcccctg gtgttttacc    1260
acagacccca gcgtcaggtg ggagtactgc aacctgaaaa aatgctcagg aacagaagcg    1320
agtgttgtag cacctccgcc tgttgtcctg cttccagatg tagagactcc ttccgaagaa    1380
gactgtatgt ttgggaatgg gaaaggatac cgaggcaaga gggcgaccac tgttactggg    1440
acgccatgcc aggactgggc tgcccaggag ccccatagac acagcatttt cactccagag    1500
acaaatccac gggcgggtct ggaaaaaaat tactgccgta accctgatgg tgatgtaggt    1560
ggtccctggt gctacacgac aaatccaaga aaactttacg actactgtga tgtccctcag    1620
tgtgcggccc cttcatttga ttgtgggaag cctcaagtgg agccgaagaa atgtcctgga    1680
agggttgtag gggggtgtgt ggcccaccca cattcctggc cctggcaagt cagtcttaga    1740
acaaggtttg gaatgcactt ctgtggaggc accttgatat ccccagagtg ggtgttgact    1800
gctgcccact gcttggagaa gtcccccaagg ccttcatcct acaaggtcat cctgggtgca    1860
caccaagaag tgaatctcga accgcatgtt caggaaatag aagtgtctag gctgttcttg    1920
gagcccacac gaaaagatat tgccttgcta aagctaagca gtcctgccgt catcactgac    1980
aaagtaatcc cagcttgtct gccatcccca aattatgtgg tcgctgaccg gaccgaatgt    2040
ttcatcactg gctggggaga aacccaaggt actttggag  ctggccttct caaggaagcc    2100
cagctccctg tgattgagaa taaagtgtgc aatcgctatg agtttctgaa tggaagagtc    2160
caatccaccg aactctgtgc tgggcatttg gccggaggca ctgacagttg ccagggtgac    2220
agtggaggtc ctctggtttg cttcgagaag gacaaataca ttttacaagg agtcacttct    2280
tggggtcttg gctgtgcacg cccccaataag cctggtgtct atgttcgtgt ttcaaggttt    2340
gttacttgga ttgagggagt gatgagaaat aattaa                              2376
```

<210> SEQ ID NO 2
<211> LENGTH: 791
<212> TYPE: PRT
<213> ORGANISM: Artificial Sequence
<220> FEATURE:
<223> OTHER INFORMATION: amino acid sequence of the natural human
      plasminogen (Glu-PLG or Glu-plasminogen) without the signal
      peptide

<400> SEQUENCE: 2

```
Glu Pro Leu Asp Asp Tyr Val Asn Thr Gln Gly Ala Ser Leu Phe Ser
1               5                   10                  15

Val Thr Lys Lys Gln Leu Gly Ala Gly Ser Ile Glu Glu Cys Ala Ala
            20                  25                  30

Lys Cys Glu Glu Asp Glu Glu Phe Thr Cys Arg Ala Phe Gln Tyr His
        35                  40                  45

Ser Lys Glu Gln Gln Cys Val Ile Met Ala Glu Asn Arg Lys Ser Ser
    50                  55                  60

Ile Ile Ile Arg Met Arg Asp Val Val Leu Phe Glu Lys Lys Val Tyr
65                  70                  75                  80

Leu Ser Glu Cys Lys Thr Gly Asn Gly Lys Asn Tyr Arg Gly Thr Met
                85                  90                  95

Ser Lys Thr Lys Asn Gly Ile Thr Cys Gln Lys Trp Ser Ser Thr Ser
            100                 105                 110
```

```
Pro His Arg Pro Arg Phe Ser Pro Ala Thr His Pro Ser Glu Gly Leu
            115                 120                 125

Glu Glu Asn Tyr Cys Arg Asn Pro Asp Asn Asp Pro Gln Gly Pro Trp
130                 135                 140

Cys Tyr Thr Thr Asp Pro Glu Lys Arg Tyr Asp Tyr Cys Asp Ile Leu
145                 150                 155                 160

Glu Cys Glu Glu Glu Cys Met His Cys Ser Gly Glu Asn Tyr Asp Gly
                165                 170                 175

Lys Ile Ser Lys Thr Met Ser Gly Leu Glu Cys Gln Ala Trp Asp Ser
            180                 185                 190

Gln Ser Pro His Ala His Gly Tyr Ile Pro Ser Lys Phe Pro Asn Lys
        195                 200                 205

Asn Leu Lys Lys Asn Tyr Cys Arg Asn Pro Asp Arg Glu Leu Arg Pro
210                 215                 220

Trp Cys Phe Thr Thr Asp Pro Asn Lys Arg Trp Glu Leu Cys Asp Ile
225                 230                 235                 240

Pro Arg Cys Thr Thr Pro Pro Ser Ser Gly Pro Thr Tyr Gln Cys
                245                 250                 255

Leu Lys Gly Thr Gly Glu Asn Tyr Arg Gly Asn Val Ala Val Thr Val
            260                 265                 270

Ser Gly His Thr Cys Gln His Trp Ser Ala Gln Thr Pro His Thr His
        275                 280                 285

Asn Arg Thr Pro Glu Asn Phe Pro Cys Lys Asn Leu Asp Glu Asn Tyr
290                 295                 300

Cys Arg Asn Pro Asp Gly Lys Arg Ala Pro Trp Cys His Thr Thr Asn
305                 310                 315                 320

Ser Gln Val Arg Trp Glu Tyr Cys Lys Ile Pro Ser Cys Asp Ser Ser
                325                 330                 335

Pro Val Ser Thr Glu Gln Leu Ala Pro Thr Ala Pro Pro Glu Leu Thr
            340                 345                 350

Pro Val Val Gln Asp Cys Tyr His Gly Asp Gly Gln Ser Tyr Arg Gly
        355                 360                 365

Thr Ser Ser Thr Thr Thr Thr Gly Lys Lys Cys Gln Ser Trp Ser Ser
370                 375                 380

Met Thr Pro His Arg His Gln Lys Thr Pro Glu Asn Tyr Pro Asn Ala
385                 390                 395                 400

Gly Leu Thr Met Asn Tyr Cys Arg Asn Pro Asp Ala Asp Lys Gly Pro
                405                 410                 415

Trp Cys Phe Thr Thr Asp Pro Ser Val Arg Trp Glu Tyr Cys Asn Leu
            420                 425                 430

Lys Lys Cys Ser Gly Thr Glu Ala Ser Val Val Ala Pro Pro Val
        435                 440                 445

Val Leu Leu Pro Asp Val Glu Thr Pro Ser Glu Glu Asp Cys Met Phe
450                 455                 460

Gly Asn Gly Lys Gly Tyr Arg Gly Lys Arg Ala Thr Thr Val Thr Gly
465                 470                 475                 480

Thr Pro Cys Gln Asp Trp Ala Ala Gln Glu Pro His Arg His Ser Ile
                485                 490                 495

Phe Thr Pro Glu Thr Asn Pro Arg Ala Gly Leu Glu Lys Asn Tyr Cys
            500                 505                 510

Arg Asn Pro Asp Gly Asp Val Gly Gly Pro Trp Cys Tyr Thr Thr Asn
        515                 520                 525
```

| | | | | | | | | | | | |
|---|---|---|---|---|---|---|---|---|---|---|---|
| Pro | Arg | Lys | Leu | Tyr | Asp | Tyr | Cys | Asp | Val | Pro | Gln | Cys | Ala | Ala | Pro |
| | 530 | | | | 535 | | | | | 540 | |

Pro Arg Lys Leu Tyr Asp Tyr Cys Asp Val Pro Gln Cys Ala Ala Pro
        530                 535                 540

Ser Phe Asp Cys Gly Lys Pro Gln Val Glu Pro Lys Lys Cys Pro Gly
545                 550                 555                 560

Arg Val Val Gly Gly Cys Val Ala His Pro His Ser Trp Pro Trp Gln
                565                 570                 575

Val Ser Leu Arg Thr Arg Phe Gly Met His Phe Cys Gly Gly Thr Leu
            580                 585                 590

Ile Ser Pro Glu Trp Val Leu Thr Ala Ala His Cys Leu Glu Lys Ser
        595                 600                 605

Pro Arg Pro Ser Ser Tyr Lys Val Ile Leu Gly Ala His Gln Glu Val
    610                 615                 620

Asn Leu Glu Pro His Val Gln Glu Ile Glu Val Ser Arg Leu Phe Leu
625                 630                 635                 640

Glu Pro Thr Arg Lys Asp Ile Ala Leu Leu Lys Leu Ser Ser Pro Ala
                645                 650                 655

Val Ile Thr Asp Lys Val Ile Pro Ala Cys Leu Pro Ser Pro Asn Tyr
            660                 665                 670

Val Val Ala Asp Arg Thr Glu Cys Phe Ile Thr Gly Trp Gly Glu Thr
        675                 680                 685

Gln Gly Thr Phe Gly Ala Gly Leu Leu Lys Glu Ala Gln Leu Pro Val
    690                 695                 700

Ile Glu Asn Lys Val Cys Asn Arg Tyr Glu Phe Leu Asn Gly Arg Val
705                 710                 715                 720

Gln Ser Thr Glu Leu Cys Ala Gly His Leu Ala Gly Gly Thr Asp Ser
                725                 730                 735

Cys Gln Gly Asp Ser Gly Gly Pro Leu Val Cys Phe Glu Lys Asp Lys
            740                 745                 750

Tyr Ile Leu Gln Gly Val Thr Ser Trp Gly Leu Gly Cys Ala Arg Pro
        755                 760                 765

Asn Lys Pro Gly Val Tyr Val Arg Val Ser Arg Phe Val Thr Trp Ile
    770                 775                 780

Glu Gly Val Met Arg Asn Asn
785                 790

<210> SEQ ID NO 3
<211> LENGTH: 2433
<212> TYPE: DNA
<213> ORGANISM: Artificial Sequence
<220> FEATURE:
<223> OTHER INFORMATION: nucleotide sequence coding for the natural
      plasminogen (from swiss prot) with the signal peptide

<400> SEQUENCE: 3
atggaacata aggaagtggt tcttctactt cttttatttc tgaaatcagg tcaaggagag      60
cctctggatg actatgtgaa tacccagggg gcttcactgt tcagtgtcac taagaagcag     120
ctgggagcag aagtataga agaatgtgca gcaaaatgtg aggaggacga agaattcacc      180
tgcagggcat ccaatatca cagtaaagag caacaatgtg tgataatggc tgaaaacagg     240
aagtcctcca taatcattag gatgagagat gtagttttat ttgaaaagaa agtgtatctc     300
tcagagtgca agactgggaa tggaaagaac tacagaggga cgatgtccaa aacaaaaaat     360
ggcatcacct gtcaaaaatg gagttccact ctctccccaca gacctagatt ctcacctgct     420

| | |
|---|---|
| acacacccct cagagggact ggaggagaac tactgcagga atccagacaa cgatccgcag | 480 |
| gggccctggt gctatactac tgatccagaa aagagatatg actactgcga cattcttgag | 540 |
| tgtgaagagg aatgtatgca ttgcagtgga gaaaactatg acggcaaaat ttccaagacc | 600 |
| atgtctggac tggaatgcca ggcctggac tctcagagcc cacacgctca tggatacatt | 660 |
| ccttccaaat ttccaaacaa gaacctgaag aagaattact gtcgtaaccc cgatagggag | 720 |
| ctgcggcctt ggtgtttcac caccgacccc aacaagcgct gggaactttg tgacatcccc | 780 |
| cgctgcacaa cacctccacc atcttctggt cccacctacc agtgtctgaa gggaacaggt | 840 |
| gaaaactatc gcgggaatgt ggctgttacc gtgtccgggc acacctgtca gcactggagt | 900 |
| gcacagaccc ctcacacaca taacaggaca ccagaaaact tccctgcaa aaatttggat | 960 |
| gaaaactact gccgcaatcc tgacggaaaa agggcccat ggtgccatac aaccaacagc | 1020 |
| caagtgcggt gggagtactg taagataccg tcctgtgact cctccccagt atccacggaa | 1080 |
| caattggctc ccacagcacc acctgagcta accctgtgg tccaggactg ctaccatggt | 1140 |
| gatggacaga gctaccgagg cacatcctcc accaccacca caggaaagaa gtgtcagtct | 1200 |
| tggtcatcta tgcacaccaca ccggcaccag aagaccccag aaaactaccc aaatgctggc | 1260 |
| ctgacaatga actactgcag gaatccagat gccgataaag cccctggtg ttttaccaca | 1320 |
| gaccccagcg tcaggtggga gtactgcaac ctgaaaaaat gctcaggaac agaagcgagt | 1380 |
| gttgtagcac ctccgcctgt tgtcctgctt ccagatgtag agactccttc cgaagaagac | 1440 |
| tgtatgtttg ggatgggaa aggataccga ggcaagaggg cgaccactgt tactgggacg | 1500 |
| ccatgccagg actgggctgc ccaggagccc catagacaca gcattttcac tccagagaca | 1560 |
| aatccacggg cgggtctgga aaaaaattac tgccgtaacc ctgatggtga tgtaggtggt | 1620 |
| ccctggtgct acgacaaa tccaagaaaa ctttacgact actgtgatgt ccctcagtgt | 1680 |
| gcggccctt catttgattg tgggaagcct caagtggagc cgaagaaatg tcctggaagg | 1740 |
| gttgtagggg ggtgtgtggc ccacccacat tcctggccct ggcaagtcag tcttagaaca | 1800 |
| aggtttggaa tgcacttctg tggaggcacc ttgatatccc cagagtgggt gttgactgct | 1860 |
| gcccactgct tggagaagtc cccaaggcct tcatcctaca aggtcatcct gggtgcacac | 1920 |
| caagaagtga atctcgaacc gcatgttcag gaaatagaag tgtctaggct gttcttggag | 1980 |
| cccacacgaa aagatattgc cttgctaaag ctaagcagtc ctgccgtcat cactgacaaa | 2040 |
| gtaatcccag cttgtctgcc atccccaaat tatgtggtcg ctgaccggac cgaatgtttc | 2100 |
| atcactggct ggggagaaac ccaaggtact tttggagctg gccttctcaa ggaagcccag | 2160 |
| ctccctgtga ttgagaataa agtgtgcaat cgctatgagt ttctgaatgg aagagtccaa | 2220 |
| tccaccgaac tctgtgctgg gcatttggcc ggaggcactg acagttgcca gggtgacagt | 2280 |
| ggaggtcctc tggtttgctt cgagaaggac aaatacattt tacaaggagt cacttcttgg | 2340 |
| ggtcttggct gtgcacgccc caataagcct ggtgtctatg ttcgtgtttc aaggtttgtt | 2400 |
| acttggattg agggagtgat gagaaataat taa | 2433 |

<210> SEQ ID NO 4
<211> LENGTH: 810
<212> TYPE: PRT
<213> ORGANISM: Artificial Sequence
<220> FEATURE:
<223> OTHER INFORMATION: amino acid sequence coding for the natural
      plasminogen (from swiss prot) with the signal peptide -continued

<400> SEQUENCE: 4

```
Met Glu His Lys Glu Val Val Leu Leu Leu Leu Phe Leu Lys Ser
1               5                  10                  15

Gly Gln Gly Glu Pro Leu Asp Asp Tyr Val Asn Thr Gln Gly Ala Ser
            20                  25                  30

Leu Phe Ser Val Thr Lys Lys Gln Leu Gly Ala Gly Ser Ile Glu Glu
        35                  40                  45

Cys Ala Ala Lys Cys Glu Glu Asp Glu Glu Phe Thr Cys Arg Ala Phe
    50                  55                  60

Gln Tyr His Ser Lys Glu Gln Gln Cys Val Ile Met Ala Glu Asn Arg
65                  70                  75                  80

Lys Ser Ser Ile Ile Ile Arg Met Arg Asp Val Val Leu Phe Glu Lys
                85                  90                  95

Lys Val Tyr Leu Ser Glu Cys Lys Thr Gly Asn Gly Lys Asn Tyr Arg
            100                 105                 110

Gly Thr Met Ser Lys Thr Lys Asn Gly Ile Thr Cys Gln Lys Trp Ser
        115                 120                 125

Ser Thr Ser Pro His Arg Pro Arg Phe Ser Pro Ala Thr His Pro Ser
    130                 135                 140

Glu Gly Leu Glu Glu Asn Tyr Cys Arg Asn Pro Asp Asn Asp Pro Gln
145                 150                 155                 160

Gly Pro Trp Cys Tyr Thr Thr Asp Pro Glu Lys Arg Tyr Asp Tyr Cys
                165                 170                 175

Asp Ile Leu Glu Cys Glu Glu Cys Met His Cys Ser Gly Glu Asn
            180                 185                 190

Tyr Asp Gly Lys Ile Ser Lys Thr Met Ser Gly Leu Glu Cys Gln Ala
        195                 200                 205

Trp Asp Ser Gln Ser Pro His Ala His Gly Tyr Ile Pro Ser Lys Phe
    210                 215                 220

Pro Asn Lys Asn Leu Lys Lys Asn Tyr Cys Arg Asn Pro Asp Arg Glu
225                 230                 235                 240

Leu Arg Pro Trp Cys Phe Thr Thr Asp Pro Asn Lys Arg Trp Glu Leu
                245                 250                 255

Cys Asp Ile Pro Arg Cys Thr Thr Pro Pro Ser Ser Gly Pro Thr
            260                 265                 270

Tyr Gln Cys Leu Lys Gly Thr Gly Glu Asn Tyr Arg Gly Asn Val Ala
        275                 280                 285

Val Thr Val Ser Gly His Thr Cys Gln His Trp Ser Ala Gln Thr Pro
    290                 295                 300

His Thr His Asn Arg Thr Pro Glu Asn Phe Pro Cys Lys Asn Leu Asp
305                 310                 315                 320

Glu Asn Tyr Cys Arg Asn Pro Asp Gly Lys Arg Ala Pro Trp Cys His
                325                 330                 335

Thr Thr Asn Ser Gln Val Arg Trp Glu Tyr Cys Lys Ile Pro Ser Cys
            340                 345                 350

Asp Ser Ser Pro Val Ser Thr Glu Gln Leu Ala Pro Thr Ala Pro Pro
        355                 360                 365

Glu Leu Thr Pro Val Val Gln Asp Cys Tyr His Gly Asp Gly Gln Ser
    370                 375                 380

Tyr Arg Gly Thr Ser Ser Thr Thr Thr Gly Lys Lys Cys Gln Ser
385                 390                 395                 400

Trp Ser Ser Met Thr Pro His Arg His Gln Lys Thr Pro Glu Asn Tyr
                405                 410                 415
```

```
Pro Asn Ala Gly Leu Thr Met Asn Tyr Cys Arg Asn Pro Asp Ala Asp
            420                 425                 430

Lys Gly Pro Trp Cys Phe Thr Thr Asp Pro Ser Val Arg Trp Glu Tyr
        435                 440                 445

Cys Asn Leu Lys Lys Cys Ser Gly Thr Glu Ala Ser Val Val Ala Pro
    450                 455                 460

Pro Pro Val Val Leu Leu Pro Asp Val Glu Thr Pro Ser Glu Glu Asp
465                 470                 475                 480

Cys Met Phe Gly Asn Gly Lys Gly Tyr Arg Gly Lys Arg Ala Thr Thr
                485                 490                 495

Val Thr Gly Thr Pro Cys Gln Asp Trp Ala Ala Gln Glu Pro His Arg
            500                 505                 510

His Ser Ile Phe Thr Pro Glu Thr Asn Pro Arg Ala Gly Leu Glu Lys
        515                 520                 525

Asn Tyr Cys Arg Asn Pro Asp Gly Asp Val Gly Gly Pro Trp Cys Tyr
    530                 535                 540

Thr Thr Asn Pro Arg Lys Leu Tyr Asp Tyr Cys Asp Val Pro Gln Cys
545                 550                 555                 560

Ala Ala Pro Ser Phe Asp Cys Gly Lys Pro Gln Val Glu Pro Lys Lys
                565                 570                 575

Cys Pro Gly Arg Val Val Gly Gly Cys Val Ala His Pro His Ser Trp
            580                 585                 590

Pro Trp Gln Val Ser Leu Arg Thr Arg Phe Gly Met His Phe Cys Gly
        595                 600                 605

Gly Thr Leu Ile Ser Pro Glu Trp Val Leu Thr Ala Ala His Cys Leu
    610                 615                 620

Glu Lys Ser Pro Arg Pro Ser Ser Tyr Lys Val Ile Leu Gly Ala His
625                 630                 635                 640

Gln Glu Val Asn Leu Glu Pro His Val Gln Glu Ile Glu Val Ser Arg
                645                 650                 655

Leu Phe Leu Glu Pro Thr Arg Lys Asp Ile Ala Leu Leu Lys Leu Ser
            660                 665                 670

Ser Pro Ala Val Ile Thr Asp Lys Val Ile Pro Ala Cys Leu Pro Ser
        675                 680                 685

Pro Asn Tyr Val Val Ala Asp Arg Thr Glu Cys Phe Ile Thr Gly Trp
    690                 695                 700

Gly Glu Thr Gln Gly Thr Phe Gly Ala Gly Leu Leu Lys Glu Ala Gln
705                 710                 715                 720

Leu Pro Val Ile Glu Asn Lys Val Cys Asn Arg Tyr Glu Phe Leu Asn
                725                 730                 735

Gly Arg Val Gln Ser Thr Glu Leu Cys Ala Gly His Leu Ala Gly Gly
            740                 745                 750

Thr Asp Ser Cys Gln Gly Asp Ser Gly Gly Pro Leu Val Cys Phe Glu
        755                 760                 765

Lys Asp Lys Tyr Ile Leu Gln Gly Val Thr Ser Trp Gly Leu Gly Cys
    770                 775                 780

Ala Arg Pro Asn Lys Pro Gly Val Tyr Val Arg Val Ser Arg Phe Val
785                 790                 795                 800

Thr Trp Ile Glu Gly Val Met Arg Asn Asn
                805                 810
```

```
<210> SEQ ID NO 5
<211> LENGTH: 2145
<212> TYPE: DNA
<213> ORGANISM: Artificial Sequence
<220> FEATURE:
<223> OTHER INFORMATION: nucleotide sequence coding for LYS77-PLG or
      Lys-plasminogen

<400> SEQUENCE: 5
```

| | | | | | |
|---|---|---|---|---|---|
| aaagtgtatc | tctcagagtg | caagactggg | aatggaaaga | actacagagg | gacgatgtcc | 60 |
| aaaacaaaaa | atggcatcac | ctgtcaaaaa | tggagttcca | cttctcccca | cagacctaga | 120 |
| ttctcacctg | ctacacaccc | ctcagaggga | ctggaggaga | actactgcag | gaatccagac | 180 |
| aacgatccgc | aggggccctg | gtgctatact | actgatccag | aaaagagata | tgactactgc | 240 |
| gacattcttg | agtgtgaaga | ggaatgtatg | cattgcagtg | gagaaaacta | tgacggcaaa | 300 |
| atttccaaga | ccatgtctgg | actggaatgc | caggcctggg | actctcagag | cccacacgct | 360 |
| catggataca | ttccttccaa | atttccaaac | aagaacctga | agaagaatta | ctgtcgtaac | 420 |
| cccgataggg | agctgcggcc | ttggtgtttc | accaccgacc | ccaacaagcg | ctgggaactt | 480 |
| tgtgacatcc | cccgctgcac | aacacctcca | ccatcttctg | gtcccaccta | ccagtgtctg | 540 |
| aagggaacag | gtgaaaacta | cgcgggaat | gtggctgtta | ccgtgtccgg | gcacacctgt | 600 |
| cagcactgga | gtgcacagac | ccctcacaca | cataacagga | caccagaaaa | cttcccctgc | 660 |
| aaaaatttgg | atgaaaacta | ctgccgcaat | cctgacggaa | aaaggcccc | atggtgccat | 720 |
| acaaccaaca | gccaagtgcg | gtgggagtac | tgtaagatac | cgtcctgtga | ctcctcccca | 780 |
| gtatccacgg | aacaattggc | tcccacagca | ccacctgagc | taacccctgt | ggtccaggac | 840 |
| tgctaccatg | gtgatggaca | gagctaccga | ggcacatcct | ccaccaccac | cacaggaaag | 900 |
| aagtgtcagt | cttggtcatc | tatgacacca | caccggcacc | agaagacccc | agaaaactac | 960 |
| ccaaatgctg | gcctgacaat | gaactactgc | aggaatccag | atgccgataa | aggcccctgg | 1020 |
| tgttttacca | cagaccccag | cgtcaggtgg | gagtactgca | acctgaaaaa | atgctcagga | 1080 |
| acagaagcga | gtgttgtagc | acctccgcct | gttgtcctgc | ttccagatgt | agagactcct | 1140 |
| tccgaagaag | actgtatgtt | tgggaatggg | aaaggatacc | gaggcaagag | ggcgaccact | 1200 |
| gttactggga | cgccatgcca | ggactgggct | gcccaggagc | ccatagaca | cagcattttc | 1260 |
| actccagaga | caaatccacg | ggcgggtctg | gaaaaaaatt | actgccgtaa | ccctgatggt | 1320 |
| gatgtaggtg | gtccctggtg | ctacacgaca | aatccaagaa | aactttacga | ctactgtgat | 1380 |
| gtccctcagt | gtgcggcccc | ttcatttgat | tgtgggaagc | ctcaagtgga | gccgaagaaa | 1440 |
| tgtcctggaa | gggttgtagg | ggggtgtgtg | gcccacccac | attcctggcc | ctggcaagtc | 1500 |
| agtcttagaa | caaggtttgg | aatgcacttc | tgtggaggca | ccttgatatc | cccagagtgg | 1560 |
| gtgttgactg | ctgcccactg | cttggagaag | tccccaaggc | cttcatccta | caaggtcatc | 1620 |
| ctgggtgcac | accaagaagt | gaatctcgaa | ccgcatgttc | aggaaataga | agtgtctagg | 1680 |
| ctgttcttgg | agcccacacg | aaaagatatt | gccttgctaa | agctaagcag | tcctgccgtc | 1740 |
| atcactgaca | aagtaatccc | agcttgtctg | ccatccccaa | attatgtggt | cgctgaccgg | 1800 |
| accgaatgtt | tcatcactgg | ctggggagaa | acccaaggta | cttttggagc | tggccttctc | 1860 |
| aaggaagccc | agctccctgt | gattgagaat | aaagtgtgca | atcgctatga | gtttctgaat | 1920 |
| ggaagagtcc | aatccaccga | actctgtgct | gggcatttgg | ccggaggcac | tgacagttgc | 1980 |
| cagggtgaca | gtggaggtcc | tctggtttgc | ttcgagaagg | acaaatacat | tttacaagga | 2040 |

```
gtcacttctt ggggtcttgg ctgtgcacgc cccaataagc ctggtgtcta tgttcgtgtt      2100
tcaaggtttg ttacttggat tgagggagtg atgagaaata attaa                      2145
```

<210> SEQ ID NO 6
<211> LENGTH: 714
<212> TYPE: PRT
<213> ORGANISM: Artificial Sequence
<220> FEATURE:
<223> OTHER INFORMATION: amino acid sequence of LYS77-PLG or
      Lys-plasminogen

<400> SEQUENCE: 6

```
Lys Val Tyr Leu Ser Glu Cys Lys Thr Gly Asn Gly Lys Asn Tyr Arg
1               5                   10                  15

Gly Thr Met Ser Lys Thr Lys Asn Gly Ile Thr Cys Gln Lys Trp Ser
            20                  25                  30

Ser Thr Ser Pro His Arg Pro Arg Phe Ser Pro Ala Thr His Pro Ser
        35                  40                  45

Glu Gly Leu Glu Glu Asn Tyr Cys Arg Asn Pro Asp Asn Asp Pro Gln
    50                  55                  60

Gly Pro Trp Cys Tyr Thr Thr Asp Pro Glu Lys Arg Tyr Asp Tyr Cys
65                  70                  75                  80

Asp Ile Leu Glu Cys Glu Glu Glu Cys Met His Cys Ser Gly Glu Asn
                85                  90                  95

Tyr Asp Gly Lys Ile Ser Lys Thr Met Ser Gly Leu Glu Cys Gln Ala
            100                 105                 110

Trp Asp Ser Gln Ser Pro His Ala His Gly Tyr Ile Pro Ser Lys Phe
        115                 120                 125

Pro Asn Lys Asn Leu Lys Lys Asn Tyr Cys Arg Asn Pro Asp Arg Glu
    130                 135                 140

Leu Arg Pro Trp Cys Phe Thr Thr Asp Pro Asn Lys Arg Trp Glu Leu
145                 150                 155                 160

Cys Asp Ile Pro Arg Cys Thr Thr Pro Pro Pro Ser Ser Gly Pro Thr
                165                 170                 175

Tyr Gln Cys Leu Lys Gly Thr Gly Glu Asn Tyr Arg Gly Asn Val Ala
            180                 185                 190

Val Thr Val Ser Gly His Thr Cys Gln His Trp Ser Ala Gln Thr Pro
        195                 200                 205

His Thr His Asn Arg Thr Pro Glu Asn Phe Pro Cys Lys Asn Leu Asp
    210                 215                 220

Glu Asn Tyr Cys Arg Asn Pro Asp Gly Lys Arg Ala Pro Trp Cys His
225                 230                 235                 240

Thr Thr Asn Ser Gln Val Arg Trp Glu Tyr Cys Lys Ile Pro Ser Cys
                245                 250                 255

Asp Ser Ser Pro Val Ser Thr Glu Gln Leu Ala Pro Thr Ala Pro Pro
            260                 265                 270

Glu Leu Thr Pro Val Val Gln Asp Cys Tyr His Gly Asp Gly Gln Ser
        275                 280                 285

Tyr Arg Gly Thr Ser Ser Thr Thr Thr Thr Gly Lys Lys Cys Gln Ser
    290                 295                 300

Trp Ser Ser Met Thr Pro His Arg His Gln Lys Thr Pro Glu Asn Tyr
305                 310                 315                 320

Pro Asn Ala Gly Leu Thr Met Asn Tyr Cys Arg Asn Pro Asp Ala Asp
                325                 330                 335
```

```
Lys Gly Pro Trp Cys Phe Thr Thr Asp Pro Ser Val Arg Trp Glu Tyr
            340                 345                 350

Cys Asn Leu Lys Lys Cys Ser Gly Thr Glu Ala Ser Val Val Ala Pro
            355                 360                 365

Pro Pro Val Val Leu Leu Pro Asp Val Glu Thr Pro Ser Glu Glu Asp
            370                 375                 380

Cys Met Phe Gly Asn Gly Lys Gly Tyr Arg Gly Lys Arg Ala Thr Thr
385                 390                 395                 400

Val Thr Gly Thr Pro Cys Gln Asp Trp Ala Ala Gln Glu Pro His Arg
            405                 410                 415

His Ser Ile Phe Thr Pro Glu Thr Asn Pro Arg Ala Gly Leu Glu Lys
            420                 425                 430

Asn Tyr Cys Arg Asn Pro Asp Gly Asp Val Gly Gly Pro Trp Cys Tyr
            435                 440                 445

Thr Thr Asn Pro Arg Lys Leu Tyr Asp Tyr Cys Asp Val Pro Gln Cys
            450                 455                 460

Ala Ala Pro Ser Phe Asp Cys Gly Lys Pro Gln Val Glu Pro Lys Lys
465                 470                 475                 480

Cys Pro Gly Arg Val Val Gly Gly Cys Val Ala His Pro His Ser Trp
            485                 490                 495

Pro Trp Gln Val Ser Leu Arg Thr Arg Phe Gly Met His Phe Cys Gly
            500                 505                 510

Gly Thr Leu Ile Ser Pro Glu Trp Val Leu Thr Ala Ala His Cys Leu
            515                 520                 525

Glu Lys Ser Pro Arg Pro Ser Ser Tyr Lys Val Ile Leu Gly Ala His
530                 535                 540

Gln Glu Val Asn Leu Glu Pro His Val Gln Glu Ile Glu Val Ser Arg
545                 550                 555                 560

Leu Phe Leu Glu Pro Thr Arg Lys Asp Ile Ala Leu Leu Lys Leu Ser
            565                 570                 575

Ser Pro Ala Val Ile Thr Asp Lys Val Ile Pro Ala Cys Leu Pro Ser
            580                 585                 590

Pro Asn Tyr Val Val Ala Asp Arg Thr Glu Cys Phe Ile Thr Gly Trp
            595                 600                 605

Gly Glu Thr Gln Gly Thr Phe Gly Ala Gly Leu Leu Lys Glu Ala Gln
            610                 615                 620

Leu Pro Val Ile Glu Asn Lys Val Cys Asn Arg Tyr Glu Phe Leu Asn
625                 630                 635                 640

Gly Arg Val Gln Ser Thr Glu Leu Cys Ala Gly His Leu Ala Gly Gly
            645                 650                 655

Thr Asp Ser Cys Gln Gly Asp Ser Gly Gly Pro Leu Val Cys Phe Glu
            660                 665                 670

Lys Asp Lys Tyr Ile Leu Gln Gly Val Thr Ser Trp Gly Leu Gly Cys
            675                 680                 685

Ala Arg Pro Asn Lys Pro Gly Val Tyr Val Arg Val Ser Arg Phe Val
            690                 695                 700

Thr Trp Ile Glu Gly Val Met Arg Asn Asn
705                 710

<210> SEQ ID NO 7
<211> LENGTH: 1245
<212> TYPE: DNA
<213> ORGANISM: Artificial Sequence
```

-continued

<220> FEATURE:
<223> OTHER INFORMATION: nucleotide sequence coding for delta-plg or
      delta-plasminogen

<400> SEQUENCE: 7

```
gagcctctgg atgactatgt gaatacccag ggggcttcac tgttcagtgt cactaagaag      60
cagctgggag caggaagtat agaagaatgt gcagcaaaat gtgaggagga cgaagaattc     120
acctgcaggg cattccaata tcacagtaaa gagcaacaat gtgtgataat ggctgaaaac     180
aggaagtcct ccataatcat taggatgaga gatgtagttt atttgaaaaa gaaagtgtat     240
ctctcagagt gcaagactgg gaatggaaag aactacagag ggacgatgtc aaaacaaaa      300
aatggcatca cctgtcaaaa atggagttcc acttctcccc acagacctag attctcacct     360
gctacacacc cctcagaggg actggaggag aactactgca ggaatccaga caacgatccg     420
cagggggccct ggtgctatac tactgatcca gaaaagagat atgactactg cgacattctt     480
gagtgtgaag aggcggcccc ttcatttgat tgtgggaagc ctcaagtgga gccgaagaaa     540
tgtcctggaa gggttgtagg ggggtgtgtg gcccacccac attcctggcc ctggcaagtc     600
agtcttagaa caaggtttgg aatgcacttc tgtggaggca ccttgatatc cccagagtgg     660
gtgttgactg ctgcccactg cttggagaag tccccaaggc cttcatccta caaggtcatc     720
ctgggtgcac accaagaagt gaatctcgaa ccgcatgttc aggaaataga agtgtctagg     780
ctgttcttgg agcccacacg aaaagatatt gccttgctaa agctaagcag tcctgccgtc     840
atcactgaca agtaatccc agcttgtctg ccatccccaa attatgtggt cgctgaccgg     900
accgaatgtt tcatcactgg ctggggagaa acccaaggta cttttggagc tggccttctc     960
aaggaagccc agctccctgt gattgagaat aaagtgtgca atcgctatga gtttctgaat    1020
ggaagagtcc aatccaccga actctgtgct gggcatttgg ccggaggcac tgacagttgc    1080
cagggtgaca gtggaggtcc tctggtttgc ttcgagaagg acaaatacat tttacaagga    1140
gtcacttctt ggggtcttgg ctgtgcacgc cccaataagc ctggtgtcta tgttcgtgtt    1200
tcaaggtttg ttacttggat tgagggagtg atgagaaata attaa                    1245
```

<210> SEQ ID NO 8
<211> LENGTH: 414
<212> TYPE: PRT
<213> ORGANISM: Artificial Sequence
<220> FEATURE:
<223> OTHER INFORMATION: amino acid sequence of delta-plg or
      delta-plasminogen

<400> SEQUENCE: 8

```
Glu Pro Leu Asp Asp Tyr Val Asn Thr Gln Gly Ala Ser Leu Phe Ser
 1               5                  10                  15

Val Thr Lys Lys Gln Leu Gly Ala Gly Ser Ile Glu Glu Cys Ala Ala
            20                  25                  30

Lys Cys Glu Glu Asp Glu Glu Phe Thr Cys Arg Ala Phe Gln Tyr His
        35                  40                  45

Ser Lys Glu Gln Gln Cys Val Ile Met Ala Glu Asn Arg Lys Ser Ser
    50                  55                  60

Ile Ile Ile Arg Met Arg Asp Val Val Leu Phe Glu Lys Lys Val Tyr
65                  70                  75                  80

Leu Ser Glu Cys Lys Thr Gly Asn Gly Lys Asn Tyr Arg Gly Thr Met
                85                  90                  95

Ser Lys Thr Lys Asn Gly Ile Thr Cys Gln Lys Trp Ser Ser Thr Ser
            100                 105                 110
```

```
Pro His Arg Pro Arg Phe Ser Pro Ala Thr His Pro Ser Glu Gly Leu
            115                 120                 125

Glu Glu Asn Tyr Cys Arg Asn Pro Asp Asn Asp Pro Gln Gly Pro Trp
    130                 135                 140

Cys Tyr Thr Thr Asp Pro Glu Lys Arg Tyr Asp Tyr Cys Asp Ile Leu
145                 150                 155                 160

Glu Cys Glu Glu Ala Ala Pro Ser Phe Asp Cys Gly Lys Pro Gln Val
                165                 170                 175

Glu Pro Lys Lys Cys Pro Gly Arg Val Val Gly Gly Cys Val Ala His
            180                 185                 190

Pro His Ser Trp Pro Trp Gln Val Ser Leu Arg Thr Arg Phe Gly Met
        195                 200                 205

His Phe Cys Gly Gly Thr Leu Ile Ser Pro Glu Trp Val Leu Thr Ala
    210                 215                 220

Ala His Cys Leu Glu Lys Ser Pro Arg Pro Ser Ser Tyr Lys Val Ile
225                 230                 235                 240

Leu Gly Ala His Gln Glu Val Asn Leu Glu Pro His Val Gln Glu Ile
                245                 250                 255

Glu Val Ser Arg Leu Phe Leu Glu Pro Thr Arg Lys Asp Ile Ala Leu
            260                 265                 270

Leu Lys Leu Ser Ser Pro Ala Val Ile Thr Asp Lys Val Ile Pro Ala
        275                 280                 285

Cys Leu Pro Ser Pro Asn Tyr Val Val Ala Asp Arg Thr Glu Cys Phe
    290                 295                 300

Ile Thr Gly Trp Gly Glu Thr Gln Gly Thr Phe Gly Ala Gly Leu Leu
305                 310                 315                 320

Lys Glu Ala Gln Leu Pro Val Ile Glu Asn Lys Val Cys Asn Arg Tyr
                325                 330                 335

Glu Phe Leu Asn Gly Arg Val Gln Ser Thr Glu Leu Cys Ala Gly His
            340                 345                 350

Leu Ala Gly Gly Thr Asp Ser Cys Gln Gly Asp Ser Gly Gly Pro Leu
        355                 360                 365

Val Cys Phe Glu Lys Asp Lys Tyr Ile Leu Gln Gly Val Thr Ser Trp
    370                 375                 380

Gly Leu Gly Cys Ala Arg Pro Asn Lys Pro Gly Val Tyr Val Arg Val
385                 390                 395                 400

Ser Arg Phe Val Thr Trp Ile Glu Gly Val Met Arg Asn Asn
                405                 410

<210> SEQ ID NO 9
<211> LENGTH: 1104
<212> TYPE: DNA
<213> ORGANISM: Artificial Sequence
<220> FEATURE:
<223> OTHER INFORMATION: nucleotide sequence coding for Mini-plg or
      mini-plasminogen

<400> SEQUENCE: 9
gtcaggtggg agtactgcaa cctgaaaaaa tgctcaggaa cagaagcgag tgttgtagca      60
cctccgcctg ttgtcctgct tccagatgta gagactcctt ccgaagaaga ctgtatgttt     120
gggaatggga aggataccg aggcaagagg gcgaccactg ttactgggac gccatgccag      180
gactgggctg cccaggagcc ccatagacac agcattttca ctccagagac aaatccacgg     240
gcgggtctga aaaaaatta ctgccgtaac cctgatggtg atgtaggtgg tcctggtgc       300 tacacgacaa atccaagaaa actttacgac tactgtgatg tccctcagtg tgcggcccct    360
```

```
tcatttgatt gtgggaagcc tcaagtggag ccgaagaaat gtcctggaag ggttgtaggg    420
gggtgtgtgg cccacccaca ttcctggccc tggcaagtca gtcttagaac aaggtttgga    480
atgcacttct gtggaggcac cttgatatcc ccagagtggg tgttgactgc tgcccactgc    540
ttggagaagt ccccaaggcc ttcatcctac aaggtcatcc tgggtgcaca ccaagaagtg    600
aatctcgaac cgcatgttca ggaaatagaa gtgtctaggc tgttcttgga gcccacacga    660
aaagatattg ccttgctaaa gctaagcagt cctgccgtca tcactgacaa agtaatccca    720
gcttgtctgc catccccaaa ttatgtggtc gctgaccgga ccgaatgttt catcactggc    780
tggggagaaa cccaaggtac ttttggagct ggccttctca aggaagccca gctccctgtg    840
attgagaata agtgtgcaa tcgctatgag tttctgaatg aagagtcca atccaccgaa     900 ctctgtgctg gcatttggc cggaggcact gacagttgcc agggtgacag tggaggtcct    960
ctggtttgct tcgagaagga caaatacatt ttacaaggag tcacttcttg gggtcttggc    1020
tgtgcacgcc ccaataagcc tggtgtctat gttcgtgttt caaggtttgt tacttggatt    1080
gagggagtga tgagaaataa ttaa                                          1104

<210> SEQ ID NO 10
<211> LENGTH: 367
<212> TYPE: PRT
<213> ORGANISM: Artificial Sequence
<220> FEATURE:
<223> OTHER INFORMATION: amino acid sequence of Mini-plg or
      mini-plasminogen

<400> SEQUENCE: 10

Val Arg Trp Glu Tyr Cys Asn Leu Lys Lys Cys Ser Gly Thr Glu Ala
1               5                   10                  15

Ser Val Val Ala Pro Pro Val Val Leu Leu Pro Asp Val Glu Thr
            20                  25                  30

Pro Ser Glu Glu Asp Cys Met Phe Gly Asn Gly Lys Gly Tyr Arg Gly
            35                  40                  45

Lys Arg Ala Thr Thr Val Thr Gly Thr Pro Cys Gln Asp Trp Ala Ala
        50                  55                  60

Gln Glu Pro His Arg His Ser Ile Phe Thr Pro Glu Thr Asn Pro Arg
65                  70                  75                  80

Ala Gly Leu Glu Lys Asn Tyr Cys Arg Asn Pro Asp Gly Asp Val Gly
                85                  90                  95

Gly Pro Trp Cys Tyr Thr Thr Asn Pro Arg Lys Leu Tyr Asp Tyr Cys
            100                 105                 110

Asp Val Pro Gln Cys Ala Ala Pro Ser Phe Asp Cys Gly Lys Pro Gln
        115                 120                 125

Val Glu Pro Lys Lys Cys Pro Gly Arg Val Val Gly Gly Cys Val Ala
            130                 135                 140

His Pro His Ser Trp Pro Trp Gln Val Ser Leu Arg Thr Arg Phe Gly
145                 150                 155                 160

Met His Phe Cys Gly Gly Thr Leu Ile Ser Pro Glu Trp Val Leu Thr
                165                 170                 175

Ala Ala His Cys Leu Glu Lys Ser Pro Arg Pro Ser Ser Tyr Lys Val
            180                 185                 190

Ile Leu Gly Ala His Gln Glu Val Asn Leu Glu Pro His Val Gln Glu
        195                 200                 205
```

Ile Glu Val Ser Arg Leu Phe Leu Glu Pro Thr Arg Lys Asp Ile Ala
210                 215                 220

Leu Leu Lys Leu Ser Ser Pro Ala Val Ile Thr Asp Lys Val Ile Pro
225                 230                 235                 240

Ala Cys Leu Pro Ser Pro Asn Tyr Val Val Ala Asp Arg Thr Glu Cys
                245                 250                 255

Phe Ile Thr Gly Trp Gly Glu Thr Gln Gly Thr Phe Gly Ala Gly Leu
            260                 265                 270

Leu Lys Glu Ala Gln Leu Pro Val Ile Glu Asn Lys Val Cys Asn Arg
        275                 280                 285

Tyr Glu Phe Leu Asn Gly Arg Val Gln Ser Thr Glu Leu Cys Ala Gly
    290                 295                 300

His Leu Ala Gly Gly Thr Asp Ser Cys Gln Gly Asp Ser Gly Gly Pro
305                 310                 315                 320

Leu Val Cys Phe Glu Lys Asp Lys Tyr Ile Leu Gln Gly Val Thr Ser
                325                 330                 335

Trp Gly Leu Gly Cys Ala Arg Pro Asn Lys Pro Gly Val Tyr Val Arg
            340                 345                 350

Val Ser Arg Phe Val Thr Trp Ile Glu Gly Val Met Arg Asn Asn
        355                 360                 365

<210> SEQ ID NO 11
<211> LENGTH: 750
<212> TYPE: DNA
<213> ORGANISM: Artificial Sequence
<220> FEATURE:
<223> OTHER INFORMATION: nucleotide sequence coding for Micro-plg or
      micro-plasminogen

<400> SEQUENCE: 11
gccccttcat tgattgtgg gaagcctcaa gtggagccga agaaatgtcc tggaagggtt     60 gtagggggt gtgtggccca cccacattcc tggccctggc aagtcagtct tagaacaagg    120
tttggaatgc acttctgtgg aggcaccttg atatccccag agtgggtgtt gactgctgcc    180
cactgcttgg agaagtcccc aaggccttca tcctacaagg tcatcctggg tgcacaccaa    240
gaagtgaatc tcgaaccgca tgttcaggaa atagaagtgt ctaggctgtt cttggagccc    300
acacgaaaag atattgcctt gctaaagcta agcagtcctg ccgtcatcac tgacaaagta    360
atcccagctt gtctgccatc cccaaattat gtggtcgctg accggaccga atgtttcatc    420
actggctggg gagaaaccca aggtactttt ggagctggcc ttctcaagga agcccagctc    480
cctgtgattg agaataaagt gtgcaatcgc tatgagtttc tgaatggaag agtccaatcc    540
accgaactct gtgctgggca tttggccgga ggcactgaca gttgccaggg tgacagtgga    600
ggtcctctgg tttgcttcga gaaggacaaa tacattttac aaggagtcac ttcttggggt    660
cttggctgtg cacgccccaa taagcctggt gtctatgttc gtgtttcaag gtttgttact    720
tggattgagg gagtgatgag aaataattaa                                     750

<210> SEQ ID NO 12
<211> LENGTH: 249
<212> TYPE: PRT
<213> ORGANISM: Artificial Sequence
<220> FEATURE:
<223> OTHER INFORMATION: amino acid sequence coding for Micro-plg or
      micro-plasminogen

<400> SEQUENCE: 12

| | | | | | | | | | | | | | | | |
|---|---|---|---|---|---|---|---|---|---|---|---|---|---|---|---|
|Ala|Pro|Ser|Phe|Asp|Cys|Gly|Lys|Pro|Gln|Val|Glu|Pro|Lys|Lys|Cys|
|1| | | |5| | | | |10| | | | |15| |

Pro Gly Arg Val Val Gly Gly Cys Val Ala His Pro His Ser Trp Pro
            20                  25                  30

Trp Gln Val Ser Leu Arg Thr Arg Phe Gly Met His Phe Cys Gly Gly
        35                  40                  45

Thr Leu Ile Ser Pro Glu Trp Val Leu Thr Ala Ala His Cys Leu Glu
    50                  55                  60

Lys Ser Pro Arg Pro Ser Ser Tyr Lys Val Ile Leu Gly Ala His Gln
65                  70                  75                  80

Glu Val Asn Leu Glu Pro His Val Gln Glu Ile Glu Val Ser Arg Leu
                85                  90                  95

Phe Leu Glu Pro Thr Arg Lys Asp Ile Ala Leu Leu Lys Leu Ser Ser
            100                 105                 110

Pro Ala Val Ile Thr Asp Lys Val Ile Pro Ala Cys Leu Pro Ser Pro
        115                 120                 125

Asn Tyr Val Val Ala Asp Arg Thr Glu Cys Phe Ile Thr Gly Trp Gly
    130                 135                 140

Glu Thr Gln Gly Thr Phe Gly Ala Gly Leu Leu Lys Glu Ala Gln Leu
145                 150                 155                 160

Pro Val Ile Glu Asn Lys Val Cys Asn Arg Tyr Glu Phe Leu Asn Gly
                165                 170                 175

Arg Val Gln Ser Thr Glu Leu Cys Ala Gly His Leu Ala Gly Gly Thr
            180                 185                 190

Asp Ser Cys Gln Gly Asp Ser Gly Gly Pro Leu Val Cys Phe Glu Lys
        195                 200                 205

Asp Lys Tyr Ile Leu Gln Gly Val Thr Ser Trp Gly Leu Gly Cys Ala
    210                 215                 220

Arg Pro Asn Lys Pro Gly Val Tyr Val Arg Val Ser Arg Phe Val Thr
225                 230                 235                 240

Trp Ile Glu Gly Val Met Arg Asn Asn
                245

<210> SEQ ID NO 13
<211> LENGTH: 684
<212> TYPE: DNA
<213> ORGANISM: Artificial Sequence
<220> FEATURE:
<223> OTHER INFORMATION: nucleotide sequence coding for the serine
      protease domain

<400> SEQUENCE: 13

```
gttgtagggg ggtgtgtggc ccacccacat tcctggccct ggcaagtcag tcttagaaca     60
aggtttggaa tgcacttctg tggaggcacc ttgatatccc cagagtgggt gttgactgct    120
gcccactgct tggagaagtc cccaaggcct tcatcctaca aggtcatcct gggtgcacac    180
caagaagtga atctcgaacc gcatgttcag gaaatagaag tgtctaggct gttcttggag    240
cccacacgaa aagatattgc cttgctaaag ctaagcagtc ctgccgtcat cactgacaaa    300
gtaatcccag cttgtctgcc atccccaaat tatgtggtcg ctgaccggac cgaatgtttc    360
atcactggct ggggagaaac ccaaggtact tttggagctg gccttctcaa ggaagcccag    420
ctccctgtga ttgagaataa agtgtgcaat cgctatgagt tcctgaatgg aagagtccaa    480
tccaccgaac tctgtgctgg gcatttggcc ggaggcactg acagttgcca gggtgacagt    540
```

```
ggaggtcctc tggtttgctt cgagaaggac aaatacattt tacaaggagt cacttcttgg    600
ggtcttggct gtgcacgccc caataagcct ggtgtctatg ttcgtgtttc aaggtttgtt    660
acttggattg agggagtgat gaga                                           684
```

<210> SEQ ID NO 14
<211> LENGTH: 228
<212> TYPE: PRT
<213> ORGANISM: Artificial Sequence
<220> FEATURE:
<223> OTHER INFORMATION: amino acid sequence coding for the serine
      protease domain

<400> SEQUENCE: 14

```
Val Val Gly Gly Cys Val Ala His Pro His Ser Trp Pro Trp Gln Val
1               5                   10                  15

Ser Leu Arg Thr Arg Phe Gly Met His Phe Cys Gly Gly Thr Leu Ile
            20                  25                  30

Ser Pro Glu Trp Val Leu Thr Ala Ala His Cys Leu Glu Lys Ser Pro
        35                  40                  45

Arg Pro Ser Ser Tyr Lys Val Ile Leu Gly Ala His Gln Glu Val Asn
    50                  55                  60

Leu Glu Pro His Val Gln Glu Ile Glu Val Ser Arg Leu Phe Leu Glu
65                  70                  75                  80

Pro Thr Arg Lys Asp Ile Ala Leu Leu Lys Leu Ser Ser Pro Ala Val
                85                  90                  95

Ile Thr Asp Lys Val Ile Pro Ala Cys Leu Pro Ser Pro Asn Tyr Val
            100                 105                 110

Val Ala Asp Arg Thr Glu Cys Phe Ile Thr Gly Trp Gly Glu Thr Gln
        115                 120                 125

Gly Thr Phe Gly Ala Gly Leu Leu Lys Glu Ala Gln Leu Pro Val Ile
    130                 135                 140

Glu Asn Lys Val Cys Asn Arg Tyr Glu Phe Leu Asn Gly Arg Val Gln
145                 150                 155                 160

Ser Thr Glu Leu Cys Ala Gly His Leu Ala Gly Gly Thr Asp Ser Cys
                165                 170                 175

Gln Gly Asp Ser Gly Gly Pro Leu Val Cys Phe Glu Lys Asp Lys Tyr
            180                 185                 190

Ile Leu Gln Gly Val Thr Ser Trp Gly Leu Gly Cys Ala Arg Pro Asn
        195                 200                 205

Lys Pro Gly Val Tyr Val Arg Val Ser Arg Phe Val Thr Trp Ile Glu
    210                 215                 220

Gly Val Met Arg
225
```

METHOD OF TREATING DIABETIC NEPHROPATHY COMPRISING ADMINISTERING PLASMINOGEN

CROSS REFERENCE TO RELATED APPLICATIONS

This application is a National Phase application under 35 U.S.C. § 371 of International Application No. PCT/CN2016/110450, filed Dec. 16, 2016, which claims priority to International Application No. PCT/CN2015/097944, filed Dec. 18, 2015, the contents of each of which are incorporated herein by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 794922000200SEQLIST.TXT, date recorded: Jun. 10, 2018, size: 46 KB).

TECHNICAL FIELD

The present invention relates to the effect of plasminogen in the prevention, treatment and/or elimination of nephropathy caused by diabetes mellitus, thereby providing a brand new therapeutic strategy for treating different types of diabetic nephropathy and its related disorders.

BACKGROUND ART

Diabetes mellitus is a chronic disease with disordered metabolisms of carbohydrates, fats and proteins caused by relatively or absolutely insufficient insulin in the body or decreased sensitivity of target cells to insulin, or structural defects in insulin itself[1]. Diabetic nephropathy (DN) is one of the major complications of diabetes mellitus, and about 20%-40% of diabetics may develop DN[2-4]. Diabetic nephropathy is the most common and frequently occurring complication of diabetes mellitus clinically, manifested as hypertension, proteinuria, edema, renal insufficiency, etc., which are mainly due to glomerular sclerosis caused by the abnormal metabolism of diabetes mellitus, resulting in renal dysfunction and damage[5, 6]. Diabetic nephropathy is manifested as glomerular hypertrophy, glomerular basement membrane thickening and mesangial matrix widening, finally resulting in glomerular fibrosis and sclerosis[7].

In general, glomerular hyperfiltration and renal hypertrophy occur in the first year after the onset of diabetes mellitus, and manifested by elevated glomerular filtration rate (for example, the normal glomerular filtration rate in humans is about 120 ml/min to about 150 ml/min). In the first 5 years after the onset of diabetes mellitus, pathological changes, such as glomerular hypertrophy, glomerular basement membrane thickening and glomerular mesangial volume expansion, can be observed. The glomerular filtration rate gradually returns to normal. Individuals begin to excrete microalbuminuria in the urine 5-10 years after the onset of diabetes mellitus. Microalbuminuria is an important indicator indicating the development into obvious diabetic nephropathy (characterized by large amounts of albuminuria in part). Basement membrane thickening and glomerular volume expansion seen early in the disease can continue to occur in advanced diabetic nephropathy, leading to occlusion of the capillary lumen, eventually leading to glomerular sclerosis. Once obvious diabetic nephropathy occurs, the glomerular filtration rate will decrease steadily, and approximately half of patients will develop into advanced renal disease within 7-10 years.

The development stages of diabetic nephropathy have been fully observed clinically. Stage I diabetic nephropathy is associated with increased glomerular filtration (i.e., hyperfiltration caused by increased blood flow through the kidneys and glomeruli), elevated glomerular filtration rate, glomerular hypertrophy and kidney enlargement. Stage II diabetic nephropathy is a clinically silent stage associated with continued hyperfiltration and renal hypertrophy. Glomerular basement membrane thickening and glomerular mesangial expansion occur. Stage III diabetic nephropathy (also known as primary diabetic nephropathy) is associated with microalbuminuria. The kidneys gradually lose the ability to filter wastes, and the blood levels of creatinine and urea nitrogen increase at the same time. Glomerular basement membrane thickening and glomerular mesangial expansion continue to occur as the condition worsens. Stage IV diabetic nephropathy (also known as obvious diabetic nephropathy) is associated with large amounts of albuminuria (i.e., clinical albuminuria) and continued increased levels of creatinine and blood urea nitrogen in blood. Stage V diabetic nephropathy occurs with the end-stage renal disease and renal failure.

The pathogenesis of diabetic nephropathy is complex. At present, the treatment methods for diabetic nephropathy are mainly diet control, blood glucose control, insulin injection, dialysis, kidney transplantation and the like. However, these treatment methods are too expensive and have serious complications, and currently there are very few drugs for diabetic nephropathy. Therefore, there is an urgent need for the development of such therapeutic drugs.

Plasmin is a key component of the plasminogen activation system (PA system). It is a broad-spectrum protease that can hydrolyze several components of the extracellular matrix (ECM), including fibrin, gelatin, fibronectin, laminin, and proteoglycan[8]. In addition, plasmin can activate some pro-matrix metalloproteinases (pro-MMPs) to form active matrix metalloproteinases (MMPs). Therefore, plasmin is considered to be an important upstream regulator of extracellular proteolysis[9,10]. Plasmin is formed by the proteolysis of plasminogen by two physiological PAs: tissue plasminogen activator (tPA) and urokinase-type plasminogen activator (uPA). Due to the relatively high level of plasminogen in plasma and other body fluids, it is traditionally believed that the regulation of the PA system is primarily achieved through the levels of PA synthesis and activity. The synthesis of PA system components is strictly regulated by different factors, such as hormones, growth factors and cytokines. In addition, there are also specific physiological inhibitors of plasmin and PAs. The main inhibitor of plasmin is α2-antiplasmin. There are uPA-specific cell surface receptors (uPARs) that have direct hydrolytic activity on certain cell surfaces[11,12].

Plasminogen (pig) is a single-stranded glycoprotein composed of 791 amino acids and has a molecular weight of about 92 kD[13,14]. Plasminogen is mainly synthesized in the liver and is abundantly present in the extracellular fluid. The content of plasminogen in plasma is about 2 μM. Therefore, plasminogen is a huge potential source of proteolytic activity in tissues and body fluids[15,16]. Plasminogen exists in two molecular forms: glutamic acid-plasminogen (Glu-plasminogen) and lysine-plasminogen (Lys-plasminogen). The naturally secreted and uncleaved forms of plasminogen have an amino-terminal (N-terminal) glutamic acid and are therefore referred to as glutamic acid-plasminogen. However, in the presence of plasmin, glutamic acid-plasminogen is hydrolyzed to lysine-plasminogen at Lys76-Lys77. Compared with glutamic acid-plasminogen, lysine-plasminogen has a higher affinity for fibrin and can be activated by PAs at a higher rate. The Arg560-Val561 peptide bond between these two forms of plasminogen can be cleaved by uPA or tPA, resulting in the formation of plasmin as a disulfide-linked double-strand protease[17]. The amino-terminal portion of plasminogen contains five homotrimeric rings, i.e., the so-called kringles, and the carboxy-terminal portion contains a protease domain. Some kringles contain lysine-binding sites that mediate the specific interaction of plasminogen with fibrin and its inhibitor α2-AP. A newly discovered 38 kD fragment of plasminogen, comprising kringles 1-4, is a potent inhibitor of angiogenesis. This fragment is named as angiostatin and can be produced by the proteolysis of plasminogen via several proteases.

The main substrate of plasmin is fibrin, and the dissolution of fibrin is the key to prevent pathological thrombosis[18]. Plasmin also has substrate specificity for several components of ECM, including laminin, fibronectin, proteoglycan and gelatin, indicating that plasmin also plays an important role in ECM remodeling[14,19,20]. Indirectly, plasmin can also degrade other components of ECM by converting certain protease precursors into active proteases, including MMP-1, MMP-2, MMP-3 and MMP-9. Therefore, it has been proposed that plasmin may be an important upstream regulator of extracellular proteolysis[21]. In addition, plasmin has the ability to activate certain potential forms of growth factors[22-24]. In vitro, plasmin can also hydrolyze components of the complement system and release chemotactic complement fragments.

Diabetic nephropathy is a common complication of diabetes mellitus. It is one of the manifestations of systemic microangiopathy of diabetes mellitus. It is clinically characterized by progressive renal function impairment, hypertension, edema, and severe renal failure in the late stage of proteinuria. It is one of the main reasons of death in diabetics. In recent years, with the prolongation of life expectancy of the Chinese population together with changes in living habits and eating habits and structures, the prevalence of diabetes mellitus has been on a linear upward trend, and due to the improvement of treatment methods and the increase of survival time, nephropathy and other complications have been correspondingly increased.

At present, the main methods for treating diabetic renal injury include drug treatment and dialysis treatment. Drugs mainly include antihypertensive drugs, statins, anticoagulants, antioxidant drugs and the like.

Antihypertensive drugs mainly include ACEI (angiotensin converting enzyme inhibitor) drugs, ARB (angiotensin II receptor blocker) drugs and ACER drugs, such as enalapril, captopril, benazepril and lisinopril. Such drugs may cause complications such as disturbance of taste, leukopenia, rash, loss of taste and irritable dry cough. ARB drugs include losartan, valsartan, candesartan, etc. ARB drugs have fewer complications but are expensive.

Statins are hydroxymethylglutaryl coenzyme A reductase inhibitors, mainly including lovastatin, simvastatin, pravastatin, fluvastatin, atorvastatin, etc., and such drugs protect the kidneys mainly through the hypolipidemic effect. There are side effects such as muscle pain and abnormal liver enzymes during the use of statins.

The currently used anticoagulants include heparin, warfarin, urokinase, etc., and such drugs may show concurrent symptoms such as bleeding and allergies.

Antioxidants include vitamin E, taurine, etc.

Dialysis treatment includes colon dialysis, peritoneal dialysis, hemodialysis, etc. In colon dialysis, the characteristics of the semipermeable membrane of the intestinal mucosa and the naturally vast dialysis area are used to actively eliminate toxins from the body, achieving blood purification. Peritoneal dialysis can control blood glucose well and does not require an established vascular fistula, but it is prone to cause peritonitis, leading to infections and protein loss. Hemodialysis is relatively simple and the treatment time is short; however, a vascular fistula needs to be established, and the burden on the cardiovascular system during dialysis is heavy.

In summary, the current drugs are mainly to provide antihypertensive, hypolipidemic, anticoagulant, antioxidant and other effects. However, these drugs are difficult to fundamentally change the damage of diabetes mellitus to the kidneys themselves.

Through research, the present inventors have surprisingly found that plasminogen has the effect of repairing renal injury and can be used for the treatment of diabetic nephropathy at various stages.

In our study, 31 days after intravenous injection of plasminogen in diabetic mice, the glomerular mesangial matrix of the mice is remarkably reduced; the deposition of fibrin is remarkably reduced; and the expression of apoptosis inhibitory proteins is remarkably increased. Changes of these indexes reflect that renal injury of the mice is significantly repaired, meaning that plasminogen has a significant therapeutic effect on diabetic renal injury and diabetic nephropathy.

At the same time, plasminogen has obvious repair and treatment effects on injuries and lesions of other tissues and organs caused by diabetes mellitus, for example it has repair and treatment effects on nerve injury, myocardial injury, hepatic injury and retinal injury caused by diabetes mellitus. Plasminogen has opened up a new chapter in the treatment of diabetic complications.

SUMMARY OF THE INVENTION

In one aspect, the present invention relates to a method for preventing, treating and/or eliminating diabetic nephropathy and/or its related disorders in a subject, comprising administering plasminogen or plasmin to the subject. In one aspect, the present invention also relates to the use of plasminogen for preventing, treating and/or eliminating diabetic nephropathy and/or its related disorders in a subject, comprising administering plasminogen or plasmin to the subject.

In one embodiment, the diabetic nephropathy includes glomerulopathy, including glomerular sclerosis and glomerular mesangial hyperplasia; tubulointerstitial lesions; and renal microangiopathy, including renal interstitial fibrosis, renal tubular atrophy, hyaline degeneration of the efferent arteries and renal microvascular sclerosis. In one embodiment, the diabetic nephropathy-related disorders include early renal enlargement, early increased glomerular filtration rate, intermittent proteinuria, microalbuminuria, macroalbuminuria, persistent proteinuria, decreased glomerular filtration rate, injured renal cell, renal fibrosis, renal insufficiency and uremia. In one embodiment, the diabetic nephropathy is caused by diabetes mellitus-induced angiopathy of large vessels, small vessels, and microvessels. In one embodiment, the plasminogen has at least 80%, 85%, 90%, 95%, 96%, 97%, 98% or 99% sequence identity with SEQ ID No. 2, 6, 8, 10 or 12, and still has the activity of plasminogen. In one embodiment, the plasminogen is a protein that comprises a plasminogen active fragment and still has the activity of plasminogen. In one embodiment, the plasminogen is selected from Glu-plasminogen, Lys-plasminogen, mini-plasminogen, micro-plasminogen, δ-plasminogen or any combination thereof. In one embodiment, the plasminogen is administered systemically or locally, for example, by intravenous, intramuscular, subcutaneous, inhalation, catheter administration, local injection or rectal administration. In one embodiment, the plasminogen can be administered in combination with one or more other drugs. In one embodiment, the other drugs include: antidiabetic drugs, antithrombotic drugs, antihypertensive drugs, hypolipidemic drugs, drugs against cardiovascular and cerebrovascular diseases, as well as anti-infective drugs.

In one embodiment, the subject is a mammal, preferably human.

In one embodiment, the subject has a low level of plasmin or plasminogen. Specifically, the low level is innate, secondary and/or local.

In one embodiment, the plasminogen has at least 80%, 85%, 90%, 95%, 96%, 97%, 98% or 99% sequence identity with SEQ ID No.2, 6, 8, 10 or 12, and still has the activity of plasminogen. In one embodiment, the plasminogen is a protein that has 1-100, 1-90, 1-80, 1-70, 1-60, 1-50, 1-45, 1-40, 1-35, 1-30, 1-25, 1-20, 1-15, 1-10, 1-5, 1-4, 1-3, 1-2 or 1 amino acid added, deleted and/or substituted in SEQ ID No.2, 6, 8, 10 or 12, and still has the activity of plasminogen. In one embodiment, the plasminogen is a protein that comprises a plasminogen active fragment and still has the activity of plasminogen. In one embodiment, the plasminogen is selected from Glu-plasminogen, Lys-plasminogen, mini-plasminogen, micro-plasminogen, δ-plasminogen or any combination thereof. In one embodiment, the plasminogen is a conservatively substituted variant selected from variants of Glu-plasminogen, Lys-plasminogen, mini-plasminogen, δ-plasminogen or micro-plasminogen variant selected from variants of Glu-plasminogen, Lys-plasminogen, mini-plasminogen, δ-plasminogen or micro-plasminogen variant selected from variants of Glu-plasminogen, Lys-plasminogen, mini-plasminogen, δ-plasminogen or micro-plasminogen variant selected from Glu-plasminogen, Lys-plasminogen, mini-plasminogen, δ-plasminogen or micro-plasminogen. In one embodiment, the plasminogen is a human natural plasminogen, such as an ortholog of plasminogen shown in SEQ ID No.2, e.g., an ortholog of plasminogen from primates or rodents, for example, an ortholog of plasminogen from gorillas, rhesus monkeys, murine, cows, horses and dogs. Most preferably, the amino acid sequence of the plasminogen of the present invention is as shown in SEQ ID No.2, 6, 8, 10 or 12.

In one embodiment, the plasminogen is administered in combination with a suitable polypeptide carrier or stabilizer. In one embodiment, the plasminogen is administered at a dosage of 0.0001-2000 mg/kg, 0.001-800 mg/kg, 0.01-600 mg/kg, 0.1-400 mg/kg, 1-200 mg/kg, 1-100 mg/kg or 10-100 mg/kg (by per kg of body weight) or 0.0001-2000 mg/cm$^2$, 0.001-800 mg/cm$^2$, 0.01-600 mg/cm$^2$, 0.1-400 mg/cm$^2$, 1-200 mg/cm$^2$, 1-100 mg/cm$^2$ or 10-100 mg/cm$^2$ (by per square centimeter of body surface area) daily, preferably the dosage is repeated at least once, preferably the dosage is administered at least daily. In the case of local administration, the above dosages may also be further adjusted depending on the circumstances.

The above plasminogen may be administered alone or in combination with other drugs including but not limited to antidiabetic drugs, such as insulin, acarbose, metformin, repaglinide, rosiglitazone and atorvastatin.

In one aspect, the present invention relates to the use of plasminogen or plasmin in the manufacture of a medicament for preventing, treating and/or eliminating diabetic nephropathy and/or its related disorders in a subject. In one aspect, the present invention relates to a method for manufacturing a medicament, comprising preparing a medicament for preventing, treating and/or eliminating diabetic nephropathy and/or its related disorders in a subject using plasminogen or plasmin together with a pharmaceutically acceptable carrier.

In one embodiment, the diabetic nephropathy includes glomerulopathy, including glomerular sclerosis and glomerular mesangial hyperplasia; tubulointerstitial lesions; and renal microangiopathy, including renal interstitial fibrosis, renal tubular atrophy, hyaline degeneration of the efferent arteries and renal microvascular sclerosis. In one embodiment, the diabetic nephropathy-related disorders include early renal enlargement, early increased glomerular filtration rate, intermittent proteinuria, microalbuminuria, macroalbuminuria, persistent proteinuria, decreased glomerular filtration rate, injured renal cell, renal fibrosis, renal insufficiency and uremia. In one embodiment, the diabetic nephropathy is caused by diabetes mellitus-induced angiopathy of large vessels, small vessels, and microvessels. In one embodiment, the plasminogen has at least 80%, 85%, 90%, 95%, 96%, 97%, 98% or 99% sequence identity with SEQ ID No. 2, 6, 8, 10 or 12, and still has the activity of plasminogen. In one embodiment, the plasminogen is a protein that comprises a plasminogen active fragment and still has the activity of plasminogen. In one embodiment, the plasminogen is selected from Glu-plasminogen, Lys-plasminogen, mini-plasminogen, micro-plasminogen, δ-plasminogen or any combination thereof. In one embodiment, the plasminogen is administered systemically or locally, for example, by intravenous, intramuscular, subcutaneous, inhalation, catheter administration, local injection or rectal administration. In one embodiment, the plasminogen can be administered in combination with one or more other drugs. In one embodiment, the other drugs include: antidiabetic drugs, antithrombotic drugs, antihypertensive drugs, hypolipidemic drugs, drugs against cardiovascular and cerebrovascular diseases, as well as anti-infective drugs.

In one embodiment, the subject is a mammal, preferably human.

In one embodiment, the subject has a low level of plasmin or plasminogen. Specifically, the low level is innate, secondary and/or local.

In one embodiment, the plasminogen has at least 80%, 85%, 90%, 95%, 96%, 97%, 98% or 99% sequence identity with SEQ ID No. 2, 6, 8, 10 or 12, and still has the activity of plasminogen. In one embodiment, the plasminogen is a protein that has 1-100, 1-90, 1-80, 1-70, 1-60, 1-50, 1-45, 1-40, 1-35, 1-30, 1-25, 1-20, 1-15, 1-10, 1-5, 1-4, 1-3, 1-2 or 1 amino acid added, deleted and/or substituted in SEQ ID No.2, 6, 8, 10 or 12, and still has the activity of plasminogen. In one embodiment, the plasminogen is a protein that comprises a plasminogen active fragment and still has the activity of plasminogen. In one embodiment, the plasminogen is selected from Glu-plasminogen, Lys-plasminogen, mini-plasminogen, micro-plasminogen, δ-plasminogen or any combination thereof. In one embodiment, the plasminogen is a conservatively substituted variant selected from variants of Glu-plasminogen, Lys-plasminogen, mini-plasminogen, δ-plasminogen or micro-plasminogen variant selected from variants of Glu-plasminogen, Lys-plasminogen, mini-plasminogen, δ-plasminogen or micro-plasminogen variant selected from variants of Glu-plasminogen, Lys-plasminogen, mini-plasminogen, δ-plasminogen or micro-plasminogen variant selected from Glu-plasminogen, Lys-plasminogen, mini-plasminogen, δ-plasminogen or micro-plasminogen. In one embodiment, the plasminogen is a human natural plasminogen, such as an ortholog of plasminogen shown in SEQ ID No.2, e.g., an ortholog of plasminogen from primates or rodents, for example, an ortholog of plasminogen from gorillas, rhesus monkeys, murine, cows, horses and dogs. Most preferably, the amino acid sequence of the plasminogen of the present invention is as shown in SEQ ID No.2, 6, 8, 10 or 12.

In one embodiment, the plasminogen is administered in combination with a suitable polypeptide carrier or stabilizer. In one embodiment, the plasminogen is administered at a dosage of 0.0001-2000 mg/kg, 0.001-800 mg/kg, 0.01-600 mg/kg, 0.1-400 mg/kg, 1-200 mg/kg, 1-100 mg/kg or 10-100 mg/kg (by per kg of body weight) or 0.0001-2000 mg/cm$^2$, 0.001-800 mg/cm$^2$, 0.01-600 mg/cm$^2$, 0.1-400 mg/cm$^2$, 1-200 mg/cm$^2$, 1-100 mg/cm$^2$ or 10-100 mg/cm$^2$ (by per square centimeter of body surface area) daily, preferably the dosage is repeated at least once, preferably the dosage is administered at least daily. In the case of local administration, the above dosages may also be further adjusted depending on the circumstances.

The above plasminogen may be administered alone or in combination with other drugs including but not limited to antidiabetic drugs, such as insulin, acarbose, metformin, repaglinide, rosiglitazone and atorvastatin.

In one aspect, the present invention relates to plasminogen or plasmin for preventing, treating and/or eliminating diabetic nephropathy and/or its related disorders in a subject, as well as a pharmaceutical composition which comprises plasminogen or plasmin and is useful in the prevention, treatment and/or elimination of diabetic nephropathy and/or its related disorders in a subject.

In one embodiment, the diabetic nephropathy includes glomerulopathy, including glomerular sclerosis and glomerular mesangial hyperplasia; tubulointerstitial lesions; and renal microangiopathy, including renal interstitial fibrosis, renal tubular atrophy, hyaline degeneration of the efferent arteries and renal microvascular sclerosis. In one embodiment, the diabetic nephropathy-related disorders include early renal enlargement, early increased glomerular filtration rate, intermittent proteinuria, microalbuminuria, macroalbuminuria, persistent proteinuria, decreased glomerular filtration rate, injured renal cell, renal fibrosis, renal insufficiency and uremia. In one embodiment, the diabetic nephropathy is caused by diabetes mellitus-induced angiopathy of large vessels, small vessels, and microvessels. In one embodiment, the plasminogen has at least 80%, 85%, 90%, 95%, 96%, 97%, 98% or 99% sequence identity with SEQ ID No. 2, 6, 8, 10 or 12, and still has the activity of plasminogen. In one embodiment, the plasminogen is a protein that comprises a plasminogen active fragment and still has the activity of plasminogen. In one embodiment, the plasminogen is selected from Glu-plasminogen, Lys-plasminogen, mini-plasminogen, micro-plasminogen, δ-plasminogen or any combination thereof. In one embodiment, the plasminogen is administered systemically or locally, for example, by intravenous, intramuscular, subcutaneous, inhalation, catheter administration, local injection or rectal administration. In one embodiment, the plasminogen can be administered in combination with one or more other drugs. In one embodiment, the other drugs include: antidiabetic drugs, antithrombotic drugs, antihypertensive drugs, hypolipidemic drugs, drugs against cardiovascular and cerebrovascular diseases, as well as anti-infective drugs.

In one embodiment, the subject is a mammal, preferably human.

In one embodiment, the subject has a low level of plasmin or plasminogen. Specifically, the low level is innate, secondary and/or local.

In one embodiment, the plasminogen has at least 80%, 85%, 90%, 95%, 96%, 97%, 98% or 99% sequence identity with SEQ ID No. 2, 6, 8, 10 or 12, and still has the activity of plasminogen. In one embodiment, the plasminogen is a protein that has 1-100, 1-90, 1-80, 1-70, 1-60, 1-50, 1-45, 1-40, 1-35, 1-30, 1-25, 1-20, 1-15, 1-10, 1-5, 1-4, 1-3, 1-2 or 1 amino acid added, deleted and/or substituted in SEQ ID No.2, 6, 8, 10 or 12, and still has the activity of plasminogen. In one embodiment, the plasminogen is a protein that comprises a plasminogen active fragment and still has the activity of plasminogen. In one embodiment, the plasminogen is selected from Glu-plasminogen, Lys-plasminogen, mini-plasminogen, micro-plasminogen, δ-plasminogen or any combination thereof. In one embodiment, the plasminogen is a conservatively substituted variant selected from variants of Glu-plasminogen, Lys-plasminogen, mini-plasminogen, δ-plasminogen or micro-plasminogen variant selected from variants of Glu-plasminogen, Lys-plasminogen, mini-plasminogen, δ-plasminogen or micro-plasminogen variant selected from variants of Glu-plasminogen, Lys-plasminogen, mini-plasminogen, δ-plasminogen or micro-plasminogen variant selected from Glu-plasminogen, Lys-plasminogen, mini-plasminogen, δ-plasminogen or micro-plasminogen. In one embodiment, the plasminogen is a human natural plasminogen, such as an ortholog of plasminogen shown in SEQ ID No.2, e.g., an ortholog of plasminogen from primates or rodents, for example, an ortholog of plasminogen from gorillas, rhesus monkeys, murine, cows, horses and dogs. Most preferably, the amino acid sequence of the plasminogen of the present invention is as shown in SEQ ID No.2, 6, 8, 10 or 12.

In one embodiment, the plasminogen is administered in combination with a suitable polypeptide carrier or stabilizer. In one embodiment, the plasminogen is administered at a dosage of 0.0001-2000 mg/kg, 0.001-800 mg/kg, 0.01-600 mg/kg, 0.1-400 mg/kg, 1-200 mg/kg, 1-100 mg/kg or 10-100 mg/kg (by per kg of body weight) or 0.0001-2000 mg/cm$^2$, 0.001-800 mg/cm$^2$, 0.01-600 mg/cm$^2$, 0.1-400 mg/cm$^2$, 1-200 mg/cm$^2$, 1-100 mg/cm$^2$ or 10-100 mg/cm$^2$ (by per square centimeter of body surface area) daily, preferably the dosage is repeated at least once, preferably the dosage is administered at least daily. In the case of local administration, the above dosages may also be further adjusted depending on the circumstances.

The above plasminogen may be administered alone or in combination with other drugs including but not limited to antidiabetic drugs, such as insulin, acarbose, metformin, repaglinide, rosiglitazone and atorvastatin.

In one aspect, the present invention relates to an article or kit of a pharmaceutical composition which comprises plasminogen or plasmin and is useful in the prevention, treatment and/or elimination of diabetic nephropathy and/or its related disorders in a subject. In one embodiment, the diabetic nephropathy includes glomerulopathy, including glomerular sclerosis and glomerular mesangial hyperplasia; tubulointerstitial lesions; and renal microangiopathy, including renal interstitial fibrosis, renal tubular atrophy, hyaline degeneration of the efferent arteries and renal microvascular sclerosis. In one embodiment, the diabetic nephropathy-related disorders include early renal enlargement, early increased glomerular filtration rate, intermittent proteinuria, microalbuminuria, macroalbuminuria, persistent proteinuria, decreased glomerular filtration rate, injured renal cell, renal fibrosis, renal insufficiency and uremia. In one embodiment, the diabetic nephropathy is caused by diabetes mellitus-induced angiopathy of large vessels, small vessels, and microvessels. In one embodiment, the plasminogen has at least 80%, 85%, 90%, 95%, 96%, 97%, 98% or 99% sequence identity with SEQ ID No. 2, 6, 8, 10 or 12, and still has the activity of plasminogen. In one embodiment, the plasminogen is a protein that comprises a plasminogen active fragment and still has the activity of plasminogen. In one embodiment, the plasminogen is selected from Glu-plasminogen, Lys-plasminogen, mini-plasminogen, micro-plasminogen, δ-plasminogen or any combination thereof. In one embodiment, the plasminogen is administered systemically or locally, for example, by intravenous, intramuscular, subcutaneous, inhalation, catheter administration, local injection or rectal administration. In one embodiment, the plasminogen can be administered in combination with one or more other drugs. In one embodiment, the other drugs include: antidiabetic drugs, antithrombotic drugs, antihypertensive drugs, hypolipidemic drugs, drugs against cardiovascular and cerebrovascular diseases, as well as anti-infective drugs.

In one embodiment, the subject is a mammal, preferably human.

In one embodiment, the subject has a low level of plasmin or plasminogen. Specifically, the low level is innate, secondary and/or local.

In one embodiment, the plasminogen has at least 80%, 85%, 90%, 95%, 96%, 97%, 98% or 99% sequence identity with SEQ ID No. 2, 6, 8, 10 or 12, and still has the activity of plasminogen. In one embodiment, the plasminogen is a protein that has 1-100, 1-90, 1-80, 1-70, 1-60, 1-50, 1-45, 1-40, 1-35, 1-30, 1-25, 1-20, 1-15, 1-10, 1-5, 1-4, 1-3, 1-2 or 1 amino acid added, deleted and/or substituted in SEQ ID No.2, 6, 8, 10 or 12, and still has the activity of plasminogen. In one embodiment, the plasminogen is a protein that comprises a plasminogen active fragment and still has the activity of plasminogen. In one embodiment, the plasminogen is selected from Glu-plasminogen, Lys-plasminogen, mini-plasminogen, micro-plasminogen, δ-plasminogen or any combination thereof. In one embodiment, the plasminogen is a conservatively substituted variant selected from variants of Glu-plasminogen, Lys-plasminogen, mini-plasminogen, δ-plasminogen or micro-plasminogen variant selected from variants of Glu-plasminogen, Lys-plasminogen, mini-plasminogen, δ-plasminogen or micro-plasminogen variant selected from variants of Glu-plasminogen, Lys-plasminogen, mini-plasminogen, δ-plasminogen or micro-plasminogen variant selected from Glu-plasminogen, Lys-plasminogen, mini-plasminogen, δ-plasminogen or micro-plasminogen. In one embodiment, the plasminogen is a human natural plasminogen, such as an ortholog of plasminogen shown in SEQ ID No.2, e.g., an ortholog of plasminogen from primates or rodents, for example, an ortholog of plasminogen from gorillas, rhesus monkeys, murine, cows, horses and dogs. Most preferably, the amino acid sequence of the plasminogen of the present invention is as shown in SEQ ID No.2, 6, 8, 10 or 12.

In one embodiment, the plasminogen is administered in combination with a suitable polypeptide carrier or stabilizer. In one embodiment, the plasminogen is administered at a dosage of 0.0001-2000 mg/kg, 0.001-800 mg/kg, 0.01-600 mg/kg, 0.1-400 mg/kg, 1-200 mg/kg, 1-100 mg/kg or 10-100 mg/kg (by per kg of body weight) or 0.0001-2000 mg/cm$^2$, 0.001-800 mg/cm$^2$, 0.01-600 mg/cm$^2$, 0.1-400 mg/cm$^2$, 1-200 mg/cm$^2$, 1-100 mg/cm$^2$ or 10-100 mg/cm$^2$ (by per square centimeter of body surface area) daily, preferably the dosage is repeated at least once, preferably the dosage is administered at least daily. In the case of local administration, the above dosages may also be further adjusted depending on the circumstances.

The above plasminogen may be administered alone or in combination with other drugs including but not limited to antidiabetic drugs, such as insulin, acarbose, metformin, repaglinide, rosiglitazone and atorvastatin.

In one embodiment, the article or kit comprises a container containing an effective dosage of plasminogen/plasmin. Preferably, the article or kit also comprises a container containing one or more other drugs. The kit can also comprise instructions for use, which indicate that the plasminogen can be used to prevent and/or treat the nephropathy caused by diabetes mellitus and nerve injury-related disorders, and can further indicate that the plasminogen can be administered before, simultaneously with and/or after administration of other drugs or therapies.

In one aspect, the present invention relates to the use of plasminogen or plasmin in the manufacture of a medicament, article or kit for preventing and/or treating injury (damage) to body tissues and internal organs caused by diabetes mellitus in a subject. In one embodiment, the injury (damage) to tissues and internal organs includes injury (damage) to the brain, heart, liver, lungs, kidneys, nerves, retina, skin and gastrointestinal tract. In one aspect, the present invention relates to the use of plasminogen in the manufacture of a medicament, article or kit for preventing and/or treating a diabetic complication in a subject. In one embodiment, the diabetic complication is diabetic encephalopathy, diabetic cardiopathy, diabetic hepatopathy, diabetic nephropathy, diabetic pneumonopathy, diabetic neuropathy, diabetic retinopathy or diabetic dermopathy induced by diabetes mellitus.

In one aspect, the present invention relates to a method for manufacturing a medicament, comprising preparing a medicament, article or kit for preventing and/or treating injury (damage) to body tissues and internal organs caused by diabetes mellitus in a subject using plasminogen or plasmin and a pharmaceutically acceptable carrier. In one embodiment, the injury (damage) to tissues and internal organs includes injury (damage) to the brain, heart, liver, lungs, kidneys, nerves, retina, skin and gastrointestinal tract. In one aspect, the present invention relates to a method for manufacturing a medicament, comprising preparing a medicament, article or kit for preventing and/or treating a diabetic complication in a subject using plasminogen or plasmin and a pharmaceutically acceptable carrier. In one embodiment, the diabetic complication is diabetic encephalopathy, diabetic cardiopathy, diabetic hepatopathy, diabetic nephropathy, diabetic pneumonopathy, diabetic neuropathy, diabetic retinopathy or diabetic dermopathy induced by diabetes mellitus.

In one aspect, the present invention relates to plasminogen or plasmin, and a pharmaceutical composition, article or kit comprising the plasminogen or plasmin, which are useful in the prevention and/or treatment of injury (damage) to body tissues and internal organs caused by diabetes mellitus in a subject. In one embodiment, the injury (damage) to tissues and internal organs includes injury (damage) to the brain, heart, liver, kidneys, lungs, nerves, retina, gastrointestinal tract and skin. In one aspect, the present invention relates to plasminogen, and a pharmaceutical composition, article or kit comprising the plasminogen, which are useful in the prevention and/or treatment of a diabetic complication in a subject. In one embodiment, the diabetic complication is diabetic encephalopathy, diabetic cardiopathy, diabetic hepatopathy, diabetic pneumonopathy, diabetic nephropathy, diabetic neuropathy, diabetic retinopathy or diabetic dermopathy induced by diabetes mellitus.

In one aspect, the present invention relates to a method for preventing and/or treating injury (damage) to body tissues and internal organs caused by diabetes mellitus in a subject, comprising administering plasminogen or plasmin or a pharmaceutical composition, article or kit comprising the plasminogen or plasmin to the subject. The present invention also relates to the use of plasminogen or plasmin, or a pharmaceutical composition, article or kit comprising the plasminogen or plasmin for preventing and/or treating injury (damage) to body tissues and internal organs caused by diabetes mellitus in a subject. In one embodiment, the injury (damage) to tissues and internal organs includes injury (damage) to the brain, heart, liver, lungs, kidneys, nerves, retina, gastrointestinal tract and skin. In one aspect, the present invention relates to a method for preventing and/or treating a diabetic complication in a subject, comprising administering plasminogen or plasmin, or a pharmaceutical composition, article or kit comprising the plasminogen or plasmin to the subject. The present invention also includes the use of plasminogen or plasmin, or a pharmaceutical composition, article or kit comprising the plasminogen or plasmin for preventing and/or treating a diabetic complication in a subject. In one embodiment, the diabetic complication is diabetic encephalopathy, diabetic cardiopathy, diabetic hepatopathy, diabetic pneumonopathy, diabetic nephropathy, diabetic neuropathy, diabetic retinopathy or diabetic dermopathy induced by diabetes mellitus.

In one embodiment, the subject has a low level of plasmin or plasminogen. Specifically, the low level is innate, secondary and/or local.

In one embodiment, the plasminogen has at least 80%, 85%, 90%, 95%, 96%, 97%, 98% or 99% sequence identity with SEQ ID No. 2, 6, 8, 10 or 12, and still has the activity of plasminogen. In one embodiment, the plasminogen is a protein that has 1-100, 1-90, 1-80, 1-70, 1-60, 1-50, 1-45, 1-40, 1-35, 1-30, 1-25, 1-20, 1-15, 1-10, 1-5, 1-4, 1-3, 1-2 or 1 amino acid added, deleted and/or substituted in SEQ ID No.2, 6, 8, 10 or 12, and still has the activity of plasminogen. In one embodiment, the plasminogen is a protein that comprises a plasminogen active fragment and still has the activity of plasminogen. In one embodiment, the plasminogen is selected from Glu-plasminogen, Lys-plasminogen, mini-plasminogen, micro-plasminogen, δ-plasminogen or any combination thereof. In one embodiment, the plasminogen is a conservatively substituted variant selected from variants of Glu-plasminogen, Lys-plasminogen, mini-plasminogen, δ-plasminogen or micro-plasminogen variant selected from variants of Glu-plasminogen, Lys-plasminogen, mini-plasminogen, δ-plasminogen or micro-plasminogen variant selected from variants of Glu-plasminogen, Lys-plasminogen, mini-plasminogen, δ-plasminogen or micro-plasminogen variant selected from Glu-plasminogen, Lys-plasminogen, mini-plasminogen, δ-plasminogen or micro-plasminogen. In one embodiment, the plasminogen is a human natural plasminogen, such as an ortholog of plasminogen shown in SEQ ID No.2, e.g., an ortholog of plasminogen from primates or rodents, for example, an ortholog of plasminogen from gorillas, rhesus monkeys, murine, cows, horses and dogs. Most preferably, the amino acid sequence of the plasminogen of the present invention is as shown in SEQ ID No.2, 6, 8, 10 or 12.

The present invention explicitly encompasses all the combinations of technical features belonging to the embodiments of the present invention, and these combined technical solutions have been explicitly disclosed in the present application, as if the above technical solutions were individually and explicitly disclosed. In addition, the present invention also explicitly encompasses all the subcombinations of the various embodiments and elements thereof, and these subcombinations have been disclosed herein, as if each of such subcombinations was individually and explicitly disclosed herein.

DETAILED DESCRIPTION OF EMBODIMENTS

1. Definition

"Diabetes mellitus" is a series of dysmetabolic syndromes of carbohydrates, proteins, fats, water, electrolytes and the like that are caused by islet hypofunction, insulin resistance and the like resulting from the effects of genetic factors, immune dysfunction, microbial infections and toxins thereof, free radical toxins, mental factors and other various pathogenic factors on the body, and is mainly characterized by hyperglycemia clinically.

"Diabetic complications" are damages to or dysfunctions of other organs or tissues of the body caused by poor blood glucose control during diabetes mellitus, including damages to or dysfunctions of the organs including the liver, kidneys, heart, retina, and nervous system damage and the like. According to statistics of the World Health Organization, there are up to more than 100 diabetic complications, and diabetes mellitus is a disease currently known to have the most complications. These complications of diabetes mellitus are mainly due to the injuries of large vessels, small vessels, and microvessels in various organs of patients.

"Diabetic microangiopathy" refers to microangiopathy caused by varying degrees of abnormalities in the microcirculation of various body organs or tissues of diabetics. The process of microangiopathy formation roughly comprises functional changes in microcirculation, endothelial injury, thickening of the basement membrane, increased blood viscosity, aggregation of red blood cells, and adhesion and aggregation of platelets, eventually leading to microthrombosis and/or microvascular occlusion.

The above-mentioned two types of "diabetic angiopathy" causes local vascular injury to tissues or organs, poor blood flow, hypoxia of cells, and formation of blood clots, thrombus and inflammation, and further affects the functions of peripheral tissues and organs, thereby causing "diabetic complications". Therefore, in the present invention, the terms "diabetic angiopathy" and "diabetic complications" cover the thrombus and microthrombus induced by diabetes mellitus, and the corresponding resulting organ and tissue lesions.

Diabetes mellitus is the leading cause of morbidity and mortality worldwide, and about 40% of diabetics develop into diabetic nephropathy and require renal dialysis or kidney transplantation. Diabetes mellitus is the leading cause of end-stage renal disease. Therefore, any diabetic has a risk of developing into diabetic nephropathy.

"Diabetic nephropathy" (or referred to as "diabetic kidney disease") is a diabetic microvascular complication, and mainly refers to diabetic glomerular sclerosis, as a glomerulopathy that is predominantly vascular injury, characterized by proteinuria, hypertension, edema, glomerular sclerosis, vascular structural changes and tubulointerstitial disease.

"Plasmin" is a very important enzyme that exists in the blood and can hydrolyze fibrin clots into fibrin degradation products and D-dimers.

"Plasminogen" is the zymogenic form of plasmin, and based on the sequence in the swiss prot and calculated from the amino acid sequence (SEQ ID No.4) of the natural human-derived plasminogen containing a signal peptide, is a glycoprotein composed of 810 amino acids, which has a molecular weight of about 92 kD and is synthesized mainly in the liver and capable of circulating in the blood; and the cDNA sequence encoding this amino acid sequence is as shown in SEQ ID No.3. Full-length plasminogen contains seven domains: a C-terminal serine protease domain, an N-terminal Pan Apple (PAp) domain and five Kringle domains (Kringles 1-5). Referring to the sequence in the swiss prot, the signal peptide comprises residues Met1-Gly19, PAp comprises residues Glu20-Val98, Kringle 1 comprises residues Cys103-Cys181, Kringle 2 comprises residues Glu184-Cys262, Kringle 3 comprises residues Cys275-Cys352, Kringle 4 comprises residues Cys377-Cys454, and Kringle 5 comprises residues Cys481-Cys560. According to the NCBI data, the serine protease domain comprises residues Val581-Arg804.

Glu-plasminogen is a natural full-length plasminogen and is composed of 791 amino acids (without a signal peptide of 19 amino acids); the cDNA sequence encoding this sequence is as shown in SEQ ID No.1; and the amino acid sequence is as shown in SEQ ID No.2. In vivo, Lys-plasminogen, which is formed by hydrolysis of amino acids at positions 76-77 of Glu-plasminogen, is also present, as shown in SEQ ID No.6; and the cDNA sequence encoding this amino acid sequence is as shown in SEQ ID No.5. δ-plasminogen is a fragment of full-length plasminogen that lacks the structure of Kringle 2-Kringle 5 and contains only Kringle 1 and the serine protease domain[25,26]. The amino acid sequence (SEQ ID No.8) of δ-plasminogen has been reported in the literature[26], and the cDNA sequence encoding this amino acid sequence is as shown in SEQ ID No.7. Mini-plasminogen is composed of Kringle 5 and the serine protease domain, and has been reported in the literature to comprise residues Val443-Asn791 (with the Glu residue of the Glu-plasminogen sequence that does not contain a signal peptide as the starting amino acid)[27]; the amino acid sequence is as shown in SEQ ID No.10; and the cDNA sequence encoding this amino acid sequence is as shown in SEQ ID No.9. Micro-plasminogen comprises only the serine protease domain, the amino acid sequence of which has been reported in the literature to comprise residues Ala543-Asn791 (with the Glu residue of the Glu-plasminogen sequence that does not contain a signal peptide as the starting amino acid)[28], and the sequence of which has been also reported in patent document CN 102154253 A to comprise residues Lys531-Asn791 (with the Glu residue of the Glu-plasminogen sequence that does not contain a signal peptide as the starting amino acid) (the sequence in this patent application refers to the patent document CN 102154253 A document CN 102154253 A); the amino acid sequence is as shown in SEQ ID No.12; and the cDNA sequence encoding this amino acid sequence is as shown in SEQ ID No.11.

In the present invention, "plasmin" is used interchangeably with "fibrinolysin" and "fibrinoclase", and the terms have the same meaning; and "plasminogen" is used interchangeably with "fibrinolytic zymogen" and "fibrinoclase zymogen", and the terms have the same meaning.

Those skilled in the art can understand that all the technical solutions of the plasminogen of the present invention are suitable for plasmin. Therefore, the technical solutions described in the present invention cover plasminogen and plasmin.

In the course of circulation, plasminogen is in a closed, inactive conformation, but when bound to thrombi or cell surfaces, it is converted into an active plasmin in an open conformation under the mediation of a plasminogen activator (PA). The active plasmin can further hydrolyze the fibrin clots to fibrin degradation products and D-dimers, thereby dissolving the thrombi. The PAp domain of plasminogen comprises an important determinant that maintains plasminogen in an inactive, closed conformation, and the KR domain is capable of binding to lysine residues present on receptors and substrates. A variety of enzymes that can serve as plasminogen activators are known, including: tissue plasminogen activator (tPA), urokinase plasminogen activator (uPA), kallikrein, coagulation factor XII (Hagmann factor), and the like.

"Plasminogen active fragment" refers to an active fragment in the plasminogen protein that is capable of binding to a target sequence in a substrate and exerting the proteolytic function. The technical solutions of the present invention involving plasminogen encompass technical solutions in which plasminogen is replaced with a plasminogen active fragment. The plasminogen active fragment of the present invention is a protein comprising a serine protease domain of plasminogen. Preferably, the plasminogen active fragment of the present invention comprises SEQ ID NO: 14, or an amino acid sequence having an amino acid sequence identity of at least 80%, 90%, 95%, 96%, 97%, 98% or 99% with SEQ ID NO: 14. Therefore, plasminogen of the present invention comprises a protein comprising the plasminogen active fragment and still having plasminogen activity.

At present, methods for determining plasminogen and its activity in blood include: detection of tissue plasminogen activator activity (t-PAA), detection of tissue plasminogen activator antigen (t-PAAg) in plasma, detection of tissue plasminogen activity (plgA) in plasma, detection of tissue plasminogen antigen (plgAg) in plasma, detection of activity of the inhibitor of tissue plasminogen activators in plasma, detection of inhibitor antigens of tissue plasminogen activators in plasma and detection of plasmin-anti-plasmin (PAP) complex in plasma. The most commonly used detection method is the chromogenic substrate method: streptokinase (SK) and a chromogenic substrate are added to a test plasma, the plasminogen in the test plasma is converted into plasmin by the action of SK, said plasmin acts on the chromogenic substrate, and then it is determined that the increase in absorbance is directly proportional to plasminogen activity using a spectrophotometer. In addition, plasminogen activity in blood can also be determined by immunochemistry, gel electrophoresis, immunonephelometry, radioimmuno-diffusion and the like.

"Orthologues or orthologs" refer to homologs between different species, including both protein homologs and DNA homologs, and are also known as orthologous homologs and vertical homologs. The term specifically refers to proteins or genes that have evolved from the same ancestral gene in different species. The plasminogen of the present invention includes human natural plasminogen, and also includes orthologues or orthologs of plasminogens derived from different species and having plasminogen activity.

"Conservatively substituted variant" refers to one in which a given amino acid residue is changed without altering the overall conformation and function of the protein or enzyme, including, but not limited to, replacing an amino acid in the amino acid sequence of the parent protein by an amino acid with similar properties (such as acidity, alkalinity and hydrophobicity). Amino acids with similar properties are well known. For example, arginine, histidine and lysine are hydrophilic basic amino acids and are interchangeable. Similarly, isoleucine is a hydrophobic amino acid that can be replaced by leucine, methionine or valine. Therefore, the similarity of two proteins or amino acid sequences with similar functions may be different. For example, the similarity (identity) is 70%-99% based on the MEGALIGN algorithm. "Conservatively substituted variant" also includes a polypeptide or enzyme having amino acid identity of 60% or more, preferably 75% or more, more preferably 85% or more, even more preferably 90% or more as determined by the BLAST or FASTA algorithm, and having the same or substantially similar properties or functions as the natural or parent protein or enzyme.

"Isolated" plasminogen refers to the plasminogen protein that is isolated and/or recovered from its natural environment. In some embodiments, the plasminogen will be purified (1) to a purity of greater than 90%, greater than 95% or greater than 98% (by weight), as determined by the Lowry method, such as more than 99% (by weight); (2) to a degree sufficiently to obtain at least 15 residues of the N-terminal or internal amino acid sequence using a spinning cup sequenator; or (3) to homogeneity, which is determined by sodium dodecyl sulfate-polyacrylamide gel electrophoresis (SDS-PAGE) under reducing or non-reducing conditions using Coomassie blue or silver staining. Isolated plasminogen also includes plasminogen prepared from recombinant cells by bioengineering techniques and separated by at least one purification step.

The terms "polypeptide", "peptide" and "protein" are used interchangeably herein and refer to polymeric forms of amino acids of any length, which may include genetically encoded and non-genetically encoded amino acids, chemically or biochemically modified or derivatized amino acids, and polypeptides having modified peptide backbones. The term includes fusion proteins, including, but not limited to, fusion proteins having heterologous amino acid sequences, fusions having heterologous and homologous leader sequences (with or without N-terminal methionine residues), and the like.

The "percent amino acid sequence identity (%)" with respect to the reference polypeptide sequence is defined as the percentage of amino acid residues in the candidate sequence identical to the amino acid residues in the reference polypeptide sequence when a gap is introduced as necessary to achieve maximal percent sequence identity and no conservative substitutions are considered as part of sequence identity. The comparison for purposes of determining percent amino acid sequence identity can be achieved in a variety of ways within the skill in the art, for example using publicly available computer softwares, such as BLAST, BLAST-2, ALIGN or Megalign (DNASTAR) software. Those skilled in the art can determine appropriate parameters for aligning sequences, including any algorithm needed to achieve the maximum comparison over the full length of the sequences being compared. However, for purposes of the present invention, the percent amino acid sequence identity value is generated using the sequence comparison computer program ALIGN-2.

In the case of comparing amino acid sequences using ALIGN-2, the % amino acid sequence identity of a given amino acid sequence A relative to a given amino acid sequence B (or may be expressed as a given amino acid sequence A having or containing a certain % amino acid sequence identity relative to, with or for a given amino acid sequence B) is calculated as follows:

fraction $X/Y \times 100$ wherein X is the number of identically matched amino acid residues scored by the sequence alignment program ALIGN-2 in the alignment of A and B using the program, and wherein Y is the total number of amino acid residues in B. It will be appreciated that where the length of amino acid sequence A is not equal to the length of amino acid sequence B, the % amino acid sequence identity of A relative to B will not be equal to the % amino acid sequence identity of B relative to A. Unless specifically stated otherwise, all the % amino acid sequence identity values used herein are obtained using the ALIGN-2 computer program as described in the previous paragraph.

As used herein, the terms "treatment" and "treating" refer to obtaining a desired pharmacological and/or physiologic effect. The effect may be complete or partial prevention of a disease or its symptoms and/or partial or complete cure of the disease and/or its symptoms, and includes: (a) prevention of the disease from developing in a subject that may have a predisposition to the disease but has not been diagnosed as having the disease; (b) suppression of the disease, i.e., blocking its formation; and (c) alleviation of the disease and/or its symptoms, i.e., eliminating the disease and/or its symptoms.

The terms "individual", "subject" and "patient" are used interchangeably herein and refer to mammals, including, but not limited to, murine (rats and mice), non-human primates, humans, dogs, cats, hoofed animals (e.g., horses, cattle, sheep, pigs, goats) and so on.

"Therapeutically effective amount" or "effective amount" refers to an amount of plasminogen sufficient to achieve the prevention and/or treatment of a disease when administered to a mammal or another subject to treat the disease. The "therapeutically effective amount" will vary depending on the plasminogen used, the severity of the disease and/or its symptoms, as well as the age, body weight of the subject to be treated, and the like.

2. Preparation of the Plasminogen of the Present Invention

Plasminogen can be isolated and purified from nature for further therapeutic uses, and can also be synthesized by standard chemical peptide synthesis techniques. When chemically synthesized, a polypeptide can be subjected to liquid or solid phase synthesis. Solid phase polypeptide synthesis (SPPS) is a method suitable for chemical synthesis of plasminogen, in which the C-terminal amino acid of a sequence is attached to an insoluble support, followed by the sequential addition of the remaining amino acids in the sequence. Various forms of SPPS, such as Fmoc and Boc, can be used to synthesize plasminogen. Techniques for solid phase synthesis are described in Barany and Solid-Phase Peptide Synthesis; pp. 3-284 in The Peptides: Analysis, Synthesis, Biology. Vol. 2: Special Methods in Peptide Synthesis, Part A., Merrifield et al. J. Am. Chem. Soc., 85: 2149-2156 (1963); Stewart et al. Solid Phase Peptide Synthesis, 2nd ed. Pierce Chem. Co., Rockford, Ill. (1984); and Ganesan A. 2006 Mini Rev. Med Chem. 6:3-10 and Camarero J A et al. 2005 Protein Pept Lett. 12:723-8. Briefly, small insoluble porous beads are treated with a functional unit on which a peptide chain is constructed. After repeated cycles of coupling/deprotection, the attached solid phase free N-terminal amine is coupled to a single N-protected amino acid unit. This unit is then deprotected to expose a new N-terminal amine that can be attached to another amino acid. The peptide remains immobilized on the solid phase before it is cut off.

Standard recombinant methods can be used to produce the plasminogen of the present invention. For example, a nucleic acid encoding plasminogen is inserted into an expression vector, so that it is operably linked to a regulatory sequence in the expression vector. Expression regulatory sequence includes, but is not limited to, promoters (e.g., naturally associated or heterologous promoters), signal sequences, enhancer elements and transcription termination sequences. Expression regulation can be a eukaryotic promoter system in a vector that is capable of transforming or transfecting eukaryotic host cells (e.g., COS or CHO cells). Once the vector is incorporated into a suitable host, the host is maintained under conditions suitable for high-level expression of the nucleotide sequence and collection and purification of plasminogen.

A suitable expression vector is usually replicated in a host organism as an episome or as an integral part of the host chromosomal DNA. In general, an expression vector contains a selective marker (e.g., ampicillin resistance, hygromycin resistance, tetracycline resistance, kanamycin resistance or neomycin resistance) to facilitate detection of those exogenous cells transformed with a desired DNA sequence.

*Escherichia coli* is an example of prokaryotic host cells that can be used to clone a polynucleotide encoding the subject antibody. Other microbial hosts suitable for use include *Bacillus*, for example, *Bacillus subtilis* and other species of Enterobacteriaceae (such as *Salmonella* spp. and *Serratia* spp.), and various *Pseudomonas* spp. In these prokaryotic hosts, expression vectors can also be generated which will typically contain an expression control sequence (e.g., origin of replication) that is compatible with the host cell. In addition, there will be many well-known promoters, such as the lactose promoter system, the tryptophan (trp) promoter system, the beta-lactamase promoter system or the promoter system from phage lambda. Optionally in the case of manipulation of a gene sequence, a promoter will usually control expression, and has a ribosome binding site sequence and the like to initiate and complete transcription and translation.

Other microorganisms, such as yeast, can also be used for expression. *Saccharomyces* (e.g., *S. cerevisiae*) and *Pichia* are examples of suitable yeast host cells, in which a suitable vector has an expression control sequence (e.g., promoter), an origin of replication, a termination sequence and the like, as required. A typical promoter comprises 3-phosphoglycerate kinase and other glycolytic enzymes. Inducible yeast promoters specifically include promoters derived from alcohol dehydrogenase, isocytochrome C, and enzymes responsible for maltose and galactose utilization.

In addition to microorganisms, mammalian cells (eg, mammalian cells cultured in in vitro cell culture) can also be used to express and produce the protein of the invention (eg, polynucleotides encoding the subject protein). See Winnacker, From Genes to Clones, VCH Publishers, N.Y., N.Y. (1987). Suitable mammalian host cells include CHO cell lines, various Cos cell lines, HeLa cells, myeloma cell lines and transformed B cells or hybridomas. Expression vectors for these cells may comprise an expression control sequence, such as an origin of replication, promoter and enhancer (Queen et al. Immunol. Rev. 89:49 (1986)), as well as necessary processing information sites, such as a ribosome binding site, RNA splice site, polyadenylation site and transcription terminator sequence. Examples of suitable expression control sequences are promoters derived from white immunoglobulin gene, SV40, adenovirus, bovine papilloma virus, cytomegalovirus and the like. See Co et al. J. Immunol. 148:1149 (1992).

Once synthesized (chemically or recombinantly), the plasminogen of the present invention can be purified according to standard procedures in the art, including ammonium sulfate precipitation, affinity column, column chromatography, high performance liquid chromatography (HPLC), gel electrophoresis and the like. The plasminogen is substantially pure, e.g., at least about 80% to 85% pure, at least about 85% to 90% pure, at least about 90% to 95% pure, or 98% to 99% pure or purer, for example free of contaminants such as cell debris, macromolecules other than the plasminogen and the like.

3. Pharmaceutical Formulations

A therapeutic formulation can be prepared by mixing plasminogen of a desired purity with an optional pharmaceutical carrier, excipient or stabilizer (Remington's Pharmaceutical Sciences, 16th edition, Osol, A. ed. (1980)) to form a lyophilized preparation or an aqueous solution. Acceptable carriers, excipients and stabilizers are non-toxic to the recipient at the dosages and concentrations employed, and include buffers, such as phosphates, citrates and other organic acids; antioxidants, including ascorbic acid and methionine; preservatives (e.g., octadecyl dimethyl benzyl ammonium chloride; hexane chloride diamine; benzalkonium chloride and benzethonium chloride; phenol, butanol or benzyl alcohol; alkyl p-hydroxybenzoates, such as methyl or propyl p-hydroxybenzoate; catechol; resorcinol; cyclohexanol; 3-pentanol; and m-cresol); low molecular weight polypeptides (less than about 10 residues); proteins, such as serum albumin, gelatin or immunoglobulins; hydrophilic polymers, such as polyvinylpyrrolidone; amino acids, such as glycine, glutamine, asparagine, histidine, arginine or lysine; monosaccharides, disaccharides and other carbohydrates, including glucose, mannose or dextrins; chelating agents, such as EDTA; sugars, such as sucrose, mannitol, fucose or sorbitol; salt-forming counterions, such as sodium; metal complexes (e.g., zinc-protein complexes); and/or non-ionic surfactants, such as TWEEN™, PLURONICS™ or polyethylene glycol (PEG).

The formulations of the invention may also comprise one or more active compounds required for the particular disorder to be treated, preferably those that are complementary in activity and have no side effects with one another, for example anti-hypertensive drugs, anti-arrhythmic drugs, drugs for treating diabetes mellitus, and the like.

The plasminogen of the present invention may be encapsulated in microcapsules prepared by techniques such as coacervation or interfacial polymerization, for example, it may be incorporated in a colloid drug delivery system (e.g., liposomes, albumin microspheres, microemulsions, nanoparticles and nanocapsules), or incorporated in hydroxymethylcellulose or gel-microcapsules and poly-(methyl methacrylate) microcapsules in macroemulsions. These techniques are disclosed in Remington's Pharmaceutical Sciences, 16th edition, Osol, A. Ed. (1980).

The plasminogen of the present invention for in vivo administration must be sterile. This can be easily achieved by filtration through a sterile filtration membrane before or after freeze drying and reconstitution.

The plasminogen of the present invention can be prepared into a sustained-release preparation. Suitable examples of sustained-release preparations include solid hydrophobic polymer semi-permeable matrices having a shape and containing glycoproteins, such as films or microcapsules. Examples of sustained-release matrices include polyesters, hydrogels (e.g., poly(2-hydroxyethyl-methacrylate)) (Langer et al. J. Biomed. Mater. Res., 15: 167-277 (1981); and Langer, Chem. Tech., 12:98-105 (1982)), or poly(vinyl alcohol), polylactides (U.S. Pat. No. 3,773,919, and EP 58, 481), copolymer of L-glutamic acid and □ ethyl-L-glutamic acid (Sidman et al. Biopolymers 22:547 (1983)), nondegradable ethylene-vinyl acetate (Langer et al. supra), or degradable lactic acid-glycolic acid copolymers such as Lupron Depot™ (injectable microspheres composed of lactic acid-glycolic acid copolymer and leuprolide acetate), and poly D-(-)-3-hydroxybutyric acid. Polymers, such as ethylene-vinyl acetate and lactic acid-glycolic acid, are able to persistently release molecules for 100 days or longer, while some hydrogels release proteins for a shorter period of time. A rational strategy for protein stabilization can be designed based on relevant mechanisms. For example, if the aggregation mechanism is discovered to be formation of an intermolecular S—S bond through thio-disulfide interchange, stability is achieved by modifying sulfhydryl residues, lyophilizing from acidic solutions, controlling moisture content, using appropriate additives, and developing specific polymer matrix compositions.

4. Administration and Dosage

The pharmaceutical composition of the present invention can be administered in different ways, for example by intravenous, intraperitoneal, subcutaneous, intracranial, intrathecal, intraarterial (e.g., via carotid), intramuscular, intranasal, topical or intradermal administration or spinal cord or brain delivery. An aerosol preparation, such as a nasal spray preparation, comprises purified aqueous or other solutions of the active agent along with a preservative and isotonic agent. Such preparations are adjusted to a pH and isotonic state compatible with the nasal mucosa.

In some cases, the plasminogen pharmaceutical composition of the present invention may be modified or formulated in such a manner to provide its ability to cross the blood-brain barrier. Such plasminogen compositions can be administered to an individual suffering from thrombosis and/or a thrombosis-related disease via a variety of enteral and parenteral routes of administration, including oral, intravenous and the like.

Preparations for parenteral administration include sterile aqueous or non-aqueous solutions, suspensions and emulsions. Examples of non-aqueous solvents are propylene glycol, polyethylene glycol, vegetable oils such as olive oil, and injectable organic esters such as ethyl oleate. Aqueous carriers include water, and alcoholic/aqueous solutions, emulsions or suspensions, including saline and buffered media. Parenteral vehicles include sodium chloride solution, Ringer's dextrose, dextrose and sodium chloride, or fixed oils. Intravenous vehicles include liquid and nutrient supplements, electrolyte supplements and the like. Preservatives and other additives may also be present, for example, such as antimicrobial agents, antioxidants, chelating agents and inert gases.

In some embodiments, the plasminogen of the invention is formulated with an agent that promotes the plasminogen to cross the blood-brain barrier. In some cases, the plasminogen of the present invention is fused directly or via a linker to a carrier molecule, peptide or protein that promotes the fusion to cross the blood brain barrier. In some embodiments, the plasminogen of the present invention is fused to a polypeptide that binds to an endogenous blood-brain barrier (BBB) receptor. The polypeptide that is linked to plasminogen and binds to an endogenous BBB receptor promotes the fusion to cross the BBB. Suitable polypeptides that bind to endogenous BBB receptors include antibodies (e.g., monoclonal antibodies) or antigen-binding fragments thereof that specifically bind to endogenous BBB receptors. Suitable endogenous BBB receptors include, but are not limited to, insulin receptors. In some cases, antibodies are encapsulated in liposomes. See, for example, US Patent Publication No. 2009/0156498.

The medical staff will determine the dosage regimen based on various clinical factors. As is well known in the medical field, the dosage of any patient depends on a variety of factors, including the patient's size, body surface area, age, the specific compound to be administered, sex, frequency and route of administration, overall health and other drugs administered simultaneously. The dosage range of the pharmaceutical composition comprising plasminogen of the present invention may be, for example, about 0.0001 to 2000 mg/kg, or about 0.001 to 500 mg/kg (such as 0.02 mg/kg, 0.25 mg/kg, 0.5 mg/kg, 0.75 mg/kg, 10 mg/kg and 50 mg/kg) of the subject's body weight daily. For example, the dosage may be 1 mg/kg body weight or 50 mg/kg body weight, or in the range of 1 mg/kg-50 mg/kg, or at least 1 mg/kg. Dosages above or below this exemplary range are also contemplated, especially considering the above factors. The intermediate dosages in the above range are also included in the scope of the present invention. A subject may be administered with such dosages daily, every other day, weekly or based on any other schedule determined by empirical analysis. An exemplary dosage schedule includes 1-10 mg/kg for consecutive days. During administration of the drug of the present invention, the therapeutic effect and safety are required to be assessed real-timely and regularly.

5. Treatment Efficacy

One embodiment of the present invention relates to the judgment of treatment efficacy and treatment safety after treating a subject with plasminogen. Clinically, the methods for judging treatment efficacy include, but are not limited to, detection of the following indexes to assess renal function: serum creatinine level, creatinine clearance, 24-hour urinary protein excretion rate (UAER), glomerular filtration rate, urinary albumin/creatinine ratio, albumin secretion rate, renal biopsy, etc. For example, the glomerular filtration rate can indicate glomerular hyperfiltration and hyperperfusion, indicating the degree of relief of the early symptoms of diabetic nephropathy. The glomerular filtration rate is the volume of filtrate produced per minute by the kidneys and can be determined by a variety of methods, such as measurement of urinary clearance of filtration markers, such as glycans, iothalamates or iohexols. A more commonly used method can be estimating glomerular filtration rate by determining creatinine (a protein produced by muscle and released into the blood) clearance. The creatinine clearance (usually expressed in milliliters per minute) can be determined by comparing the level of creatinine collected in the urine with the level of creatinine in the blood over a given time (e.g., 12 or 24 hours). The typical creatinine clearance in adult males is approximately 97-137 ml/min, and that in adult females is approximately 88-128 ml/min. The creatinine clearance is directly proportional to urinary creatinine excretion and inversely proportional to serum creatinine concentration.

Creatinine clearance/glomerular filtration rate or urinary albumin excretion rate is usually used as the main efficacy assessment index. Furthermore, other secondary indexes can be added to assess the efficacy of the drug of the present invention on related complications, for example, detection of triglyceride, total cholesterol, low-density lipoprotein and the like is added to assess blood lipid changes; detection of systolic blood pressure and diastolic blood pressure before and after treatment is added to assess the degree of relief of hypertension; and so on.

6. Articles or Kits

One embodiment of the present invention relates to an article or kit comprising plasminogen of the present invention useful in the treatment of diabetic nephropathy. The article preferably includes a container, label or package insert. Suitable containers include bottles, vials, syringes and the like. The container can be made of various materials, such as glass or plastic. The container contains a composition that is effective to treat the disease or disorder of the present invention and has a sterile access (for example, the container may be an intravenous solution bag or vial containing a plug that can be pierced by a hypodermic injection needle). At least one active agent in the composition is plasminogen. The label on or attached to the container indicates that the composition is used to treat the diabetic nephropathy of the present invention and diabetic nephropathy-related diseases. The article may further comprise a second container containing a pharmaceutically acceptable buffer, such as phosphate buffered saline, Ringer's solution and glucose solution. It may further comprise other substances required from a commercial and user perspective, including other buffers, diluents, filters, needles and syringes. In addition, the article comprises a package insert with instructions for use, including, for example, instructions to a user of the composition to administer the plasminogen composition and other drugs to treat an accompanying disease to a patient.

EXAMPLES

Example 1. Effect of Plasminogen on Body Weight of Early Diabetic Mice

Ten male db/db mice aged 14-15 weeks were randomly divided into two groups, five in the control group administered with vehicle PBS and five in the group administered with plasminogen, respectively. The day when the experiment began was recorded on Day 0, and the mice were weighed and grouped. From the second day of the experiment, plasminogen or PBS was administered to the mice, and the day was recorded as Day 1. Mice in the group administered with plasminogen were injected with plasminogen at a dose of 1 mg/0.1 mL/mouse/day via the tail vein, and an equal volume of PBS was administered to mice in the control group administered with vehicle PBS. The mice were weighed on days 0, 3, 6 and 12, respectively.

Figure 1:
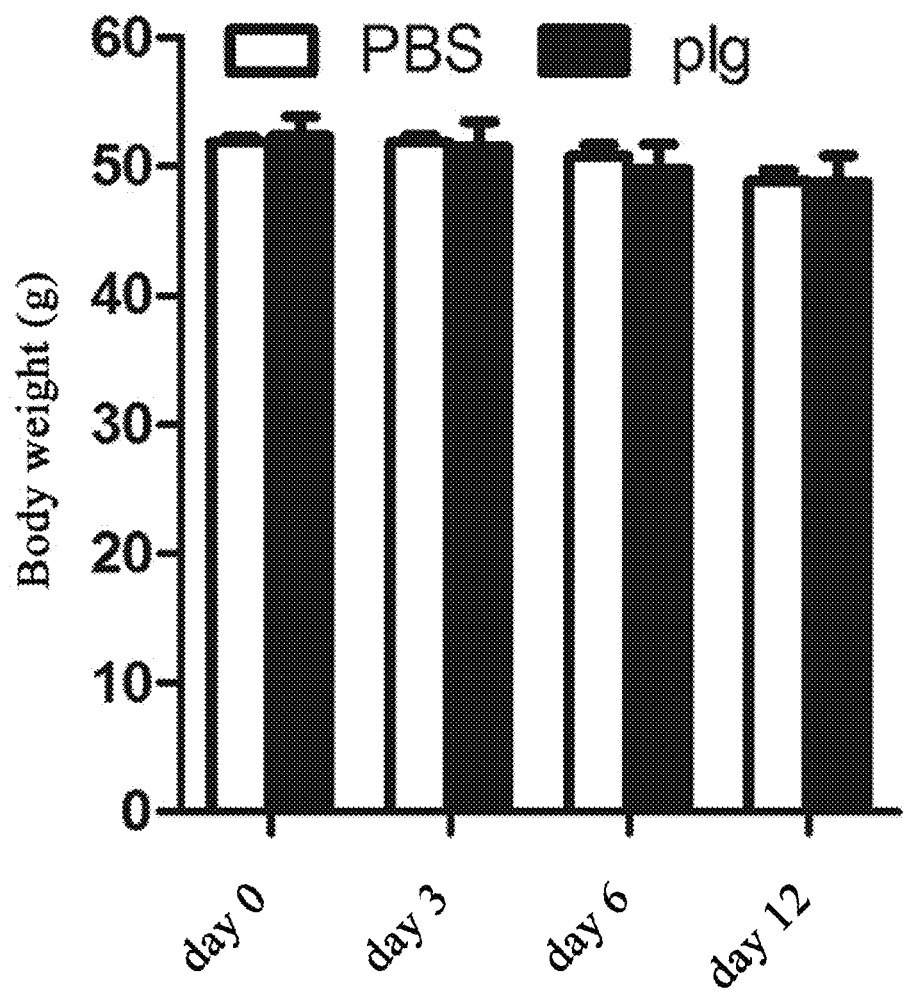
FIG. 1 shows changes in body weight after administration of plasminogen to 14-15-week-old db/db mice.

The results showed that there was no significant difference in body weight between mice in the group administered with plasminogen and those in the control group administered with vehicle PBS on days 0, 3, 6 and 12 (FIG. 1), indicating that plasminogen has little effect on animal body weight.

Example 2. Effect of Plasminogen on Hyperplasia of Glomerular Mesangial Matrix and Basement Membrane in Early Diabetic Mice Ten male db/db mice aged 14-15 weeks were randomly divided into two groups, five in the control group administered with vehicle PBS and five in the group administered with plasminogen, respectively. The day when the experiment began was recorded on Day 0, and the mice were weighed and grouped. From the second day of the experiment, plasminogen or PBS was administered to the mice, and the day was recorded as Day 1. Mice in the group administered with plasminogen were injected with plasminogen at a dose of 1 mg/0.1 mL/mouse/day via the tail vein, and an equal volume of PBS was administered to mice in the control group administered with vehicle PBS. Mice were sacrificed on day 12, and the left kidneys were fixed in Carnoy fix solution for 24 hours. The fixed kidney tissues were paraffin-embedded after dehydration with alcohol gradient and permeabilization with xylene. The thickness of the sections was 5 μm. The sections were dewaxed and rehydrated, stained with hematoxylin and periodic acid-Schiff (PAS staining), differentiated with 1% hydrochloric acid in alcohol, and returned to blue with ammonia water. The sections were sealed after dehydration with alcohol gradient and permeabilization with xylene, and observed under a microscope at 400×.

Figure 2:
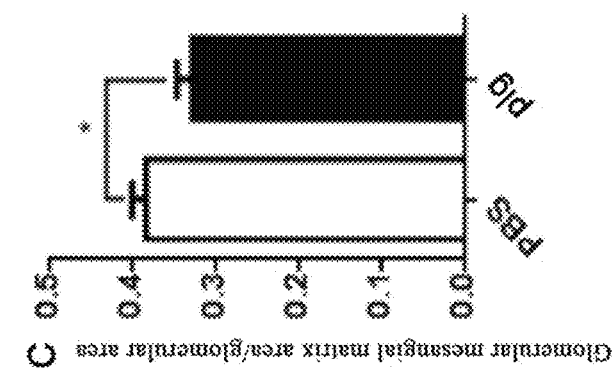
FIG. 2 shows the observed results of PAS staining of the kidneys after administration of plasminogen to 14-15-week-old db/db mice for 11 consecutive days.
Figure 2:
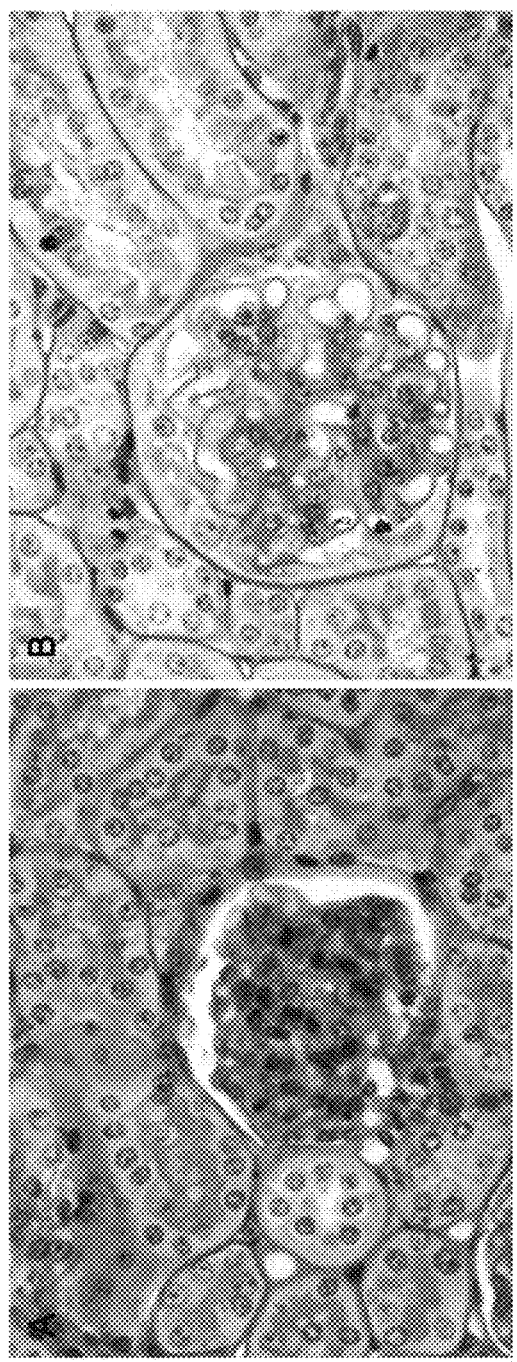

The results showed that compared with mice in the group administered with plasminogen (FIG. 2B), those in the control group administered with vehicle PBS (FIG. 2A) had obviously thickened glomerular basement membrane, obvious mesangial matrix hyperplasia and narrowed capillary lumen. Quantitative analysis showed that mice in the control group administered with vehicle PBS had significantly increased glomerular mesangial matrix, and the statistical difference was significant (FIG. 2C). This indicated that injection of plasminogen can significantly reduce the deposition of components of glomerular mesangial matrix, indicating that plasminogen can significantly promote the repair of renal injury of diabetic mice.

Example 3. Effect of Plasminogen on Body Weight of Late Diabetic Mice

Twenty male db/db mice aged 24-25 weeks were randomly divided into two groups, ten in the control group administered with vehicle PBS and ten in the group administered with plasminogen, respectively. The day when the experiment began was recorded on Day 0, and the mice were weighed and grouped. From the second day of the experiment, plasminogen or PBS was administered to the mice for 31 consecutive days, and the day was recorded as Day 1. Mice in the group administered with plasminogen were injected with plasminogen at a dose of 2 mg/0.2 mL/mouse/day via the tail vein, and an equal volume of PBS was administered to mice in the control group administered with vehicle PBS. The mice were weighted on days 0, 4, 7, 11, 16, 21, 26 and 31.

Figure 3:
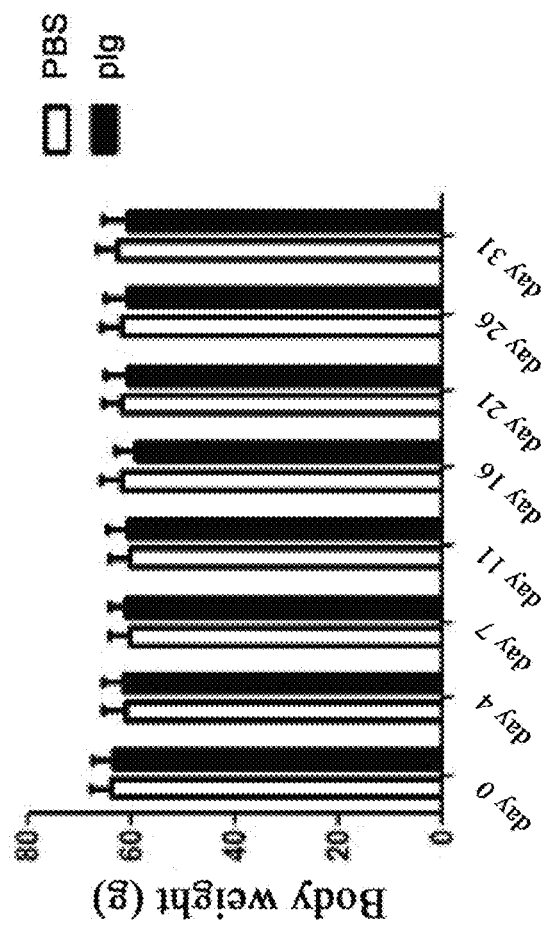
FIG. 3 shows changes in body weight after administration of plasminogen to 24-25-week-old db/db mice for 31 consecutive days.

The results showed that there was no significant difference in body weight between mice in the group administered with plasminogen and those in the control group administered with vehicle PBS on days 0, 4, 7, 11, 16, 21, 26 and 31 (FIG. 3), indicating that plasminogen has little effect on animal body weight.

Example 4. Effect of Plasminogen on Hyperplasia of Glomerular Mesangial Matrix and Basement Membrane in Late Diabetic Mice Twenty male db/db mice aged 24-25 weeks were randomly divided into two groups, ten in the control group administered with vehicle PBS and ten in the group administered with plasminogen, respectively. The day when the experiment began was recorded on Day 0, and the mice were weighed and grouped. From the second day of the experiment, plasminogen or PBS was administered to the mice for 31 consecutive days, and the day was recorded as Day 1. Mice in the group administered with plasminogen were injected with plasminogen at a dose of 2 mg/0.2 mL/mouse/day via the tail vein, and an equal volume of PBS was administered to mice in the control group administered with vehicle PBS. Mice were sacrificed on day 32, and the left kidneys were fixed in Carnoy fix solution for 24 hours. The fixed kidney tissues were paraffin-embedded after dehydration with alcohol gradient and permeabilization with xylene. The thickness of the sections was 5 μm. The sections were dewaxed and rehydrated, stained with hematoxylin and periodic acid-Schiff (PAS staining), differentiated with 1% hydrochloric acid in alcohol, and returned to blue with ammonia water. The sections were sealed after dehydration with alcohol gradient and permeabilization with xylene, and observed under a microscope at 400×.

Figure 4:
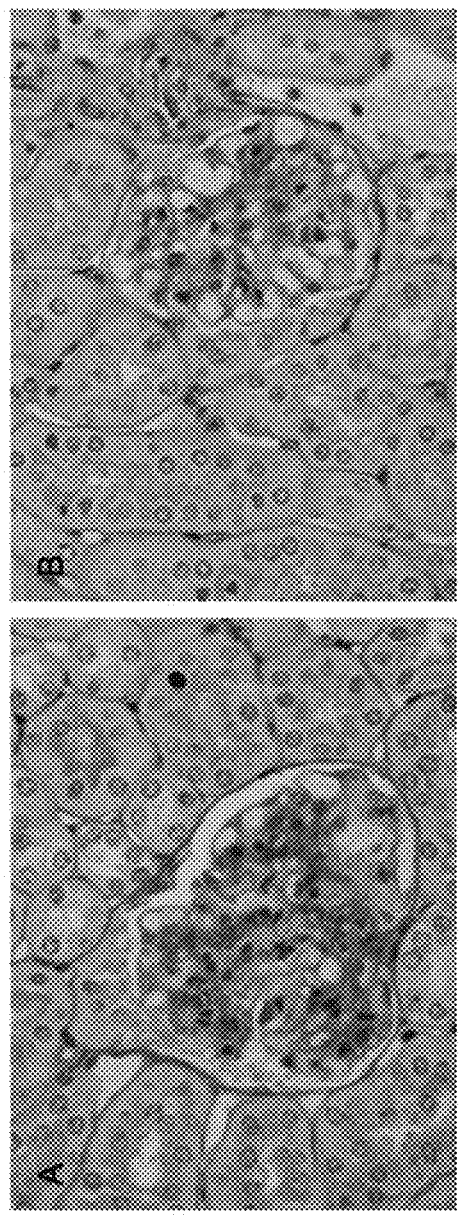
FIG. 4 shows the observed results of PAS staining of the kidneys after administration of plasminogen to 24-25-week-old db/db mice for 31 consecutive days.

The results showed that compared with mice in the group administered with plasminogen (FIG. 4B), those in the control group administered with vehicle PBS (FIG. 4A) had obviously thickened glomerular basement membrane, obvious mesangial matrix hyperplasia and narrowed capillary lumen. This indicated that injection of plasminogen can significantly reduce the deposition of components of glomerular mesangial matrix, indicating that plasminogen has a significant repair function on renal injury of diabetic mice.

Example 5. Protective Effect of Plasminogen on the Kidneys of Late Diabetic Mice Twenty male db/db mice aged 24-25 weeks were randomly divided into two groups, ten in the control group administered with vehicle PBS and ten in the group administered with plasminogen, respectively. The day when the experiment began was recorded on Day 0, and the mice were weighed and grouped. From the second day of the experiment, plasminogen or PBS was administered to the mice for 31 consecutive days, and the day was recorded as Day 1. Mice in the group administered with plasminogen were injected with plasminogen at a dose of 2 mg/0.2 mL/mouse/day via the tail vein, and an equal volume of PBS was administered to mice in the control group administered with vehicle PBS. Mice were sacrificed on day 32, and the kidneys were fixed in 10% neutral formalin fix solution for 24 hours. The fixed kidneys were paraffin-embedded after dehydration with alcohol gradient and permeabilization with xylene. The thickness of the tissue sections was 5 nm. The sections were dewaxed and rehydrated, stained with hematoxylin and eosin (HE staining), differentiated with 1% hydrochloric acid in alcohol, and returned to blue with ammonia water. The sections were sealed after dehydration with alcohol gradient and observed under a microscope at 200×.

Figure 5:
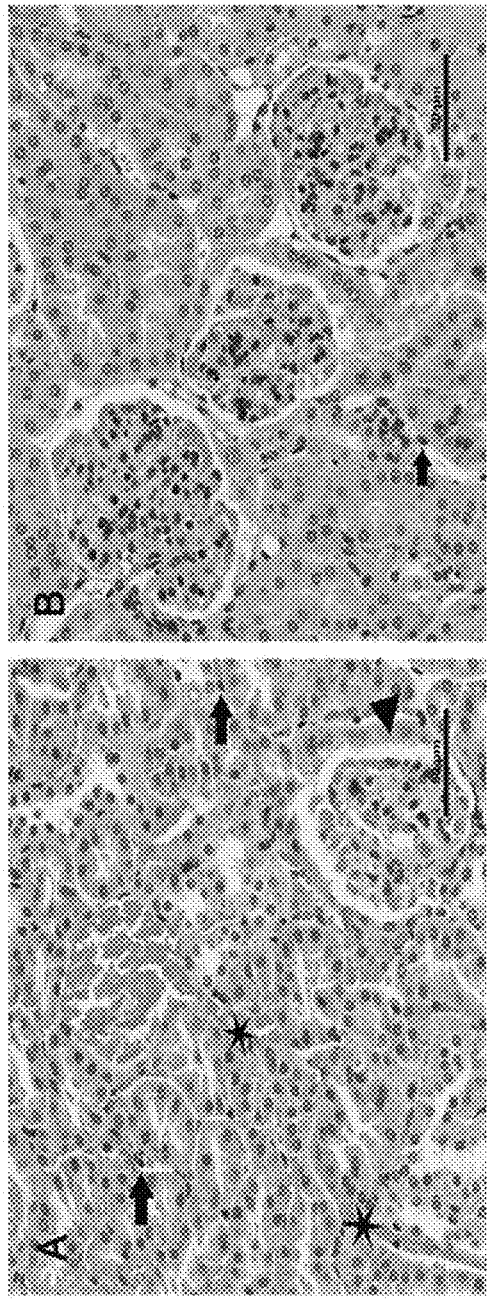
FIG. 5 shows the observed results of HE staining of the kidneys after administration of plasminogen to 24-25-week-old db/db mice for 31 consecutive days.

The HE staining results showed that a little glomerular atrophy, dysplasia, vacuolization of tubular epithelial cells and a little inflammatory cell infiltration (↑) can be observed in both mice in the control group administered with vehicle PBS (FIG. 5A) and those in the group administered with plasminogen (FIG. 5B). However, a large area of renal interstitial hyperemia (*) and glomerular parietal basement membrane hyperplasia (▲) were also observed in mice in the control group administered with vehicle PBS, and the parietal basement membrane hyperplasia of mice in the group administered with plasminogen was milder than that of mice in the control group administered with vehicle PBS. In addition, right kidney edema was observed in one mouse in the control group administered with vehicle PBS when dissecting. This indicated that the degree of renal injury is improved after administration of plasminogen.

Example 6. Plasminogen Promotes Fibrin Hydrolysis in the Kidneys of Late Diabetic Mice Twenty male db/db mice aged 24-25 weeks were randomly divided into two groups, ten in the control group administered with vehicle PBS and ten in the group administered with plasminogen, respectively. The day when the experiment began was recorded on Day 0, and the mice were weighed and grouped. From the second day of the experiment, plasminogen or PBS was administered to the mice for 31 consecutive days, and the day was recorded as Day 1. Mice in the group administered with plasminogen were injected with plasminogen at a dose of 2 mg/0.2 mL/mouse/day via the tail vein, and an equal volume of PBS was administered to mice in the control group administered with vehicle PBS. Mice were sacrificed on day 32, and the kidneys were fixed in 10% neutral formalin fix solution for 24 hours. The fixed kidney tissues were paraffin-embedded after dehydration with alcohol gradient and permeabilization with xylene. The thickness of the tissue sections was 5 µm. The sections were dewaxed and rehydrated and washed with water once. The sections were incubated with 3% hydrogen peroxide for 15 minutes and wash with water twice for 5 minutes each time. The sections were blocked with 10% normal goat serum solution (Vector laboratories, Inc., USA) for 1 hour; and after the time was up, the goat serum solution was discarded, and the tissues were circled with a PAP pen. The sections were incubated with rabbit anti-mouse fibrin (fibrinogen) antibody (Abcam) overnight at 4° C. and washed with TBS twice for 5 minutes each time. The sections were incubated with a secondary antibody, goat anti-rabbit IgG (HRP) antibody (Abcam), for 1 hour at room temperature and washed with TBS twice for 5 minutes each time. The sections were developed with a DAB kit (Vector laboratories, Inc., USA). After washing with water three times, the sections were counterstained with hematoxylin for 30 seconds and flushed with running water for 5 minutes. After gradient dehydration, permeabilization and sealing, the sections were observed under a microscope at 200×.

Fibrinogen is the precursor of fibrin, and in the presence of tissue injury, as a stress response to the body's injury, fibrinogen is hydrolyzed into fibrin and deposited at the injury site[29-31]. Therefore, the local fibrin level at the injury site can be used as a sign of the degree of injury.

Figure 6:
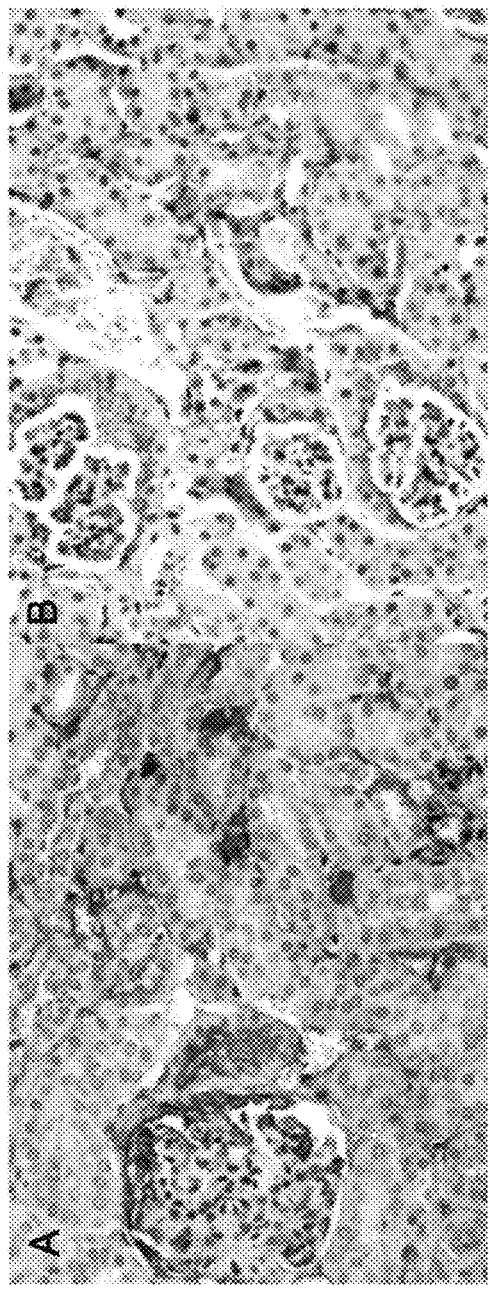
FIG. 6 shows the observed results of fibrin immunostaining of the kidneys after administration of plasminogen to 24-25-week-old db/db mice for 31 consecutive days.

The results showed the fibrinogen-positive staining in the group administered with plasminogen (FIG. 6B) was lighter than that in the control group administered with vehicle PBS (FIG. 6A). This indicated that injection of plasminogen can significantly reduce the deposition of fibrin in the kidneys of diabetic mice, reflecting that plasminogen has a significant repair effect on the renal injury of diabetic mice.

Example 7. Plasminogen Promotes the Expression of Bcl-2, an Apoptosis Inhibitory Protein, in the Kidneys of Late Diabetic Mice Twenty male db/db mice aged 24-25 weeks were randomly divided into two groups, ten in the control group administered with vehicle PBS and ten in the group administered with plasminogen, respectively. The day when the experiment began was recorded on Day 0, and the mice were weighed and grouped. From the second day of the experiment, plasminogen or PBS was administered to the mice for 31 consecutive days, and the day was recorded as Day 1. Mice in the group administered with plasminogen were injected with plasminogen at a dose of 2 mg/0.2 mL/mouse/day via the tail vein, and an equal volume of PBS was administered to mice in the control group administered with vehicle PBS. Mice were sacrificed on day 32, and the kidneys were fixed in 10% neutral formalin fix solution for 24 hours. The fixed kidney tissues were paraffin-embedded after dehydration with alcohol gradient and permeabilization with xylene. The thickness of the tissue sections was 5 µm. The sections were dewaxed and rehydrated and washed with water once. The sections were incubated with 3% hydrogen peroxide for 15 minutes and wash with water twice for 5 minutes each time. The sections were blocked with 10% normal goat serum solution (Vector laboratories, Inc., USA) for 1 hour; and after the time was up, the goat serum solution was discarded, and the tissues were circled with a PAP pen. The sections were incubated with rabbit anti-mouse Bcl-2 antibody (Abcam) at 4° C. overnight and washed with TBS twice for 5 minutes each time. The sections were incubated with a secondary antibody, goat anti-rabbit IgG (HRP) antibody (Abcam), for 1 hour at room temperature and washed with TBS twice for 5 minutes each time. The sections were developed with a DAB kit (Vector laboratories, Inc., USA). After washing with water three times, the sections were counterstained with hematoxylin for 30 seconds and flushed with running water for 5 minutes. After gradient dehydration, permeabilization and sealing, the sections were observed under a microscope at 200×.

Figure 7:
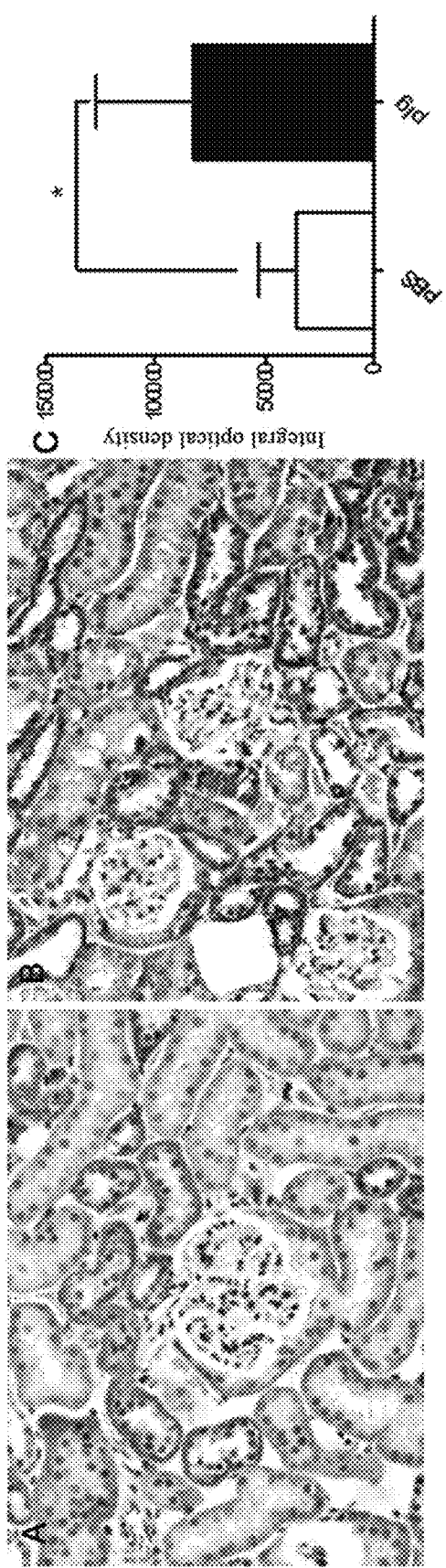
FIG. 7 shows the observed results of Bcl-2 immunostaining of the kidneys after administration of plasminogen to 24-25-week-old db/db mice for 31 consecutive days.

Bcl-2 is an apoptosis inhibitory protein, and its expression will be down-regulated under the action of an apoptosis stimulating factor[32, 33]. The Bcl-2 immunohistochemical results showed that the positive expression staining of tubular epithelial cells in mice in the group administered with plasminogen (FIG. 7B) was significantly darker than that of tubular epithelial cells in those in the control group administered with vehicle PBS (FIG. 7A), and the former had a wider range of staining. The results of quantitative analysis were consistent with the observations, and there were significant differences (as shown in FIG. 7C). This indicated that plasminogen can promote the expression of Bcl-2, an apoptosis inhibitory molecule, in the kidneys of diabetic mice, and thus inhibit the apoptosis in the kidney tissues of diabetic mice.

Example 8. Plasminogen Reduces Renal Injury of Late Diabetic Mice

Eight male db/db mice aged 24-25 weeks were randomly divided into two groups, four in the control group administered with vehicle PBS and four in the group administered with plasminogen, respectively. The day when the experiment began was recorded on Day 0, and the mice were weighed and grouped. From the second day of the experiment, plasminogen or PBS was administered to the mice for 31 consecutive days, and the day was recorded as Day 1. Mice in the group administered with plasminogen were injected with plasminogen at a dose of 2 mg/0.2 mL/mouse/day via the tail vein, and an equal volume of PBS was administered to mice in the control group administered with vehicle PBS. Detection of physiological indexes was finished on day 32, mice were sacrificed, and the kidneys were fixed in 10% neutral formalin fix solution for 24 hours. The fixed kidney tissues were paraffin-embedded after dehydration with alcohol gradient and permeabilization with xylene. The thickness of the tissue sections was 5 µm. The sections were dewaxed and rehydrated and washed with water once. The sections were incubated with 3% hydrogen peroxide for 15 minutes and wash with water twice for 5 minutes each time. The sections were incubated with goat anti-mouse IgM (HRP) antibody (Abcam) for 1 hour at room temperature and washed with TBS twice for 5 minutes each time. The sections were developed with a DAB kit (Vector laboratories, Inc., USA). After washing with water three times, the sections were counterstained with hematoxylin for 30 seconds and flushed with running water for 5 minutes. After gradient dehydration, permeabilization and sealing, the sections were observed under a microscope at 400×.

IgM antibodies play an important role during the clearance of apoptotic and necrotic cells, and the local level of IgM antibodies at the injury site in tissues and organs are positively correlated with the degree of injury[34-36]. Therefore, detection of local level of IgM antibodies in tissues and organs can reflect the injury of the tissues and organs.

Figure 8:
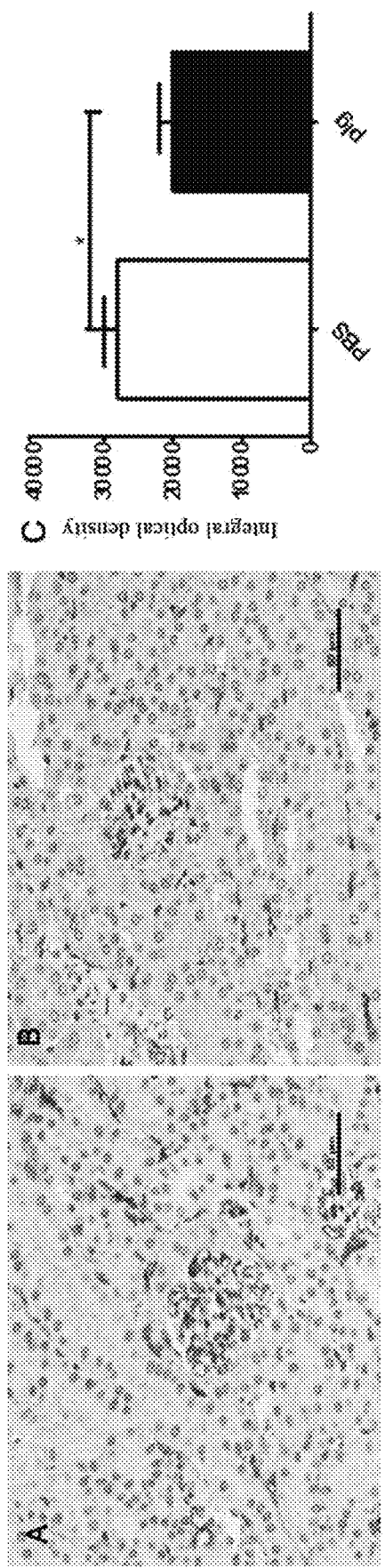
FIG. 8 shows the observed results of IgM immunostaining of the kidneys after administration of plasminogen to 24-25-week-old db/db mice for 31 consecutive days.

The results showed that the positive staining of glomerular IgMs in mice in the group administered with plasminogen (FIG. 8B) was lighter than that of glomerular IgMs in mice in the control group administered with vehicle PBS, and the range was smaller than the control group (FIG. 8A). The results of quantitative analysis were consistent with the observations, and the statistical difference was significant. This indicated that the glomerular injury is remarkably improved after injection of plasminogen, reflecting the significant repair effect of plasminogen on the renal injury of diabetic mice.

Example 9. Plasminogen Reduces the Fibrin Level in Liver Tissues in Late Diabetes Mellitus Ten male db/db mice aged 24-25 weeks were randomly divided into two groups, five in the control group administered with vehicle PBS and five in the group administered with plasminogen, respectively. The day when the experiment began was recorded on Day 0, and the mice were weighed and grouped. From the second day of the experiment, plasminogen or PBS was administered to the mice for 31 consecutive days, and the day was recorded as Day 1. Mice in the group administered with plasminogen were injected with plasminogen at a dose of 2 mg/0.2 mL/mouse/day via the tail vein, and an equal volume of PBS was administered to mice in the control group administered with vehicle PBS. Mice were sacrificed on day 32, and liver tissues were fixed in 10% neutral formalin fix solution for 24 hours. The fixed liver tissues were paraffin-embedded after dehydration with alcohol gradient and permeabilization with xylene. The thickness of the tissue sections was 5 μm. The sections were dewaxed and rehydrated and washed with water once. The sections were incubated with 3% hydrogen peroxide for 15 minutes and wash with water twice for 5 minutes each time. The sections were blocked with 10% normal goat serum solution (Vector laboratories, Inc., USA) for 1 hour; and after the time was up, the goat serum solution was discarded, and the tissues were circled with a PAP pen. The sections were incubated with rabbit anti-mouse fibrin (fibrinogen) antibody (Abcam) overnight at 4° C. and washed with TBS twice for 5 minutes each time. The sections were incubated with a secondary antibody, goat anti-rabbit IgG (HRP) antibody (Abcam), for 1 hour at room temperature and washed with TBS twice for 5 minutes each time. The sections were developed with a DAB kit (Vector laboratories, Inc., USA). After washing with water three times, the sections were counterstained with hematoxylin for 30 seconds and flushed with running water for 5 minutes. After gradient dehydration, permeabilization and sealing, the sections were observed under a microscope at 200×.

Fibrinogen is the precursor of fibrin, and in the presence of tissue injury, as a stress response to the body's injury, fibrinogen is hydrolyzed into fibrin[29-31]. Therefore, the local fibrin level in tissues and organs can be used as a sign of the degree of injury in the tissues and organs.

Figure 9:
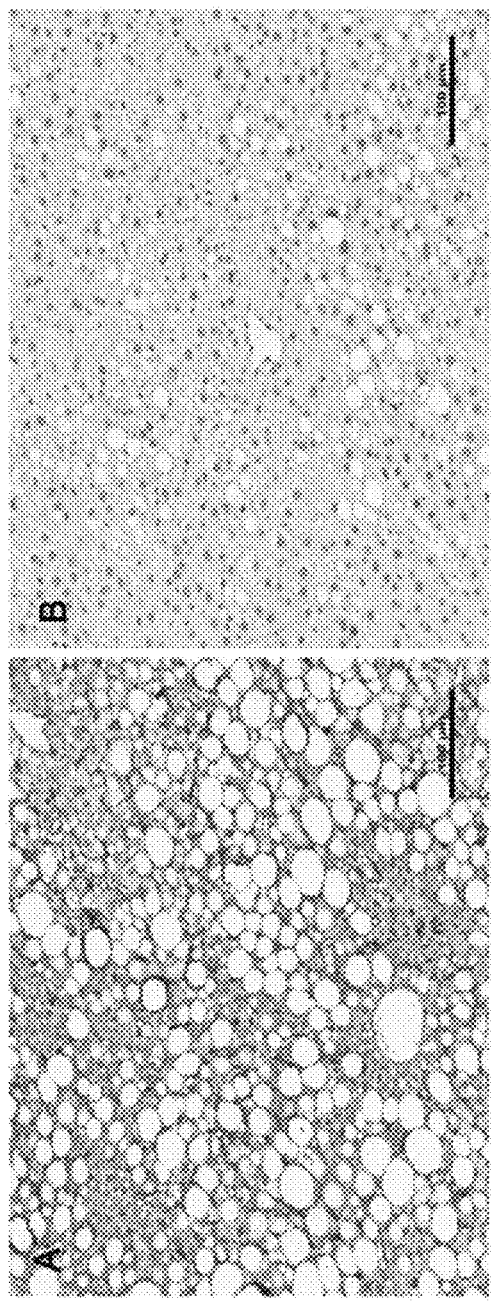
FIG. 9 shows the observed results of fibrin immunostaining of the liver after administration of plasminogen to 24-25-week-old db/db mice for 31 consecutive days.

The study found that compared with mice in the control group administered with vehicle PBS (FIG. 9A), those in the group administered with plasminogen (FIG. 9B) had a lighter fibrin-positive staining in the liver tissues, indicating that injection of plasminogen can significantly reduce the deposition of fibrin in the liver of diabetic mice, reflecting the significant repair function of plasminogen on the liver injury of diabetic mice.

Example 10. Plasminogen Promotes the Inflammation Repair of the Liver Tissues of Late Diabetic Mice Ten male db/db mice aged 24-25 weeks were randomly divided into two groups, five in the control group administered with vehicle PBS and five in the group administered with plasminogen, respectively. The day when the experiment began was recorded on Day 0, and the mice were weighed and grouped. From the second day of the experiment, plasminogen or PBS was administered to the mice for 31 consecutive days, and the day was recorded as Day 1. Mice in the group administered with plasminogen were injected with plasminogen at a dose of 2 mg/0.2 mL/mouse/day via the tail vein, and an equal volume of PBS was administered to mice in the control group administered with vehicle PBS. Mice were sacrificed 31 days after administration of plasminogen, and liver tissues were fixed in 10% neutral formalin fix solution for 24 hours. The fixed liver tissues were paraffin-embedded after dehydration with alcohol gradient and permeabilization with xylene. The thickness of the tissue sections was 5 μm. The sections were dewaxed and rehydrated and washed with water once. The sections were incubated with 3% hydrogen peroxide for 15 minutes and wash with water twice for 5 minutes each time. The sections were blocked with 10% normal goat serum (Vector laboratories, Inc., USA) for 1 hour, and after the time was up, the serum was thrown away, and the tissues were circled with a PAP pen. The sections were incubated with a rabbit polyclonal antibody against F4/80 (Abcam) overnight at 4° C. and washed with TBS twice for 5 minutes each time. The sections were incubated with a secondary antibody, goat anti-rabbit IgG (HRP) antibody (Abcam), for 1 hour at room temperature and washed with TBS twice. The sections were developed with a DAB kit (Vector laboratories, Inc., USA). After washing with water three times, the sections were counterstained with hematoxylin for 30 seconds and flushed with running water for 5 minutes. After gradient dehydration, permeabilization and sealing, the sections were observed under a microscope at 400×.

F4/80 is a macrophage marker. Macrophages, as the main phagocytic cells in the inflammatory phase, are responsible for the removal of necrotic debris of tissues and cells and pathogens at the body site of injury; therefore, the amount of local macrophages can indicate the degree and stage of an inflammatory response.

Figure 10:
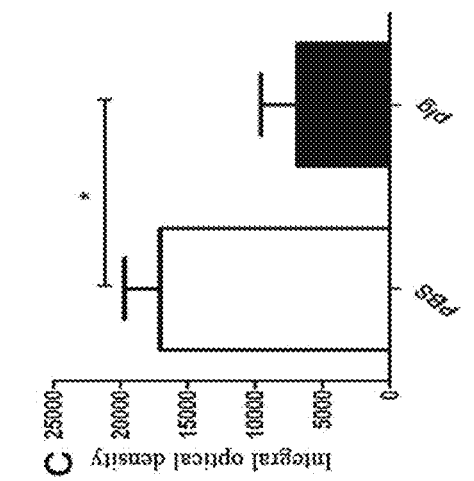
FIG. 10 shows the observed results of F4/80 immunostaining of the liver after administration of plasminogen to 24-25-week-old db/db mice for 31 consecutive days.
Figure 10:
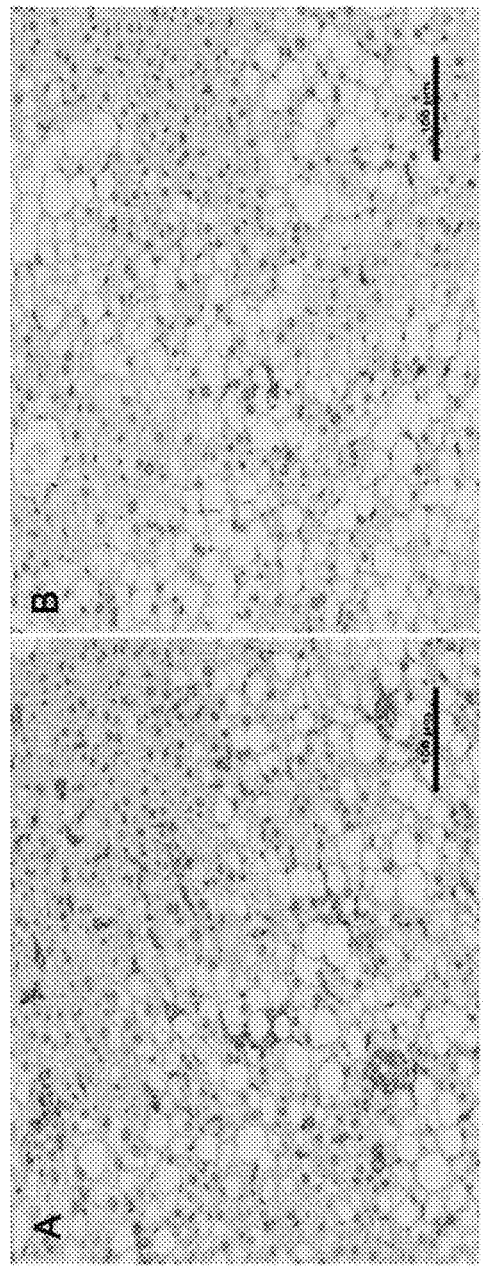

The experiment found that compared with mice in the control group administered with vehicle PBS (FIG. 10A), the F4/80 positive expression was remarkably reduced in mice in the group administered with plasminogen (FIG. 10B), indicating that inflammation of the liver tissues is reduced after administration of plasminogen. FIG. 10C shows the results of quantitative analysis of F4/80 immunohistochemical positive expression, in which the expression of F4/80 in mice in the group administered with plasminogen was significantly reduced with statistical difference, indicating that injection of plasminogen can significantly promote the repair of liver inflammation of diabetic mice.

Example 11. Plasminogen Alleviates Retinal Injury of Late Diabetic Mice

Twenty male db/db mice aged 24-25 weeks were randomly divided into two groups, ten in the control group administered with vehicle PBS and ten in the group administered with plasminogen, respectively. The day when the experiment began was recorded on Day 0, and the mice were weighed and grouped. From the second day of the experiment, plasminogen or PBS was administered to the mice for 31 consecutive days, and the day was recorded as Day 1. Mice in the group administered with plasminogen were injected with plasminogen at a dose of 2 mg/0.2 mL/mouse/day via the tail vein, and an equal volume of PBS was administered to mice in the control group administered with vehicle PBS. Mice were sacrificed on day 32, and the left eyeballs were fixed in paraformaldehyde fix solution for 24 hours. The retina was detached from the fixed eyeballs and placed in an 1 mL EP tube containing 3% pancreatin (Solarbio), and shaken for digestion in a shaker at 37° C. for 2-3 h. After the retina was softened and detached, the retina was carefully transferred into an EP tube filled with distilled water and shaken in a shaker at 37° C. for 2-3 h to detach excess tissues from the retina. The retina was gently pipetted, leaving only the blood vessel layer, and then spread on a glass slide and air dried. The retina was stained in periodic acid-Schiff solution (PAS staining), differentiated with 1% hydrochloric acid in alcohol, and returned to blue with ammonia water. The slide was sealed after dehydration with alcohol gradient and permeabilization with xylene, and observed under a microscope at 400×.

Related studies have shown that diabetes mellitus can cause retinopathy, resulting in hyperplasia of retinal vascular endothelial cells, loss of pericytes and formation of cell-free vessels[37,38].

Figure 11:
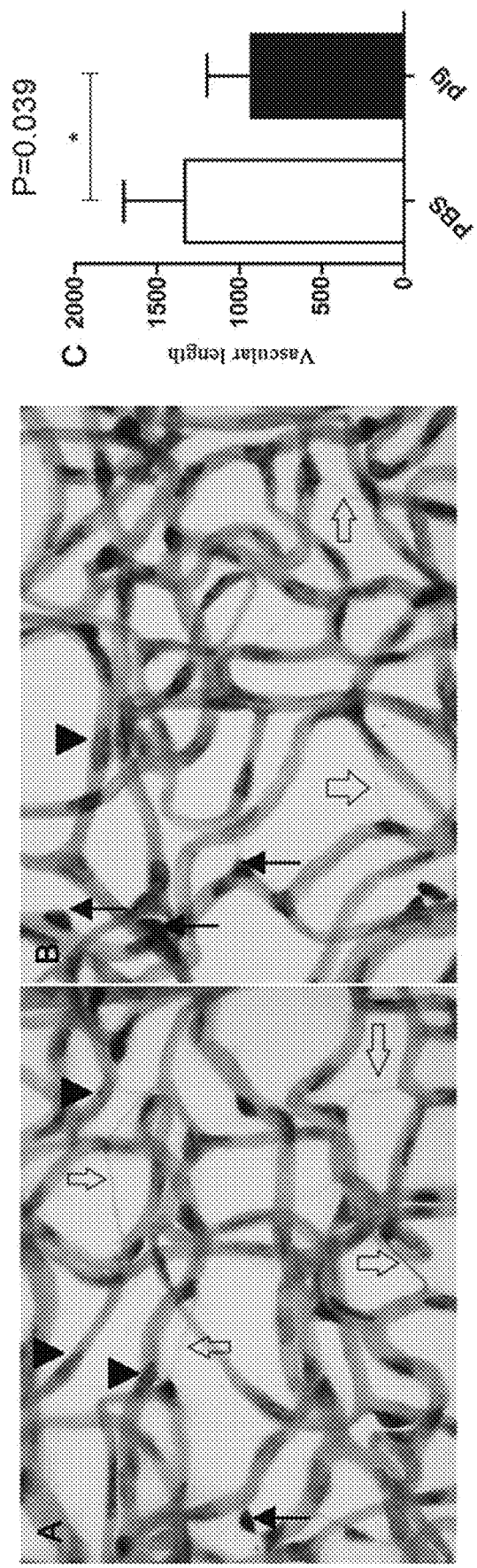
FIG. 11 shows the observed results of PAS staining of the retina after administration of plasminogen to 24-25-week-old db/db mice for 31 consecutive days.

From the experimental results, it can be seen that compared with the plasminogen group (FIG. 11B), the retinal capillary diameters of the db/db mice in the control group administered with vehicle PBS (FIG. 11A) were different, in which the vascular walls were thickened and darkly stained, the vascular endothelial cells (▲) were proliferated, and the pericytes (↓) were decreased remarkably; however, mice in the group administered with plasminogen (FIG. 11B) had remarkably reduced pathological changes. It was found from quantitative analysis that compared with mice in the control group administered with vehicle PBS, those in the group administered with plasminogen had significantly reduced cell-free capillary length (FIG. 11C), and the statistical analysis results showed a significant difference. This indicated that plasminogen can significantly promote the repair of retinal injury of late diabetic mice.

Example 12. Plasminogen Promotes Dissolution of Microthrombi Caused by Diabetes Mellitus Ten male db/db mice aged 24-25 weeks were randomly divided into two groups, five in the control group administered with vehicle PBS and five in the group administered with plasminogen, respectively. The day when the experiment began was recorded on Day 0, and the mice were weighed and grouped. From the second day of the experiment, plasminogen or PBS was administered to the mice for 15 consecutive days, and the day was recorded as Day 1. Mice in the group administered with plasminogen were injected with plasminogen at a dose of 2 mg/0.2 mL/mouse/day via the tail vein, and an equal volume of PBS was administered to mice in the control group administered with vehicle PBS. On day 16, blood was taken from the removed eyeballs, and the whole blood was left standing to obtain serum for detecting the D-dimer content in the blood.

Figure 12:
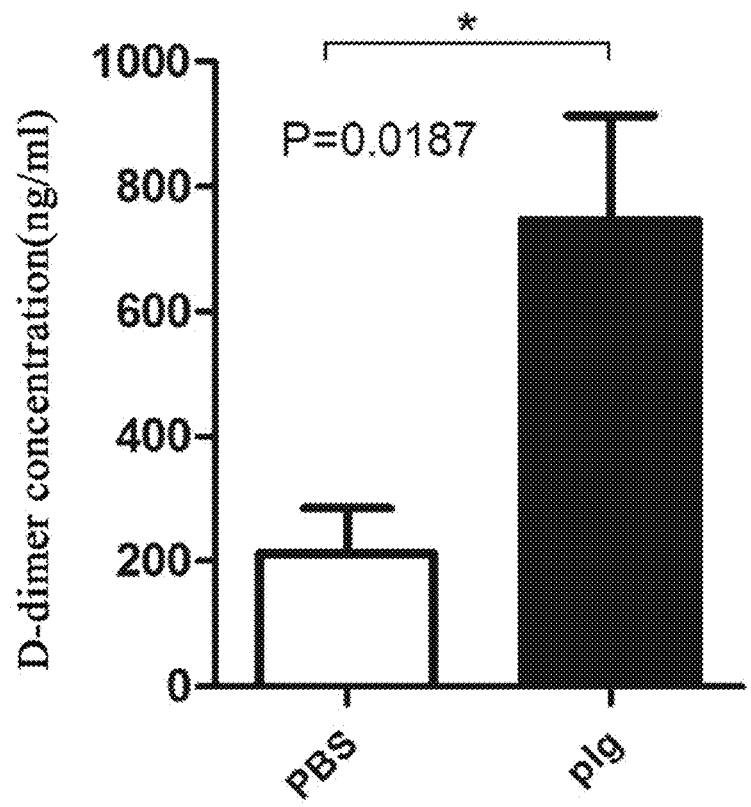
FIG. 12 shows the detection results of serum D-dimer content after administration of plasminogen to 24-25-week-old db/db mice for 15 consecutive days.

The results showed that the D-dimer content in the serum of mice in the group administered with plasminogen was significantly increased after 15 days of administration (FIG. 12), indicating that after administration of plasminogen, microthrombi caused by diabetes mellitus were significantly dissolved.

Example 13. Plasminogen Promotes the Repair of the Ability of Late Diabetic Mice with Nerve Injury to Respond to Mechanical Allodynia Ten male db/db mice aged 24-25 weeks were randomly divided into two groups, five in the control group administered with vehicle PBS and five in the group administered with plasminogen, respectively. The day when the experiment began was recorded on Day 0, the mice were weighed and grouped, and the physiological experiment was initiated. From the second day of the experiment, plasminogen or PBS was administered to the mice for 15 consecutive days, and the day was recorded as Day 1. Mice in the group administered with plasminogen were injected with plasminogen at a dose of 2 mg/0.2 mL/mouse/day via the tail vein, and an equal volume of PBS was administered to mice in the control group administered with vehicle PBS. On days 0, 4, 7, 11 and 16 after administration of plasminogen, animals were detected for their sensitivity to mechanical injury using Von-Frey filaments (Stoelting, USA). With 2.0 g force as the starting force, the left foot was first detected. If there were 2 paw withdrawals for 5 stimulations, it was positive; and if it was positive, the right foot was then stimulated with a smaller force. If it was negative, the right foot was stimulated with a larger force, the left and right feet were thus alternately stimulated for a total of 6 stimulations at a stimulation interval of 5 minutes, and then the 50% paw withdrawal threshold was calculated according to the method introduced in S. R. Chaplan et. al. (1994)[39].

Figure 13:
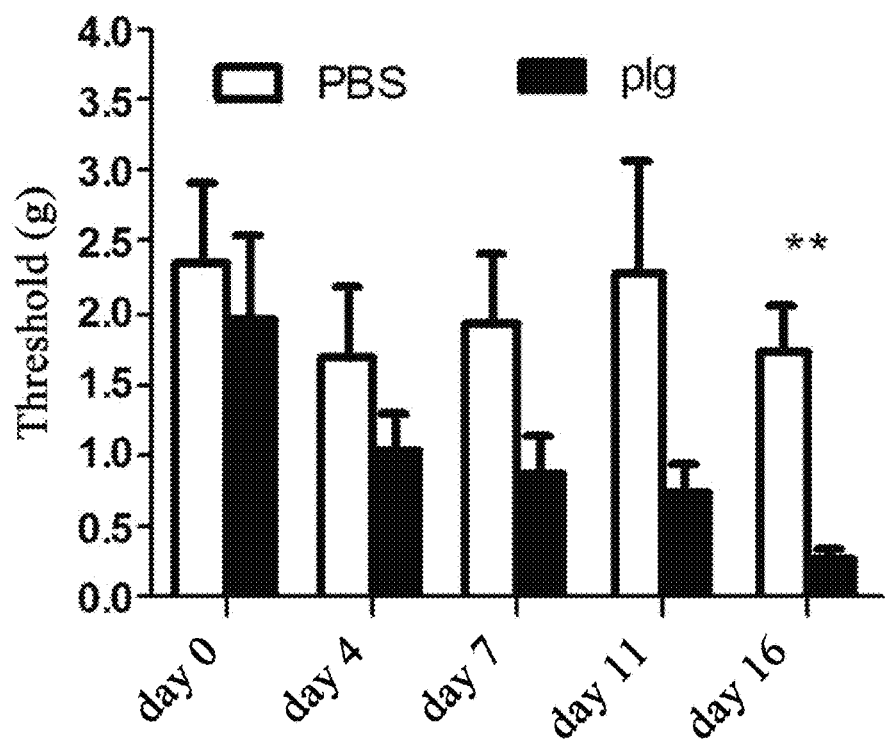
FIG. 13 shows the detection results of the ability to respond to mechanical allodynia on days 0, 4, 7, 11 and 16 after administration of plasminogen to 24-25-week-old db/db mice.

The study found that compared with mice in the control group administered with vehicle PBS, diabetic mice in the group administered with plasminogen showed uniform increase in the response to mechanical allodynia, and an extremely significant difference was found on day 16 compared with mice in the control group administered with vehicle PBS (FIG. 13), indicating that plasminogen repairs the ability of late diabetic mice with nerve injury to respond to mechanical allodynia.

Example 14. Plasminogen Repairs Response of Late Diabetic Mice with Nerve Injury to Cold Stimulation Ten male db/db mice aged 24-25 weeks were randomly divided into two groups, five in the control group administered with vehicle PBS and five in the group administered with plasminogen, respectively. The day when the experiment began was recorded on Day 0, the mice were weighed and grouped, and the physiological experiment was initiated. From the second day of the experiment, plasminogen or PBS was administered to the mice for 15 consecutive days, and the day was recorded as Day 1. Mice in the group administered with plasminogen were injected with plasminogen at a dose of 2 mg/0.2 mL/mouse/day via the tail vein, and an equal volume of PBS was administered to mice in the control group administered with vehicle PBS. On days 0, 4, 7, 11 and 16 after administration, a drop of acetone was squeezed out with a needleless syringe and the planta of each db/db mouse was slightly touched to cover the entire planta with acetone. Starting from the left foot, the left and right feet were stimulated alternately every 3 minutes for a total of 10 stimulations, and the number of paw withdrawals was counted.

Percentage of response=number of paw withdrawals/ number of stimulations×100%.

Figure 14:
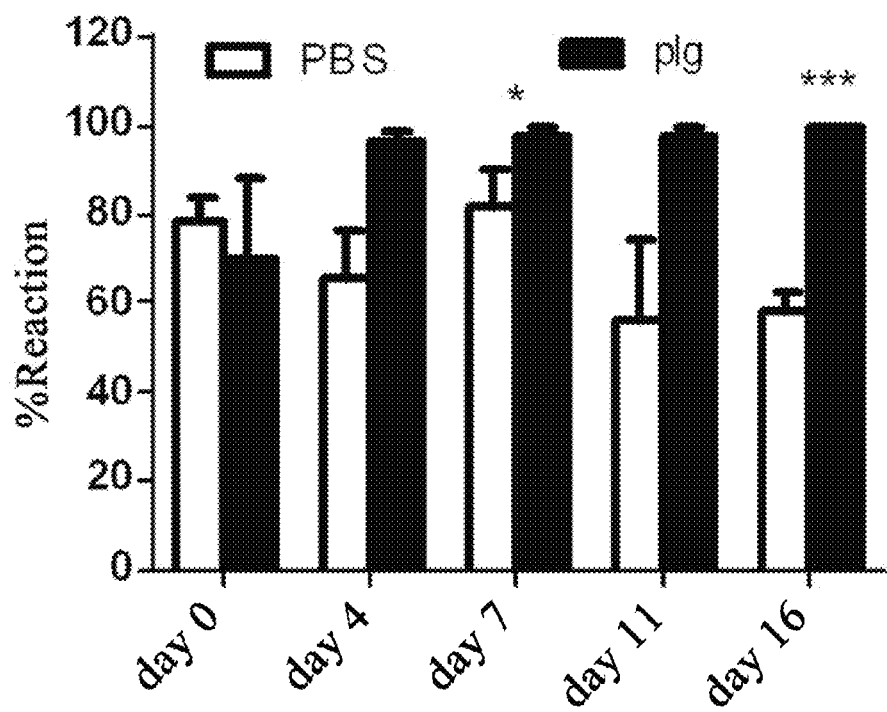
FIG. 14 shows the detection results of the ability to respond to cold stimulation on days 0, 4, 7, 11 and 16 after administration of plasminogen to 24-25-week-old db/db mice.

The experimental results showed that there was no significant difference in the response to acetone stimulation between mice in the group administered with plasminogen and those in the control group administered with vehicle PBS on days 0 and 4; however, a significant difference was observed from day 7, and an extremely significant difference was observed on day 16, and the P value was <0.0001 (FIG. 14), indicating that after 15 days of administration, diabetic mice almost completely restored response to cold stimulation, suggesting that plasminogen extremely significantly repairs the ability of nerves to response to cold stimulation in late diabetes mellitus.

Example 15. Plasminogen Promotes the Repair of Myocardial Injury in Late Diabetes Mellitus Twenty-eight male db/db mice aged 24-25 weeks were randomly divided into two groups, twelve in the control group administered with vehicle PBS and sixteen in the group administered with plasminogen, respectively. The day when the experiment began was recorded on Day 0, and the mice were weighed and grouped. From the second day of the experiment, plasminogen or PBS was administered to the mice for 31 consecutive days, and the day was recorded as Day 1. Mice in the group administered with plasminogen were injected with plasminogen at a dose of 2 mg/0.2 mL/mouse/day via the tail vein, and an equal volume of PBS was administered to mice in the control group administered with vehicle PBS. On day 32, blood was taken from the removed eyeballs and centrifuged at 3500 r/min for 15-20 minutes, and the supernatant was used for the determination of cardiac troponin I concentration.

Figure 15:
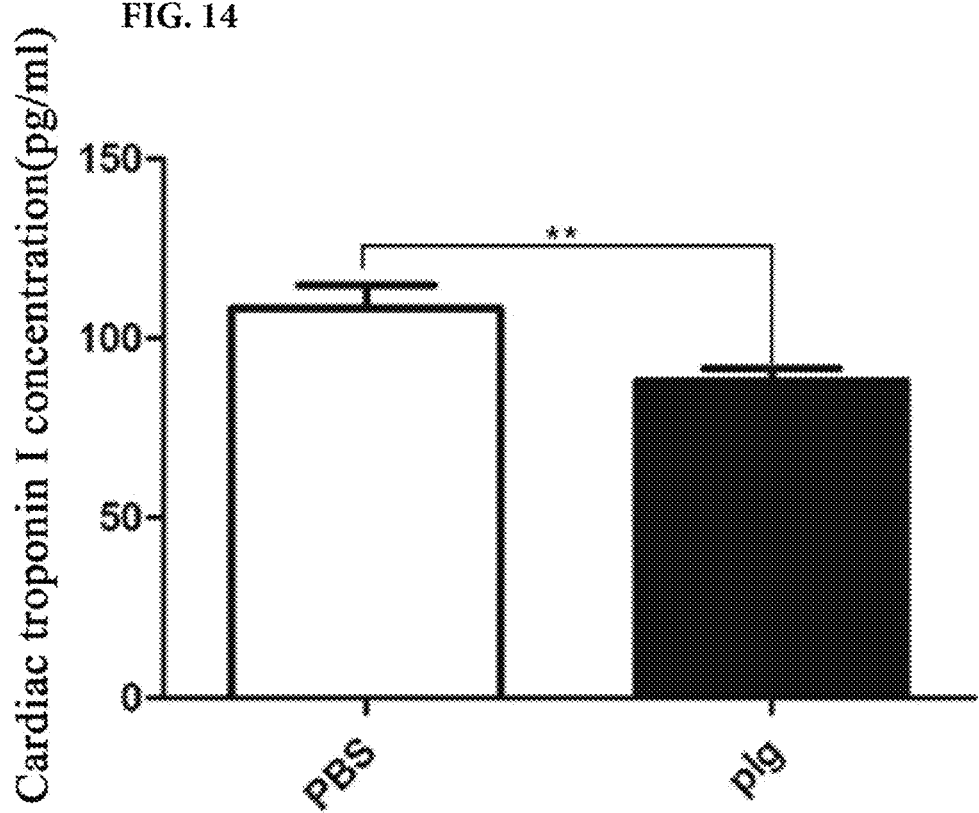
FIG. 15 shows the detection results of cardiac troponin I concentration in serum after administration of plasminogen to 24-25-week-old db/db mice for 31 days.

Cardiac troponin I (CTNI) is an important marker of myocardial injury, and its serum concentration can reflect the extent of myocardial injury[40]. The results showed that the cardiac troponin I concentration in the group administered with plasminogen was remarkably lower than that in the control group administered with vehicle PBS, and there was an extremely significant statistical difference (FIG. 15). This indicated that plasminogen can extremely significantly promote the repair of myocardial injury of late diabetic mice.

Example 16. Plasminogen Reduces the Fibrin Level in Nerve Tissues of Late Diabetic Mice with Nerve Injury Ten male db/db mice aged 24-25 weeks were randomly divided into two groups, five in the control group administered with vehicle PBS and five in the group administered with plasminogen, respectively. The day when the experiment began was recorded on Day 0, and the mice were weighed and grouped. From the second day of the experiment, plasminogen or PBS was administered to the mice for 15 consecutive days, and the day was recorded as Day 1. Mice in the group administered with plasminogen were injected with plasminogen at a dose of 2 mg/0.2 mL/mouse/day via the tail vein, and an equal volume of PBS was administered to mice in the control group administered with vehicle PBS. Mice were sacrificed on day 16, and sciatic nerves were fixed in 10% neutral formalin fix solution for 24 hours. The fixed sciatic nerves were paraffin-embedded after dehydration with alcohol gradient and permeabilization with xylene. The thickness of the tissue sections was 5 µM. The sections were dewaxed and rehydrated and washed with water once, and then the tissues were circled with a PAP pen. The sections were incubated with hydrogen peroxide diluted with 3% TBS for 15 minutes, and washed with water three times. The sections were blocked with 10% normal goat serum (Vector laboratories, Inc., USA) for 1 hour, and excess serum was aspirated. The sections were incubated with rabbit anti-mouse fibrin (fibrinogen) antibody (Abcam) for 1 hour at room temperature or overnight at 4° C. and washed with TBS three times. The sections were incubated with a secondary antibody, goat anti-rabbit IgG (HRP) antibody (Abcam), for 1 hour at room temperature and washed with TBS three times. The sections were developed with a DAB kit (Vector laboratories, Inc., USA). After washing with water three times, the sections were counterstained with hematoxylin for 30 seconds and flushed with running water for 5 minutes. After gradient dehydration, permeabilization and sealing, the sections were observed under a microscope at 400×.

Fibrinogen is the precursor of fibrin, and in the presence of tissue injury, as a stress response to the body's injury, fibrinogen is hydrolyzed into fibrin. Therefore, fibrin levels can be used as a sign of the degree of injury. Fibrin is also the main component of thrombosis after tissue is injured. Therefore, fibrin levels can also be used as a marker of thrombi.

Figure 16:
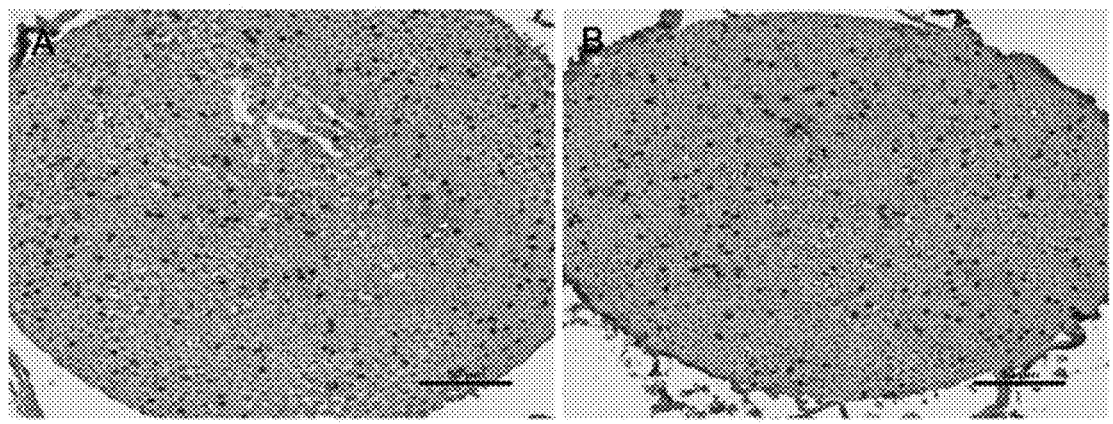
FIG. 16 shows the observed results of fibrin immumohistochemical staining of the sciatic nerve after administration of plasminogen to 24-25-week-old late diabetic mice with nerve injury for 15 days.

The study found that compared with mice in the control group administered with vehicle PBS (FIG. 16A), those in the group administered with plasminogen (FIG. 16B) had a decreased level of fibrin in the sciatic nerve, indicating that plasminogen has the function of degrading fibrin level and the injury has been repaired to a certain degree, and also indicating that plasminogen can promote the dissolution of thrombi around nerve tissues.

Example 17. Plasminogen Promotes the Repair of Liver Injury of Diabetic Mice

Nine male db/db mice aged 25-28 weeks were randomly divided into two groups, three in the control group administered with vehicle PBS and six in the group administered with plasminogen, respectively. The day when the experiment began was recorded on Day 0, and the mice were weighed and grouped. From the second day of the experiment, plasminogen or PBS was administered to the mice for 31 consecutive days, and the day was recorded as Day 1. Mice in the group administered with plasminogen were injected with plasminogen at a dose of 2 mg/0.2 mL/mouse/day via the tail vein, and an equal volume of PBS was administered to mice in the control group administered with vehicle PBS. Whole blood was taken from the removed eyeballs 31 days after administration of plasminogen. After the serum was precipitated, it was centrifuged at 3500 r/min for 10 minutes at 4° C., and the supernatant was taken for detection. In this experiment, the content of alanine transaminase (ALT) in serum was detected by Reitman-Frankel colorimetry using an alanine transaminase detection kit (Nanjing Jiancheng Biological Engineering Research Institute, Catalog No. C009-2).

Figure 17:
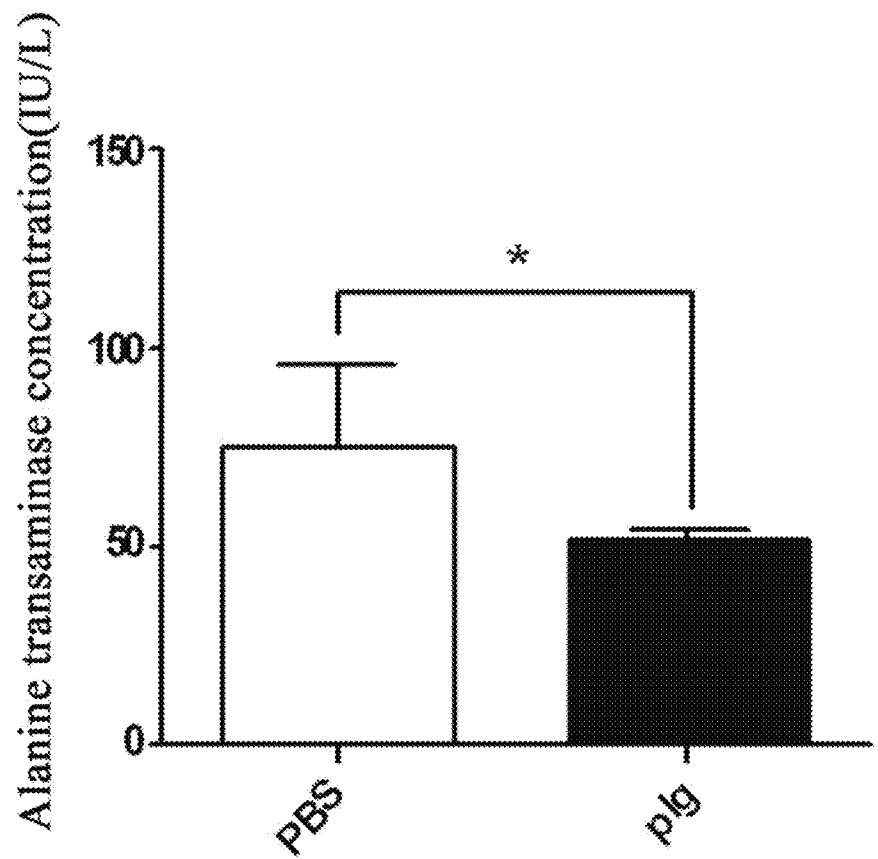
FIG. 17 shows the detection results of alanine transaminase (ALT) in serum after administration of plasminogen to 24-25-week-old diabetic mice for 31 days.

Alanine transaminase is an important index of liver health status[41,42], and the normal reference value interval of alanine transaminase is 9-50 U/L. The detection results showed that the ALT content in serum of mice in the control group administered with vehicle PBS was significantly higher than the normal physiological index, whereas the content in mice in the group administered with plasminogen had returned to normal levels in the body; and the ALT content in mice in the group administered with plasminogen was significantly lower than that in mice in the control group administered with vehicle PBS, and there was a statistical difference (FIG. 17). This indicated that injection of plasminogen can effectively repair the liver injury in model mice with late diabetic diabetes.

REFERENCES

[1] Md. Shahidul Islam, 2013. Animal Models of Diabetic Neuropathy: Progress Since 1960s. Journal of Diabetes Research.

[2] Seaquist E R, Goetz F C, Rich S, Barbosa J: Familial clustering of diabetic kidney disease. Evidence for genetic susceptibility to diabetic nephropathy. N Engl J Med 320: 1161-1165, 1989.

[3] Krolewski A S: Genetics of diabetic nephropathy: Evidence for major and minor gene effects. Kidney Int 55: 1582-1596, 1999.

[4] Iyengar S K, Fox K A, Schachere M, Manzoor F, Slaughter M E, Covic A M, Orloff S M, Hayden P S, Olson J M, Schelling J R, Sedroe J R: Linkage analysis of candidate loci for endstage renal disease due to diabetic nephropathy. J Am Soc Nephrol 14[Suppl 2]: S195-S201, 2003.

[5] Young B A, Maynard C, Boyko E J: Racial differences in diabetic nephropathy, cardiovascular disease, and mortality in a national population of veterans. Diabetes Care 26: 2392-2399, 2003.

[6] Tarnow L, Rossing P, Nielsen F S, Fagerudd J A, Poirier O, Parving H H: Cardiovascular morbidity and early mortality cluster in parents of type 1 diabetic patients with diabetic nephropathy. Diabetes Care 23: 30-33, 2000.

[7] Mauer S M, Lane P, Zhu D, Fioretto P, Steffes M W: Renal structure and function in insulin-dependent diabetes mellitus in man. J Hypertens Suppl 10: S17-S20, 1992.

[8] Alexander C M and Werb, Z. (1991). Extracellular matrix degradation. In Cell Biology of Extracellular Matrix, Hay E D, ed. (New York: Plenum Press), pp. 255-302.

[9] Werb, Z., Mainardi, C. L., Vater, C. A., and Harris, E. D., Jr. (1977). Endogenous activation of latent collagenase by rheumatoid synovial cells. Evidence for a role of plasminogen activator. N. Engl. J. Med. 296, 1017-1023.

[10] He, C. S., Wilhelm, S. M., Pentland, A. P., Marmer, B. L., Grant, G. A., Eisen, A. Z., and Goldberg, G. I. (1989). Tissue cooperation in a proteolytic cascade activating human interstitial collagenase. Proc. Natl. Acad. Sci. U. S. A 86, 2632-2636.

[11] Stoppelli, M. P., Corti, A., Soffientini, A., Cassani, G., Blasi, F., and Assoian, R. K. (1985). Differentiation-enhanced binding of the amino-terminal fragment of human urokinase plasminogen activator to a specific receptor on U937 monocytes. Proc. Natl. Acad. Sci. U. S. A 82, 4939-4943.

[12] Vassalli, J. D., Baccino, D., and Belin, D. (1985). A cellular binding site for the Mr 55, 000 form of the human plasminogen activator, urokinase. J. Cell Biol. 100, 86-92.

[13] Wiman, B. and Wallen, P. (1975). Structural relationship between "glutamic acid" and "lysine" forms of human plasminogen and their interaction with the NH2-terminal activation peptide as studied by affinity chromatography. Eur. J. Biochem. 50, 489-494.

[14] Saksela, O. and Rifkin, D. B. (1988). Cell-associated plasminogen activation: regulation and physiological functions. Annu. Rev. Cell Biol. 4, 93-126.

[15] Raum, D., Marcus, D., Alper, C. A., Levey, R., Taylor, P. D., and Starzl, T. E. (1980). Synthesis of human plasminogen by the liver. Science 208, 1036-1037.

[16] Wallén P (1980). Biochemistry of plasminogen. In Fibrinolysis, Kline D L and Reddy K K N, eds. (Florida: CRC.

[17] Sottrup-Jensen, L., Zajdel, M., Claeys, H., Petersen, T. E., and Magnusson, S. (1975). Amino-acid sequence of activation cleavage site in plasminogen: homology with "pro" part of prothrombin. Proc. Natl. Acad. Sci. U. S. A 72, 2577-2581.

[18] Collen, D. and Lijnen, H. R. (1991). Basic and clinical aspects of fibrinolysis and thrombolysis. Blood 78, 3114-3124.

[19] Alexander, C. M. and Werb, Z. (1989). Proteinases and extracellular matrix remodeling. Curr. Opin. Cell Biol. 1, 974-982.

[20] Mignatti, P. and Rifkin, D. B. (1993). Biology and biochemistry of proteinases in tumor invasion. Physiol Rev. 73, 161-195.

[21] Collen, D. (2001). Ham-Wasserman lecture: role of the plasminogen system in fibrin-homeostasis and tissue remodeling. Hematology. (Am. Soc. Hematol. Educ. Program.) 1-9.

[22] Rifkin, D. B., Moscatelli, D., Bizik, J., Quarto, N., Blei, F., Dennis, P., Flaumenhaft, R., and Mignatti, P. (1990). Growth factor control of extracellular proteolysis. Cell Differ. Dev. 32, 313-318.

[23] Andreasen, P. A., Kjoller, L., Christensen, L., and Duffy, M. J. (1997). The urokinase-type plasminogen activator system in cancer metastasis: a review. Int. J. Cancer 72, 1-22.

[24] Rifkin, D. B., Mazzieri, R., Munger, J. S., Noguera, I., and Sung, J. (1999). Proteolytic control of growth factor availability. APMIS 107, 80-85.

[25] Marder V J, Novokhatny V. Direct fibrinolytic agents: biochemical attributes, preclinical foundation and clinical potential [J]. Journal of Thrombosis and Haemostasis, 2010, 8(3): 433-444.

[26] Hunt J A, Petteway Jr S R, Scuderi P, et al. Simplified recombinant plasmin: production and functional comparison of a novel thrombolytic molecule with plasma-derived plasmin [J]. Thromb Haemost, 2008, 100(3): 413-419.

[27] Sottrup-Jensen L, Claeys H, Zajdel M, et al. The primary structure of human plasminogen: Isolation of two lysine-binding fragments and one "mini"-plasminogen (MW, 38, 000) by elastase-catalyzed-specific limited proteolysis [J]. Progress in chemical fibrinolysis and thrombolysis, 1978, 3: 191-209.

[28] Nagai N, Demarsin E, Van Hoef B, et al. Recombinant human microplasmin: production and potential therapeutic properties [J]. Journal of Thrombosis and Haemostasis, 2003, 1(2): 307-313.

[29] Jae Kyu Ryu, Mark A. Petersen, Sara G. Murray et al. Blood coagulation protein fibrinogen promotes autoimmunity and demyelination via chemokine release and antigen presentation. NATURE COMMUNICATIONS, 2015, 6:8164.

[30] Dimitrios Davalos, Katerina Akassoglou. Fibrinogen as a key regulator of inflammation in disease. Seminars in Immunopathology, 2012. 34(1):43-62.

[31] Valvi D, Mannino D M, Mullerova H, et al. Fibrinogen, chronic obstructive pulmonary disease (COPD) and out-

[32] Moungjaroen J, Nimmannit U, Callery P S, Wang L, Azad N, Lipipun V, Chanvorachote P, Rojanasakul Y (2006). Reactive oxygen species mediate caspase activation and apoptosis induced by lipoic acid in human lung epithelial cancer cells through Bcl-2 downregulation. J Pharmacol Exp Ther 319, 1062-1069.

[33] Wang L, Chanvorachote P, Toledo D, Stehlik C, Mercer R R, Castranova V, Rojanasakul Y (2008). Peroxide is a key mediator of Bcl-2 down-regulation and apoptosis induction by cisplatinin human lung cancer cells. Mol Pharmacol 73, 119-127.

[34] Zwart B, Ciurana C, Rensink I, Manoe R, Hack C E, et al. (2004) Complement activation by apoptotic cells occurs predominantly via IgM and is limited to late apoptotic (secondary necrotic) cells. Autoimmunity 37: 95-102.

[35] Zhang M, Takahashi K, Alicot E M, Vorup-Jensen T, Kessler B, et al. (2006) Activation of the lectin pathway by natural IgM in a model of ischemia/reperfusion injury. J Immunol 177: 4727-4734.

[36] Kim S J, Gershov D, Ma X, Brot N, Elkon K B (2002) I-PLA2 Activation during Apoptosis Promotes the Exposure of Membrane Lysophosphatidylcholine Leading to Binding by Natural Immunoglobulin M Antibodies and Complement Activation. The Journal of Experimental Medicine 196: 655-665.

[37] Cunha-Vaz J, Bernardes R: Nonproliferative retinopathy in diabetes type 2. Initial stages and characterization of phenotypes, Prog Retin Eye Res 2005, 24:355-377.

[38] Roy S, Sato T, Paryani G, Kao R: Downregulation of fibronectin overexpression reduces basement membrane thickening and vascular lesions in retinas of galactose-fed rats. Diabetes 2003, 52: 1229-1234.

[39] S. R. Chaplan et al. Quantitative assessment of tactile allodynia in the rat paw, Journal of Neuroscience Methods 53 (1994) 55-63.

[40] R. Langhorn and J. L. Willesen. Cardiac Troponins in Dogs and Cats. J Vet Intern Med 2016; 30:36-50.

[41] Karmen A, Wroblewski F, Ladue J S (January 1955). Transaminase activity in human blood. The Journal of Clinical Investigation. 34 (1): 126-31.

[42] Wang C S, Chang T T, Yao W J, Wang S T, Chou P (April 2012). Impact of increasing alanine aminotransferase levels within normal range on incident diabetes. Journal of the Formosan Medical Association=Taiwan Yi Zhi. 111 (4): 201-8.

The invention claimed is:

1. A method for treating diabetic nephropathy or one or more diabetic nephropathy-related disorders in a subject, comprising administering an effective amount of plasminogen to the subject, wherein the plasminogen comprises a plasminogen active fragment comprising SEQ ID NO: 14 and has plasminogen activity, wherein the plasminogen is administered by intravenous, intramuscular, subcutaneous, inhalation, catheter administration, local injection or rectal administration, and wherein the plasminogen is administered in combination with one or more other drugs selected from the group consisting of antidiabetic drugs, antithrombotic drugs, antihypertensive drugs, hypolipidemic drugs, drugs against cardiovascular and cerebrovascular diseases, and anti-infective drugs.

2. The method of claim 1, wherein the diabetic nephropathy includes glomerulopathy, comprising glomerular sclerosis and glomerular mesangial hyperplasia; tubulointerstitial lesions; and renal microangiopathy, including renal interstitial fibrosis, renal tubular atrophy, hyaline degeneration of the efferent arteries or renal microvascular sclerosis.

3. The method of claim 1, wherein the diabetic nephropathy-related disorders comprise early renal enlargement, early increased glomerular filtration rate, intermittent proteinuria, microalbuminuria, macroalbuminuria, persistent proteinuria, decreased glomerular filtration rate, injured renal cell, renal fibrosis, renal insufficiency, renal failure or uremia.

4. The method according to claim 1, wherein the diabetic nephropathy is caused by diabetes mellitus-induced angiopathy of large vessels, small vessels or microvessels.

5. The method according to claim 1, wherein the plasminogen has at least 80%, 85%, 90%, 95%, 96%, 97%, 98% or 99% sequence identity with SEQ ID NO: 2, 6, 8, or 10, or the plasminogen has at least 95%, 96%, 97%, 98% or 99% sequence identity with SEQ ID NO: 12, and still has the plasminogen activity.

6. The method according to claim 1, wherein the plasminogen is selected from the group consisting of Glu-plasminogen, Lys-plasminogen, mini-plasminogen, micro-plasminogen, δ (delta)-plasminogen and combinations thereof.

7. The method of claim 1, wherein the plasminogen has at least 80% sequence identity to SEQ ID NO: 2, 6, 8, or 10.

8. The method of claim 1, wherein the plasminogen has at least 90% sequence identity to SEQ ID NO: 2, 6, 8, or 10.

9. The method of claim 1, wherein the plasminogen has the amino acid sequence of SEQ ID NO: 2.

10. The method of claim 1, wherein the plasminogen has the amino acid sequence of SEQ ID NO: 6.

11. The method of claim 1, wherein the plasminogen has the amino acid sequence of SEQ ID NO: 8.

12. The method of claim 1, wherein the plasminogen has the amino acid sequence of SEQ ID NO: 10.

13. The method of claim 1, wherein the plasminogen has the amino acid sequence of SEQ ID NO: 12.

14. The method of claim 1, wherein the method treats diabetic nephropathy in the subject.

15. The method of claim 1, wherein the method treats one or more diabetic nephropathy-related disorders in the subject.

16. The method of claim 1, wherein the method treats diabetic nephropathy and one or more diabetic nephropathy-related disorders in the subject.

17. The method of claim 1, wherein the plasminogen is administered intravenously.

18. A method for treating diabetic nephropathy or one or more diabetic nephropathy-related disorders in a subject, comprising administering an effective amount of plasminogen to the subject, wherein the plasminogen comprises a plasminogen active fragment comprising SEQ ID NO: 14 and has plasminogen activity, wherein the plasminogen is administered systemically, and wherein the plasminogen is adminstered in combination with one or more other drugs selected from the group consisting of antidiabetic drugs, antithrombotic drugs, antihypertensive drugs, hypolipidemic drugs, drugs against cardiovascular and cerebrovascular diseases, and anti-infective drugs.

19. A method for treating diabetic nephropathy or one or more diabetic nephropathy-related disorders in a subject, comprising administering an effective amount of plasminogen to the subject, wherein the plasminogen comprises a plasminogen active fragment comprising SEQ ID NO: 14 and has plasminogen activity, wherein the plasminogen is administered locally, and wherein the plasminogen is adminstered in combination with one or more other drugs selected from the group consisting of antidiabetic drugs, antithrombotic drugs, antihypertensive drugs, hypolipidemic drugs, drugs against cardiovascular and cerebrovascular diseases, and anti-infective drugs.

* * * * *